(12) United States Patent
Carola et al.

(10) Patent No.: US 7,863,478 B2
(45) Date of Patent: Jan. 4, 2011

(54) UV FILTERS

(75) Inventors: Christophe Carola, Heidelberg (DE);
Frank Pfluecker, Darmstadt (DE);
Herwig Buchholz, Frankfurt am Main (DE); Hansjürgen Driller, Gross-Umstadt (DE); Hans Neunhoeffer, Muehltal (DE); Evgeniy V. Blyumin, Toronto (CA)

(73) Assignee: Merck Patent GmbH, Darmstadt (DE)

( * ) Notice: Subject to any disclaimer, the term of this patent is extended or adjusted under 35 U.S.C. 154(b) by 793 days.

(21) Appl. No.: 11/573,657

(22) PCT Filed: Jul. 27, 2005

(86) PCT No.: PCT/EP2005/008141
§ 371 (c)(1),
(2), (4) Date: Feb. 13, 2007

(87) PCT Pub. No.: WO2006/018104
PCT Pub. Date: Feb. 23, 2006

(65) Prior Publication Data
US 2008/0038213 A1 Feb. 14, 2008

(30) Foreign Application Priority Data
Aug. 13, 2004 (DE) .................. 10 2004 039 281

(51) Int. Cl.
| | |
|---|---|
| *C07C 69/10* | (2006.01) |
| *C07C 233/10* | (2006.01) |
| *C07C 235/00* | (2006.01) |
| *C07C 237/00* | (2006.01) |
| *A61K 8/42* | (2006.01) |
| *A61K 8/37* | (2006.01) |
| *A61Q 17/00* | (2006.01) |
| *C07D 251/54* | (2006.01) |
| *C07D 403/10* | (2006.01) |

(52) U.S. Cl. .................. 560/203; 564/161; 568/303; 252/400.3; 252/403; 424/70.12; 424/70.9

(58) Field of Classification Search .................. 560/203; 564/161; 568/303; 252/400.3, 403; 424/70.12, 424/70.9
See application file for complete search history.

(56) References Cited

U.S. PATENT DOCUMENTS

| | | | |
|---|---|---|---|
| 3,862,951 | A | 1/1975 | Gottwald et al. |
| 5,600,007 | A | 2/1997 | Martin et al. |
| 5,693,670 | A | 12/1997 | Philippe et al. |
| 5,877,204 | A | 3/1999 | Davison et al. |
| 5,932,232 | A | 8/1999 | De Salvert et al. |
| 5,972,313 | A | 10/1999 | Tuloup et al. |
| 6,613,341 | B2 | 9/2003 | Motley et al. |

FOREIGN PATENT DOCUMENTS

| | | |
|---|---|---|
| EP | 0709081 A1 | 5/1996 |
| EP | 0710478 A1 | 5/1996 |
| EP | 0581954 B1 | 7/1996 |
| EP | 0796838 A | 9/1997 |
| EP | 0758314 B1 | 9/1999 |

*Primary Examiner*—Venkataraman Balasubramanian
(74) *Attorney, Agent, or Firm*—Millen, White, Zelano & Branigan, P.C.

(57) ABSTRACT

The invention relates to compounds of the formula (I) or (II), to compositions which comprise such compounds, to corresponding processes for the preparation of the compounds or the compositions comprising same, and to the use thereof as light-protection filters.

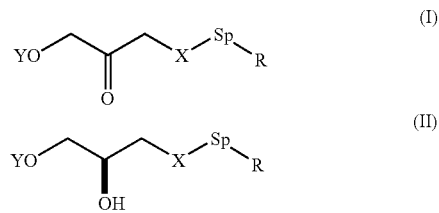

25 Claims, 2 Drawing Sheets

UV FILTERS

Figure 1:
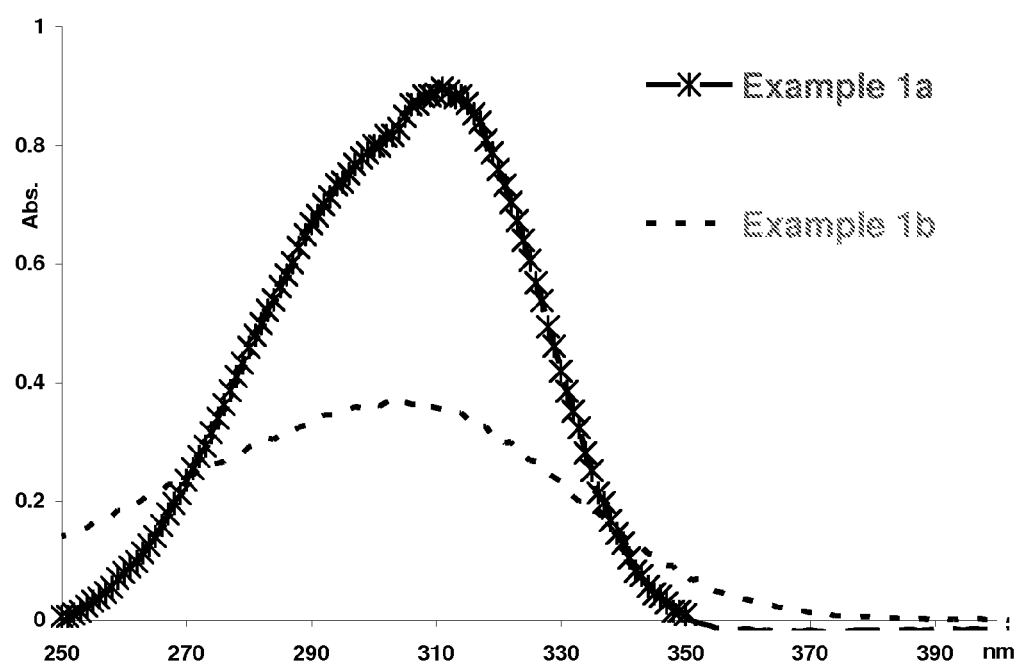

The invention relates to UV filters, to compositions which comprise such UV filters, to corresponding processes for the preparation of the UV filters or the compositions comprising same, and to the use thereof.

In particular, the invention relates to the use of α-hydroxyketone derivatives as light-protection filters for cosmetic or pharmaceutical products and to novel α-hydroxyketone derivatives, to processes for the preparation thereof and to the use thereof in cosmetic compositions, in particular for protection against solar radiation and in pharmaceutical compositions.

The human skin is subject to certain ageing processes, some of which are attributable to intrinsic processes (chrono-ageing) and some of which are attributable to exogenous factors (environmental, for example photoageing). In addition, temporary or even lasting changes to the skin picture can occur, such as acne, greasy or dry skin, keratoses, rosaceae, light-sensitive, inflammatory, erythematous, allergic or autoimmune-reactive reactions, such as dermatosis and photomatosis.

The exogenous factors include, in particular, sunlight or artificial radiation sources having a comparable spectrum, and compounds which can be formed by the radiation, such as undefined reactive photoproducts, which may also be free-radical or ionic. These factors also include cigarette smoke and the reactive compounds present therein, such as ozone, free radicals, for example the hydroxyl free radical, singlet oxygen and other reactive oxygen or nitrogen compounds which interfere with the natural physiology or morphology of the skin.

The influence of these factors can result, inter alia, in direct damage to the DNA of the skin cells and to the collagen, elastin or glycosaminoglycan molecules of the extracellular matrix, which are responsible for the strength of skin. In addition, the signal transduction chains, which are terminated by the activation of matrix-degrading enzymes, may be affected. Important representatives of these enzymes are the matrix metalloproteinases (MMPs, for example collagenases, gelatinases and stromelysins), whose activity is additionally regulated by TIMPs (tissue inhibitors of matrix metalloproteinases).

The consequences of the above-mentioned ageing processes are thinning of the skin, weaker interlacing of epidermis and dermis, and a reduction in the number of cells and the supplying blood vessels. This results in the formation of fine lines and wrinkles, the skin becomes leathery, and pigment defects can occur.

The same factors also act on hair, where damage can likewise occur. The hairs become brittle, less elastic and dull. The surface structure of the hairs is damaged.

There is therefore a demand for further compounds which absorb UV radiation and are thus capable of protecting the human skin.

It has now been found that certain dihydroxyacetone derivatives are suitable for this purpose.

The present application therefore relates firstly to compounds of the formula I

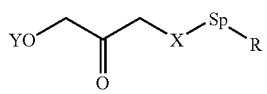

I in which
X stands for O, $S(O)_m$ or $NR^1$,
Y stands for H, $—SiR^2R^3R^4$ or $—[Si(R^2)_2]_q SiR^3R^4R^5$ or -Sp-R,
$R^1$ stands for H, $C_{1-24}$-alkyl or R,
$R^2$, $R^3$, $R^4$ and $R^5$ each, independently of one another, stand for $C_{1-30}$-alkyl,
Sp stands for $—(CH_2)_n—$, $—(CH_2)_n—C(=O)—(CH_2)_o—$ or $—(CH_2)_n—C(=O)—(CH_2)_o—X—(CH_2)_p—$,
m stands for an integer selected from 0, 1 or 2,
n, o, p stand for an integer selected, independently of one another, from the range beginning with 0 and ending with 24 and
R stands for a substituent which absorbs UV radiation, where R may in turn be substituted by one or more -Sp-X—$CH_2$—C(=O)—$CH_2$—OH groups,
where different R and X in formula I may stand for identical or different radicals.

The present invention furthermore relates to compounds of the formula II

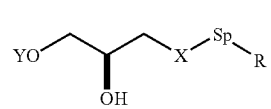

II in which
X stands for O, $S(O)_m$ or $NR^1$,
Y stands for H, $R^1$, $[Si(R^2)_2]_q SiR^3R^4R^5$ or -Sp-R,
$R^1$ stands for H, $C_{1-30}$-alkyl or R,
$R^2$, $R^3$, $R^4$ and $R^5$ each, independently of one another, stand for $C_{1-30}$-alkyl,
Sp stands for $—(CH_2)_n—$, $—(CH_2)_n—C(=O)—(CH_2)_o—$ or $—(CH_2)_n—C(=O)—(CH_2)_o—X—(CH_2)_p—$,
m stands for an integer selected from 0, 1 or 2,
n, o, p, q stand for an integer selected, independently of one another, from the range beginning with 0 and ending with 40 and
R stands for a substituent which absorbs UV radiation and has a conjugated π-electron system comprising at least 4π electrons, where R may in turn be substituted by one or more -Sp-X—$CH_2$—C(=O)—$CH_2$—OH groups,
where different R and X in formula II may stand for identical or different radicals.

The compounds of the formula II according to the invention are firstly themselves suitable as UV filters and secondly are valuable intermediates in the synthesis of compounds of the formula I.

The invention furthermore relates to compositions which comprise at least one compound of the formula I or II.

The present invention furthermore relates to the use of at least one compound of the formula I or II or a composition which comprises at least one compound of the formula I or II for the care, preservation or improvement of the general condition of the skin or hair and preferably for prophylaxis against time- and/or light-induced ageing processes of the human skin or human hair, in particular for prophylaxis against dry skin, wrinkling and/or pigment defects, and/or for the reduction or prevention of damaging effects of UV rays on the skin and for prophylaxis against or reduction of skin unevenness, such as wrinkles, fine lines, rough skin or large-pored skin, in accordance with the advantageous properties of the compounds according to the invention.

The conventional light-protection filters generally have low or inadequate skin adhesion, which results in a shorter duration of the protective action of the filter and in particular virtually complete removal of the filter during bathing.

It thus continues to appear desirable to provide compounds which are able to protect the human skin against UV rays for a long time.

The present invention solves this problem with the compounds which are preferred in accordance with the invention, in which Y stands for H. These compounds according to the invention are capable of linking chemically to the skin.

It is known that α-hydroxyketone derivatives have excellent skin adhesion and in some cases a self-tanning effect, like, for example, other hydroxyketo compounds (dihydroxyacetone).

EP 0 758 314 B1 discloses maleimides and maleic acid derivatives which are able to react with SH groups present in the skin.

U.S. Pat. No. 6,613,341 B2 discloses α,β-unsaturated ketones which are chemically linked to UV filters or antioxidants.

EP 0 581 954 B1 discloses α-hydroxyketoalkyl derivatives.

WO 2001085124 discloses various silylated compounds (inter alia silylated DHA) which can be employed as precursor for self-tanning agents in cosmetic formulations.

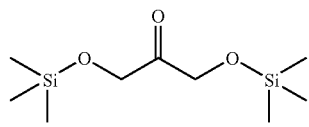

EP 796838 A1 discloses DHA carbonates which can be used as self-tanning agents in cosmetic formulations.

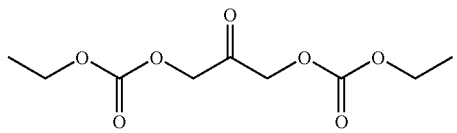

EP 710478 A1 and EP 709081 A1 disclose DHA-fatty acid esters which can be used together with lipase as self-tanning agents in creams.

DE 19720831 discloses some DHA esters which can be used as self-tanning agents and sunscreens.

In preferred variants of the present invention, the radical(s) R stand for structures which are known from conventional UV filters. It is particularly preferred in accordance with the invention for R to stand for a radical selected from the group containing the following elements

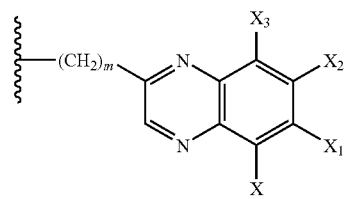

-continued

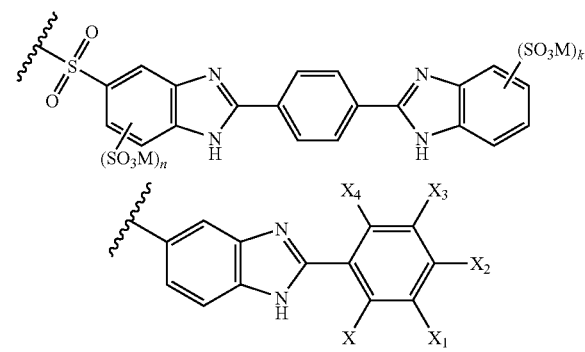

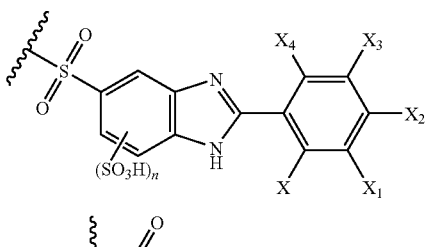

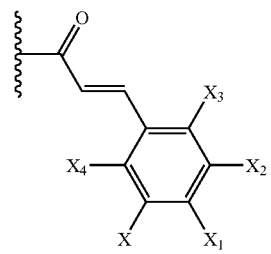

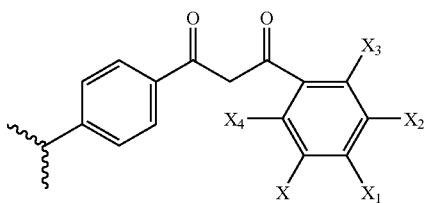

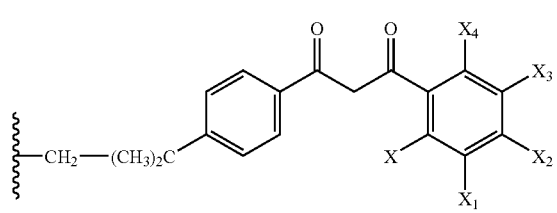

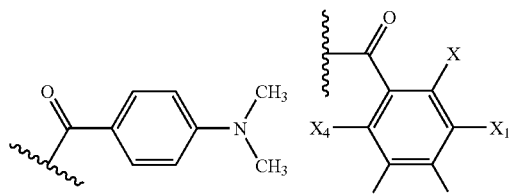

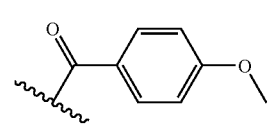

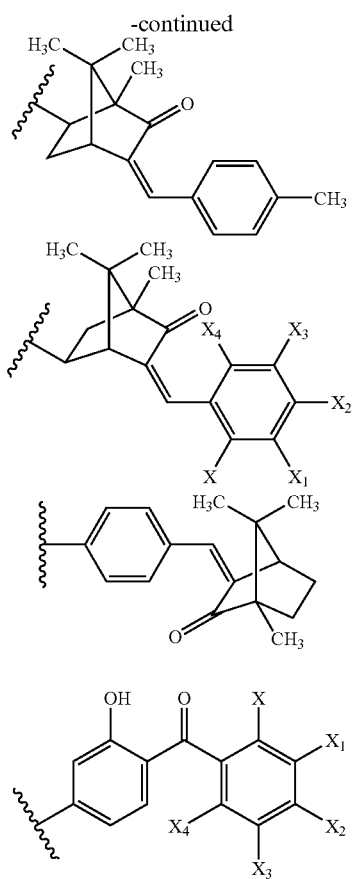

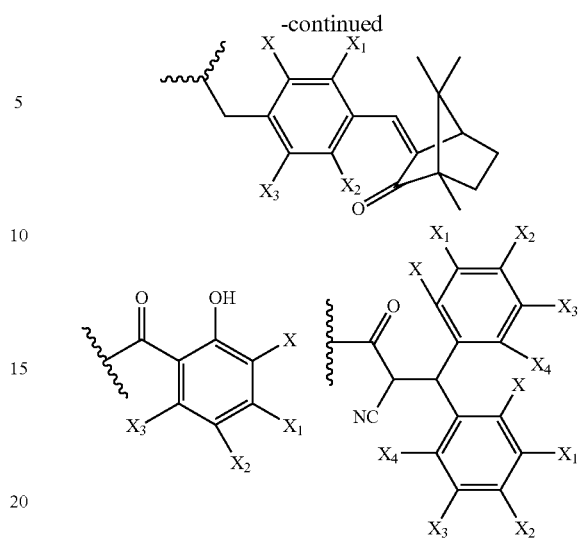

in which X, $X_1$, $X_2$, $X_3$ and $X_4$ each, independently of one another, denote H, OH, $CH_3COO$, an alkyl radical having 1 to 8 C atoms, particularly preferably an alkoxy radical having 1 to 8 C atoms, particularly preferably —O—C$(CH_3)_3$, —O—CH$(CH_3)_2$ or -ethylhexyloxy, or a monoglycoside radical, n is 0, 1, 2 or 3, m is 0 or 1, 2, 3 or 4, and M is H, Na or K.

In a group of compounds of the formula I which are preferably to be employed as UV filters, X stands for O, and the compound is particularly preferably one from the following group:

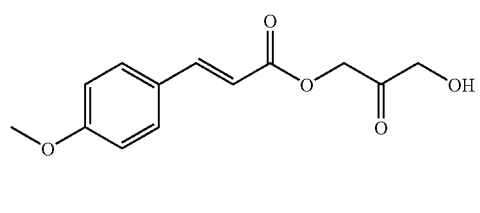

Ia

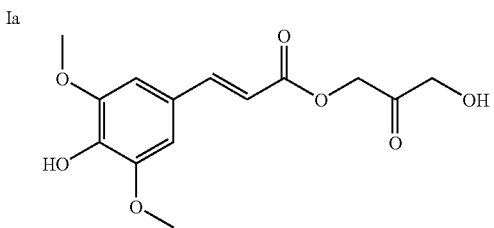

Ib

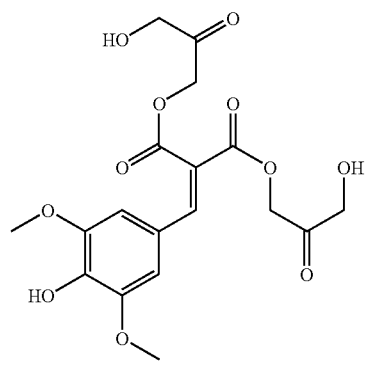

Ic

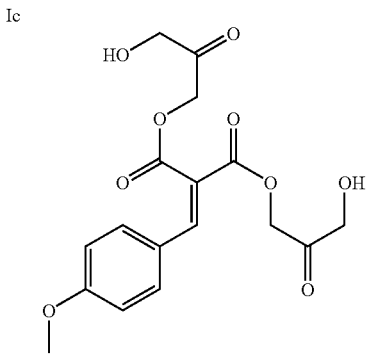

Id

-continued
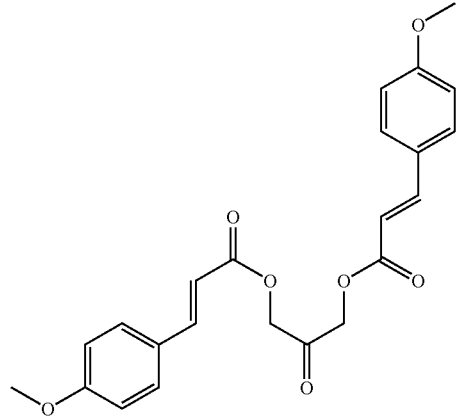
Ie
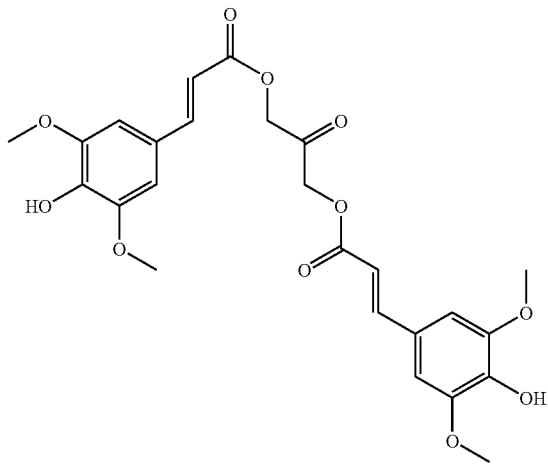
If
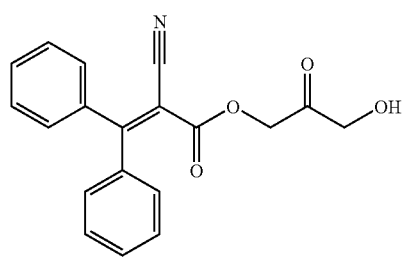
Ig
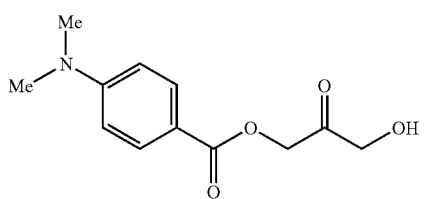
Ih
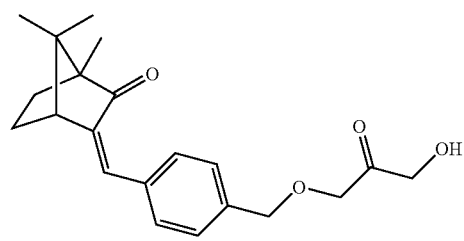
Ii
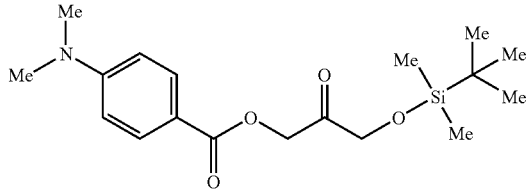
Ij
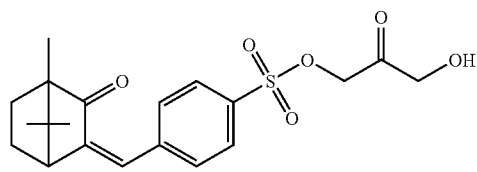
Ik
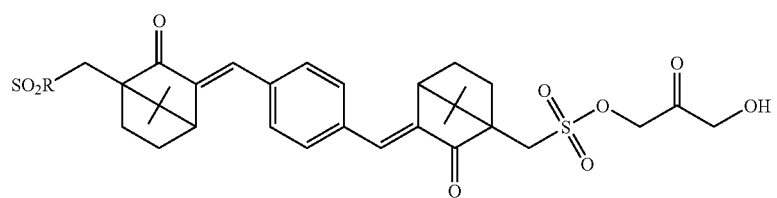
Im
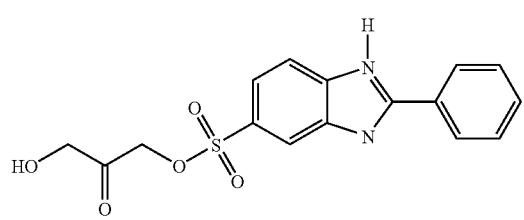
In
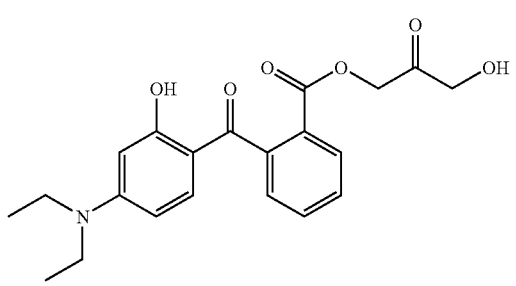
Io -continued
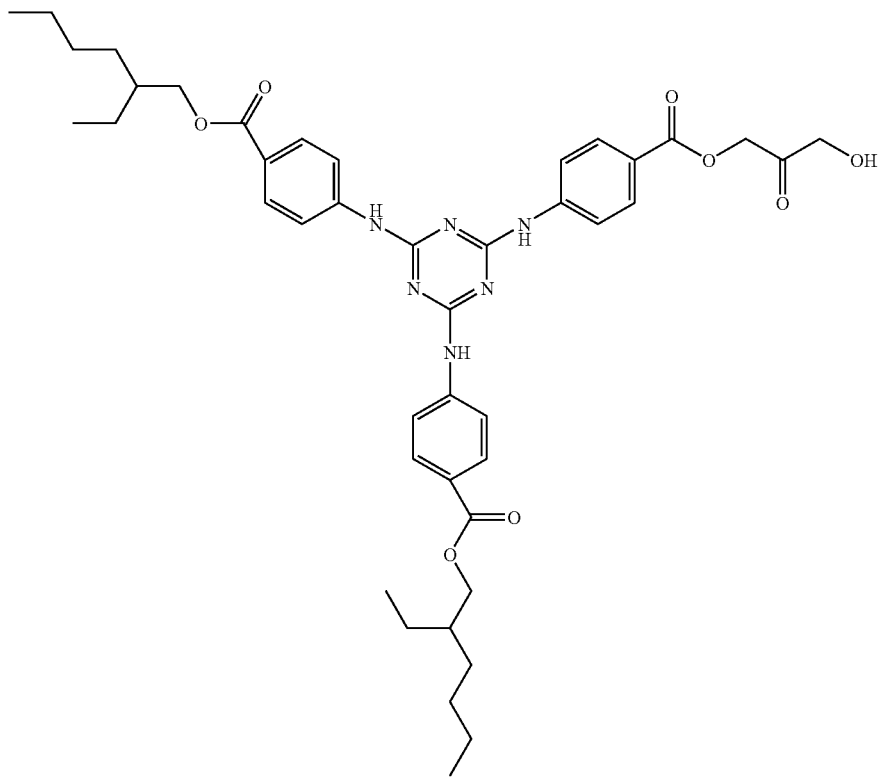
Ip
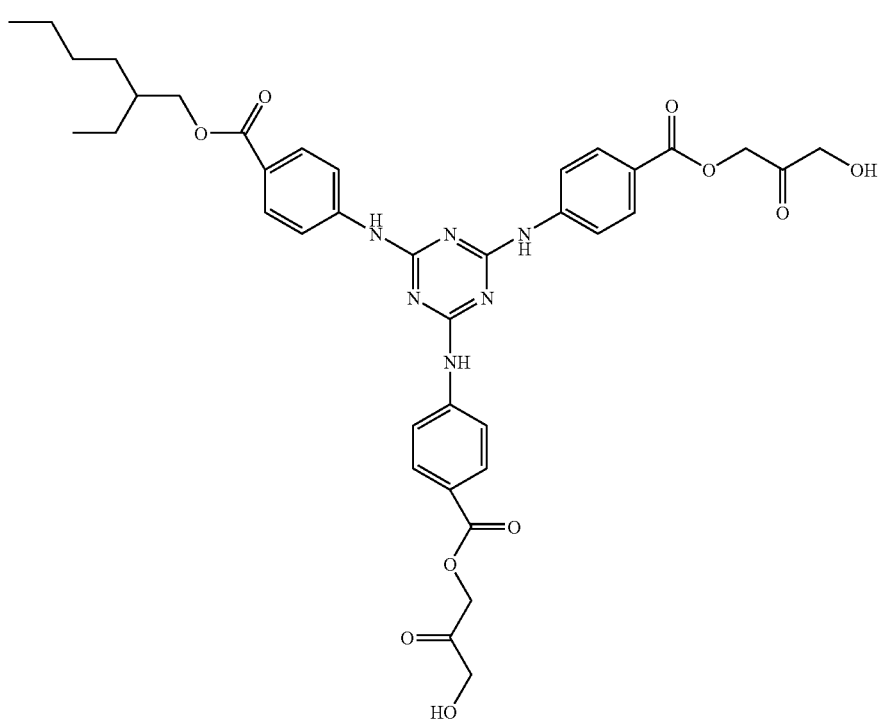
Iq

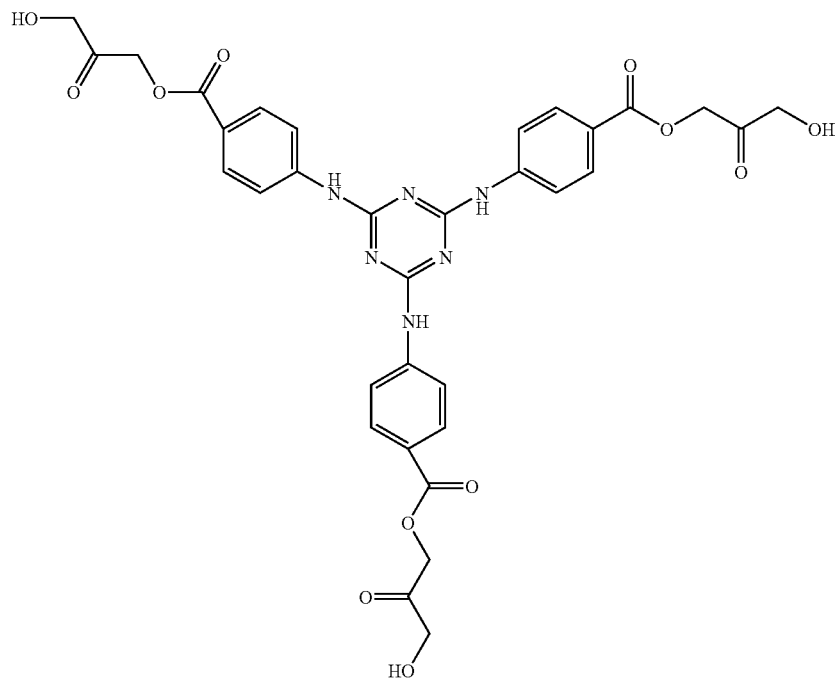

Ir

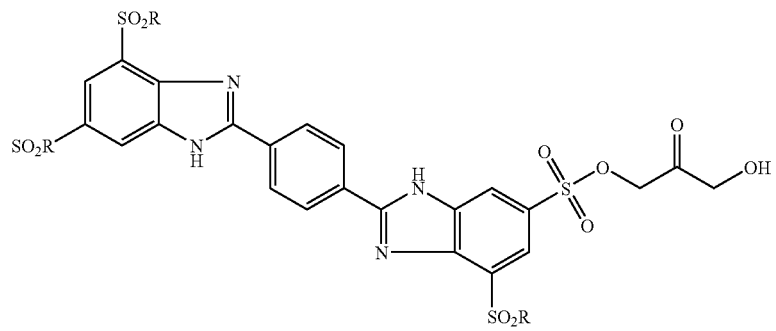

Is where all R, independently of one another, stand for OH, ONa or OCH$_2$COCH$_2$OH In a further class of UV filters which is preferred in accordance with the invention, Y stands for Sp-R, i.e. two units R which absorb UV radiation are present in the molecule. In a preferred group of these compounds, X stands for O, where the two groups Sp-R in the molecule are preferably identical, and the compound is preferably selected from the group of the compounds

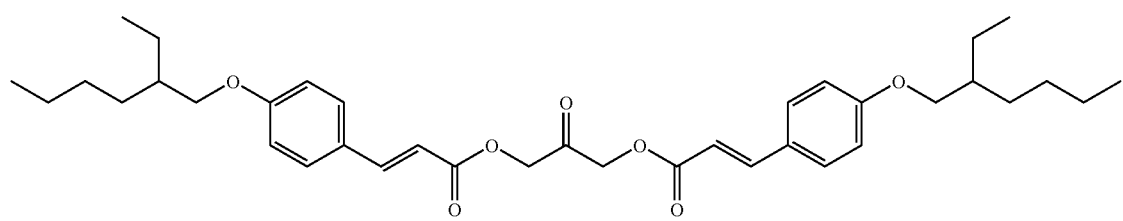

It

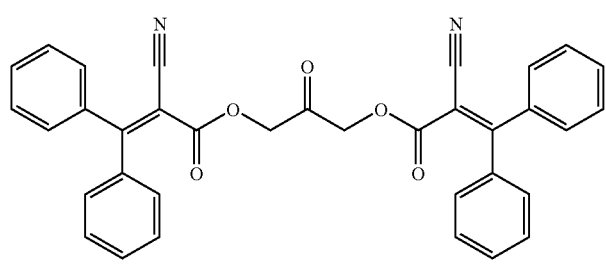
Compounds of the formula I in which X stands for NR¹ are a further preferred class of substances in accordance with the present invention. R¹ here preferably stands for H, and the compounds are particularly preferably selected from the group of compounds Iv-Iae:
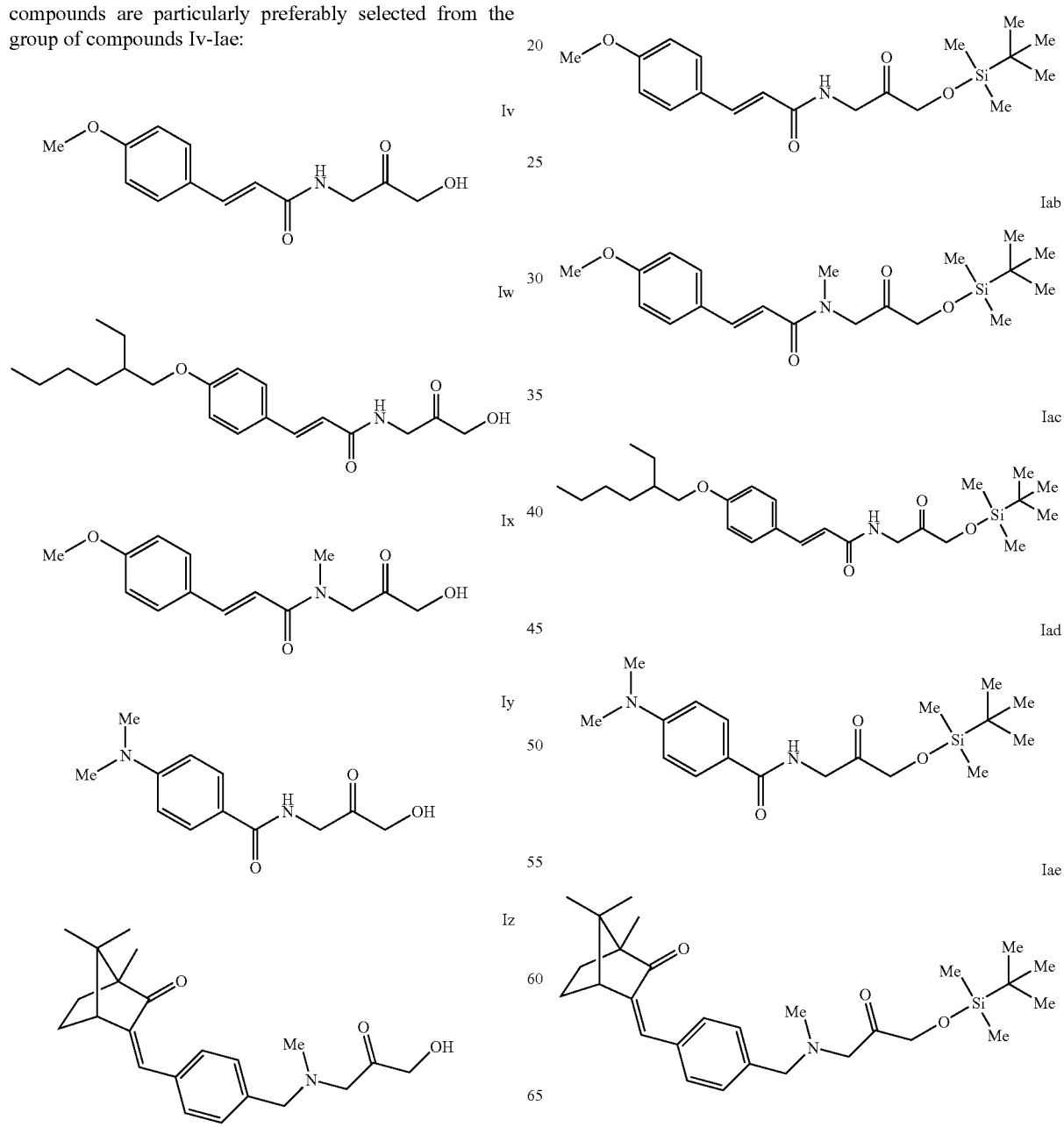

The present invention furthermore relates to compounds of the formula II

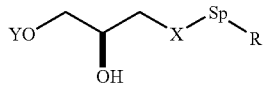
II in which
- X stands for O, S(O)$_m$ or NR$^1$,
- Y stands for H, R$^1$, [Si(R$^2$)$_2$]$_q$SiR$^3$R$^4$R$^5$ or -Sp-R,
- R$^1$ stands for H, C$_{1-30}$-alkyl or R,
- R$^2$, R$^3$, R$^4$ and R$^5$ each, independently of one another, stand for C$_{1-30}$-alkyl,
- Sp stands for —(CH$_2$)$_n$—, —(CH$_2$)$_n$—C(=O)—(CH$_2$)$_o$— or —(CH$_2$)$_n$—C(=O)—(CH$_2$)$_o$—X—(CH$_2$)$_p$—,
- m stands for an integer selected from 0, 1 or 2,
- n, o, p, q stand for an integer selected, independently of one another, from the range beginning with 0 and ending with 40 and
- R stands for a substituent which absorbs UV radiation and has a conjugated π-electron system comprising at least 4π electrons, where R may in turn be substituted by one or more -Sp-X—CH$_2$—C(=O)—CH$_2$—OH groups,
- where different R and X in formula II may stand for identical or different radicals.

The compounds of the formula II according to the invention are firstly themselves suitable as UV filters and secondly are valuable intermediates in the synthesis of compounds of the formula I.

The present application therefore furthermore relates to the use of a compound of the formula II for the preparation of a compound of the formula I.

Preference is given in accordance with the invention to compounds of the formula II in which the radicals R conform to the definitions already indicated above for the compounds of the formula I.

Particular preference is given to compounds of the formula II from the following group:

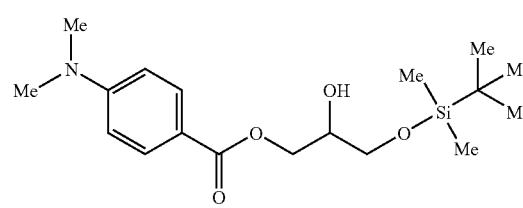
IIa

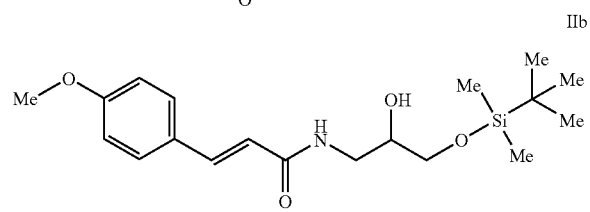
IIb

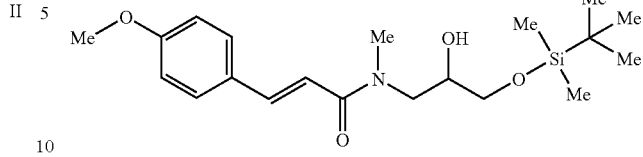
IIc

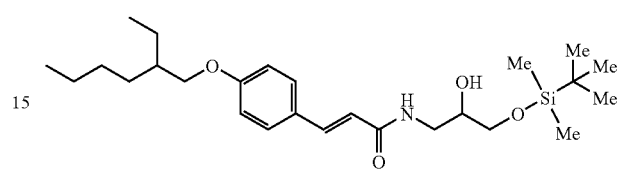
IId

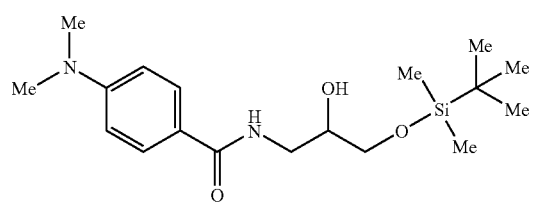
IIe

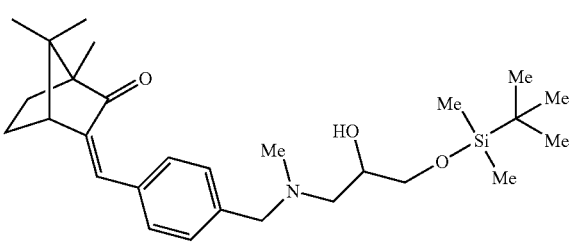
IIf

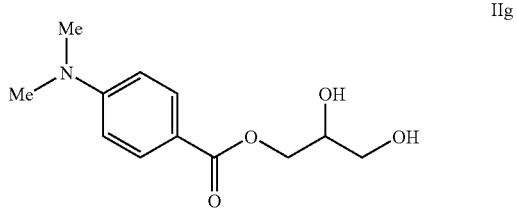
IIg

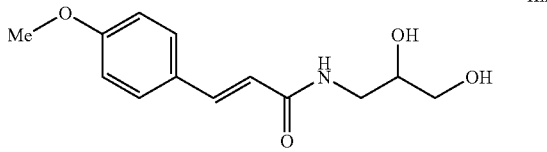
IIh

IIi

IIj

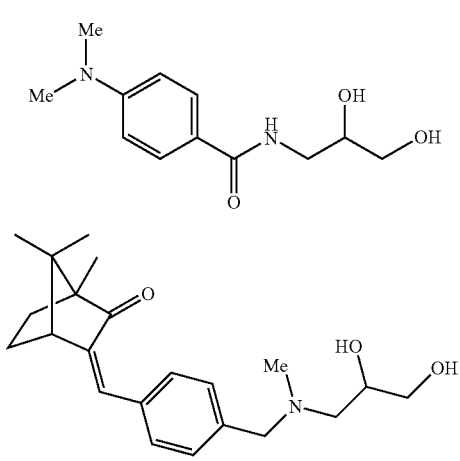

The compounds according to the invention can, depending on the heteroatom X and chromophore "R", be prepared by various synthetic principles.

Thus, the present invention furthermore relates to a process for the preparation of compounds of the formula I where X stands for O, characterised in that dihydroxyacetone or a dihydroxyacetone derivative in which a hydroxyl group is provided with a protective function is reacted with an acid chloride R—(CH$_2$)$_m$—(C=O)Cl.

The reaction of acid chlorides with dihydroxyacetone (DHA) in each case gives a mixture of the monosubstituted and disubstituted products,

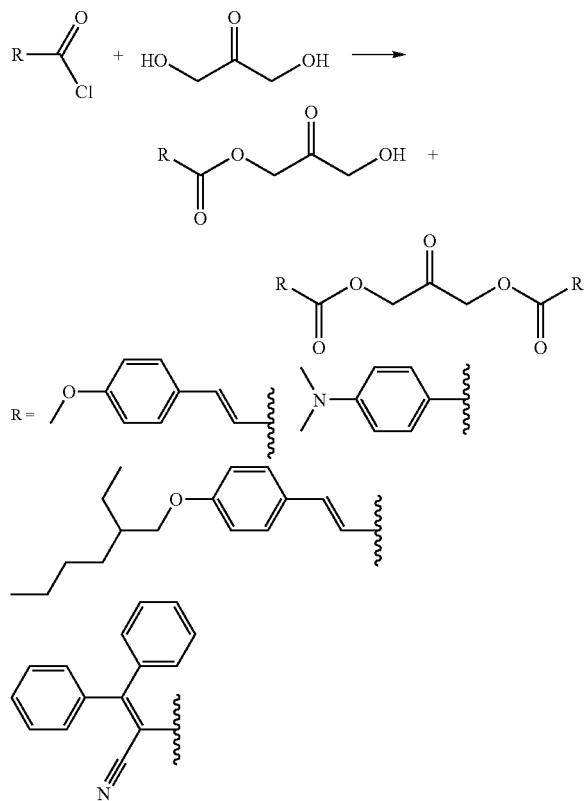

The preparative acylation is carried out in solvents which are inert to acid chlorides (such as, for example, pyridine, dimethylformamide, acetonitrile and ionic liquids). It is furthermore preferred to carry out the reaction in aqueous-alkaline solution. To this end, the so-called Schotten-Baumann process is preferably used, in which, for example, the corresponding acid chlorides are reacted with DHA in the presence of sodium hydroxides. Virto et al. (C. Virto, I. Svensson, P. Adlercreutz, *Biocatalysis and Biotransformation* 2000, 18, 13. C. Virto, P. Adlercreutz, *Chemistry and Physics of Lipids* 2000, 104, 175) report on the esterification of DHA using lauric acid with the aid of lipase B from *Candida antarctica*. By varying the reaction conditions and solvents, 1-lauroyldihydroxyacetone (n=10) was successfully isolated as the principal product of this reaction.

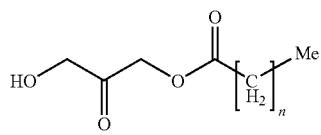

n = 10, 14, 16

In order to prevent the acid chloride in solution converting the mono-DHA derivative into the bis-product after monoacylation has taken place, a route was sought which gives exclusively the desired mono-DHA derivative.

The reaction of dihydroxyacetone (DHA) with a 3-fold molar excess of the corresponding acid chloride in each case gives the disubstituted product.

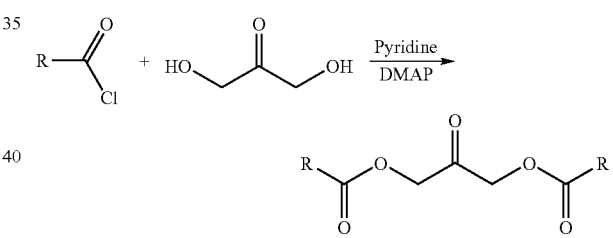

If a hydroxyl group of the DHA is substituted by an acyl, alkyl or silyl radical, the acylation takes place at the free hydroxyl group. The disubstituted DHA thus formed can be converted into a mono-product after deprotection.

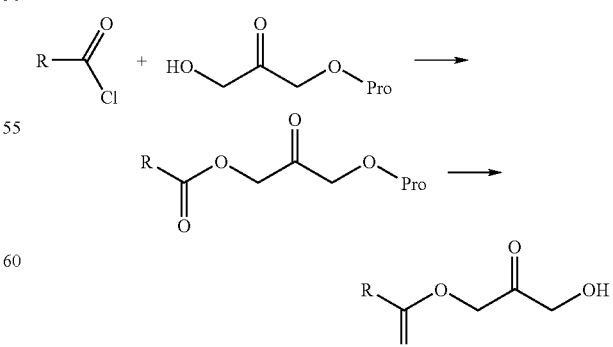

Pro: Si(Me$_2$)CM$_3$, Si(Ph$_2$)Alk; COCMe$_3$, C(O)Alk, CPh$_3$, CPh$_2$(p-OMe), CH$_2$Ph, CH$_2$OCH$_3$ etc.

The literature discloses some monosubstituted DHA derivatives which can preferably be employed in this synthetic strategy. Thus, for example, triphenylmethyl, t-butyl (dimethylsilyl) or pivaloyl and other derivatives are synthesised successfully and in satisfactory yields (J. Balint, G. Egri, A. Kolbert, C. Dianoczky, E. Fogassy, L. Novak, L. Poppe, *Tetrahedron: Asymmetry* 1999, 10, 4017. F. Aragozzini, E. Maconi, D. Potenza, C. Scolastico, *Synthesis* 1989, 225. J. Schröeder, P. Welzel, *Tetrahedron* 1994, 50, 6839. E. Cesarotti, P. Antognazza, A. Mauri, M. Pallavicini, L. Villa, *Helv. Chim. Acta* 1992, 75, 2563. J. R. Deverre, P. Loiseau, F. Puisieux, P. Gayral, Y. Letourneux, J. P. Benoit, *Arzneim. Forsch.* 1992, 42, 1153. S. Rajiv, L. Jewoo, W. Shaomeng, M. A. M. George, E. L. Nancy, et. al., *J. Med. Chem.* 1996, 39, 19. Team of authors, *Organikum*, Wiley-VCH, Weinheim, 2001. C. Bouillon, C. Vayssie, in *Ger. Offen.*, (Oreal S. A., Fr.). Appl: DE 19780314. 78-2811041, 1978, p. 71. C. Bouillon, C. Vayssie, in *Fr. Demande*, (Oreal S. A., Fr.), Fr, Number 2421878, 1979, p. 31. C. Bouillon, C. Vayssie, (Oreal S. A., Fr.). Ca, Number 1113480, 1981, p. 61. M. W. Chun, D. H. Shin, H. R. Moon, J. Lee, H. Park, L. S. Jeong, *Bioorg. Med. Chem. Lett* 1997, 7, 1475). The removal of the protecting group of the DHA-acyl derivatives can be carried out under mild reaction conditions. The silyl ethers can easily be hydrolysed by means of fluoride-containing reagents under mild conditions. For this reason, the silyl derivatives are preferably used.

Thus, for example, 1-(tert-butyldimethylsilyloxy)-3-hydroxy-2-oxopropane can be reacted with 4-dimethylaminobenzoyl chloride under an inert gas in absolute pyridine.

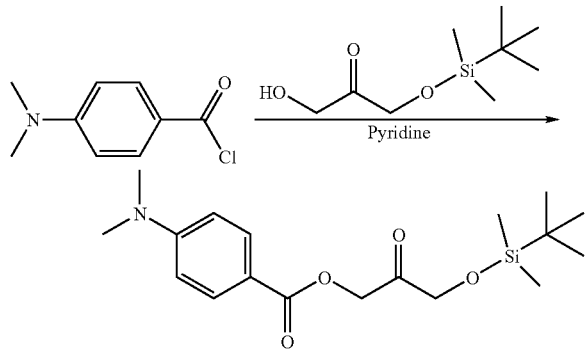

It was also possible to prepare the compounds of the formula I starting from corresponding DHA precursors. This opens up a further route for the synthesis of the DHA derivatives. This synthetic concept is based on the monoacylated glycerin derivatives.

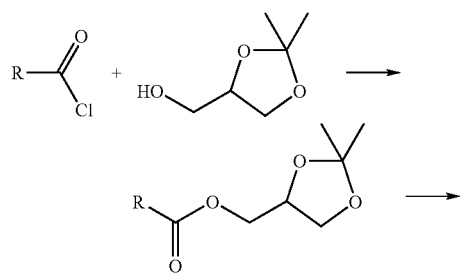

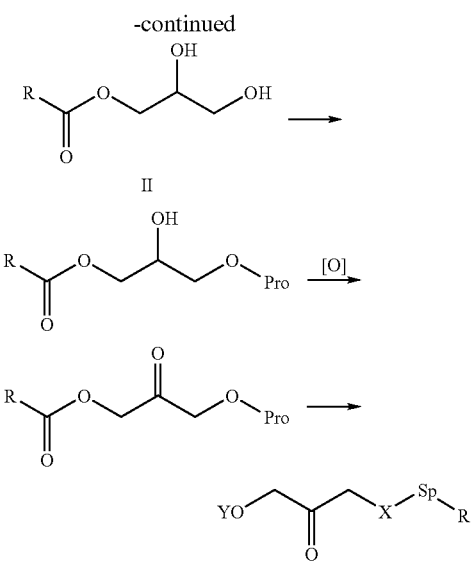

Pro: see above scheme

Consequently, the present invention furthermore relates to a process for the preparation of compounds of the formula II where X stands for O, which is characterised in that an acid chloride R—(CH$_2$)$_m$—(C=O)Cl is reacted with a compound

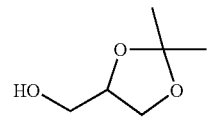

and the acetal is subsequently cleaved.

In order to prepare an α-hydroxyketone of the formula I from a compound of the formula II, the secondary hydroxyl group must firstly be oxidised. It is known that the primary hydroxyl groups can generally be oxidised more quickly than the secondary hydroxyl groups. On the other hand, oxidation of 1,2-diols sometimes results in cleavage of the C—C bond. Accordingly, the primary hydroxyl group is preferably first protected regioselectively, and the secondary hydroxyl group is then converted into a ketone by means of an oxidant (such as, for example, NaBrO$_2$, NaBrO$_3$, pyridinium chlorochromate (PCC), CrO$_3$, peroxides, K$_2$Cr$_2$O$_7$, Ag$_2$CO$_3$, halogens, transition-metal oxides, hypervalent iodine compounds (Dess-Martin periodination) and others (team of authors, *Organikum*, Wiley-VCH, Weinheim, 2001; E. Cesarotti, P. Antognazza, A. Mauri, M. Pallavicini, L. Villa, *Helv. Chim. Acta* 1992, 75, 2563). The primary hydroxyl group is preferably protected regioselectively by sterically demanding reagents. In particular, preference is given to the use of bulky silyl reagents (Pro=SiAlk$_3$).

If, for example, an amide is oxidised by the Swern process (J. R. Deverre, P. Loiseau, F. Puisieux, P. Gayral, Y. Letourneux, J. P. Benoit, *Arzneim. Forsch.* 1992, 42, 1153), the corresponding ketone is obtained in excellent yield.

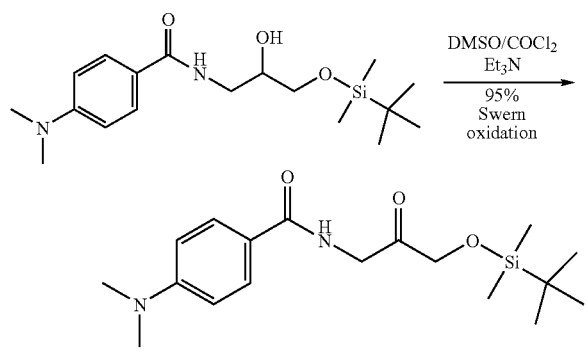

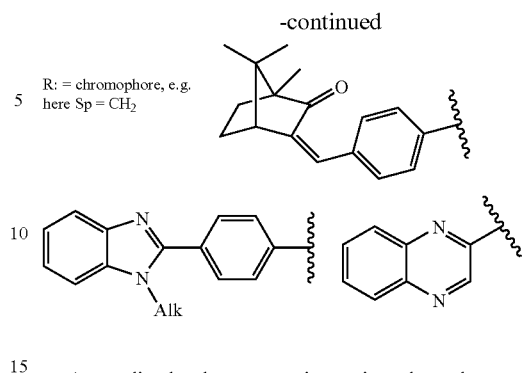

Consequently, the present invention furthermore relates to a process for the preparation of compounds of the formula I in which a compound of the formula II is oxidised on the secondary hydroxyl group using an oxidant.

The DHA molecule can also be coupled to other electrophilic reagents.

For example, the Ar—CH$_3$ group in methylbenzylidenecamphor can be converted into an alkyl bromide. The camphor derivative is brominated by means of N-bromosuccinimide in the presence of initiators (C. Bouillon, C. Vayssie, in *Ger. Offen.*, (Oreal S. A., Fr.). Appl: DE 19780314. 78-2811041, 1978, p. 71. C. Bouillon, C. Vayssie, in *Fr. Demande*, (Oreal S. A., Fr.), Fr, Number 2421878, 1979, p. 31. C. Bouillon, C. Vayssie, (Oreal S. A., Fr.). Ca, Number 1113480, 1981, p. 61).

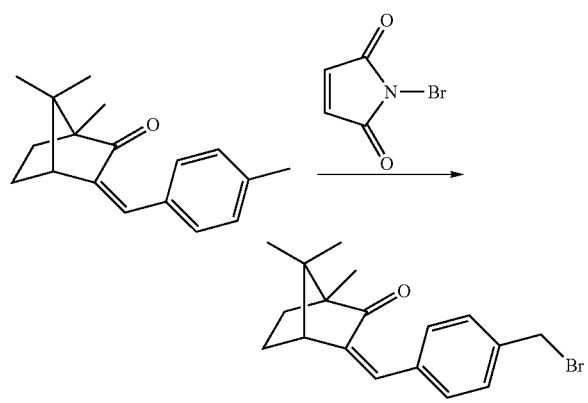

Further coupling to 2,2-dimethoxy-1,3-propanediol gives an intermediate, which can be hydrolysed further without problems to the compound of the formula I.

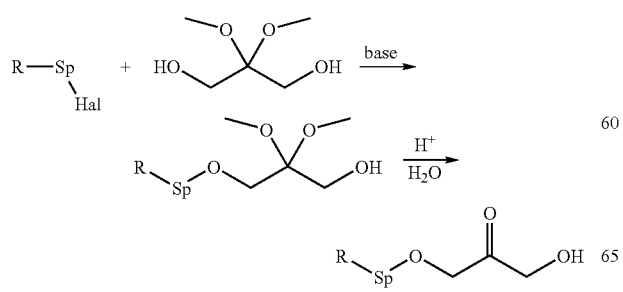

Accordingly, the present invention also relates to a process for the preparation of compounds of the formula I where X stands for O, which is characterised in that 2,2-dimethoxy-1,3-propanediol is reacted with a compound R-Sp-Hal, where Hal stands for Cl, Br or I, and the other radicals conform to the definition indicated above, and the dimethoxy function is subsequently hydrolysed to the ketone.

The compounds of the formula I or II in which X=NR$^1$ are particularly interesting since by means of them the α-hydroxyketone unit and chromophores can be linked to one another by amide bonds. This gives the compounds increased stability. The preparation can be achieved, for example, in accordance with the following synthetic sequence.

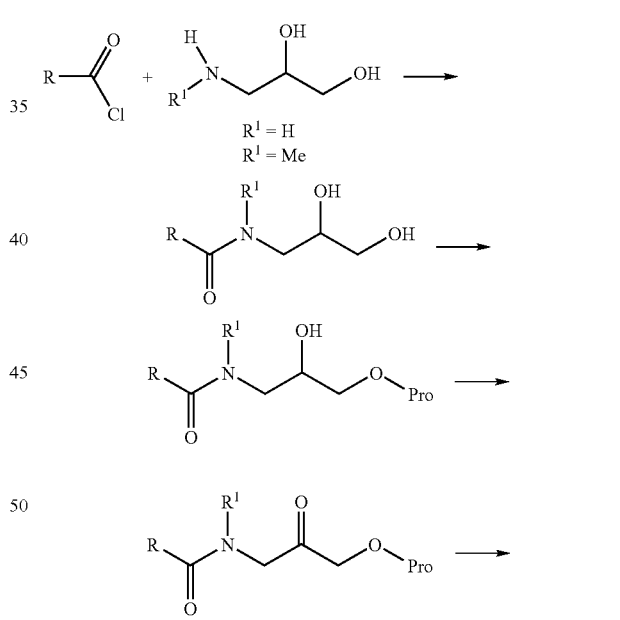

R = chromophore
R$^1$ = R
or R$^1$ ≠ R; R = H, Alk, Ar

The compounds of the formula I or II in which X=NR$^1$ can also be prepared starting from a halogenated precursor:

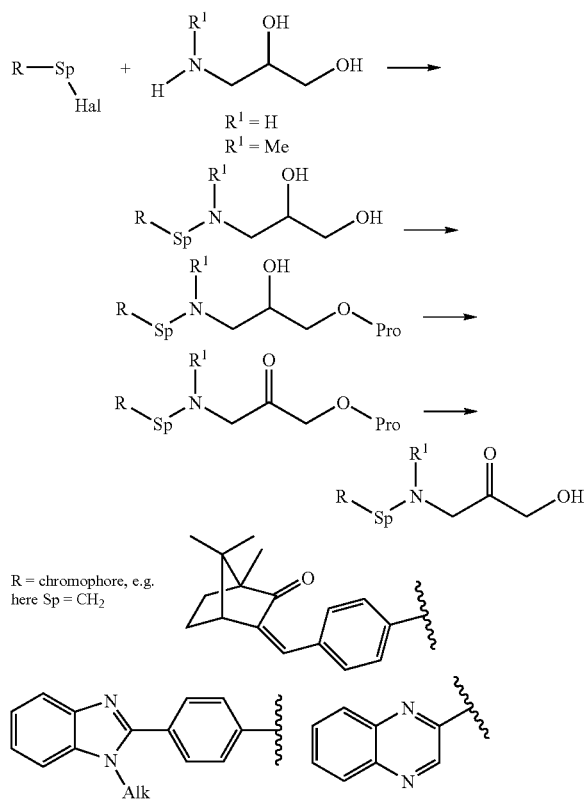

Correspondingly, the present invention also relates to a process for the preparation of compounds of the formula II where X stands for $NR^1$, in which an acid chloride $R-(CH_2)_n-C(=O)Cl$ or a compound R-Sp-Hal, where Hal stands for Cl, Br or I, is reacted with a compound

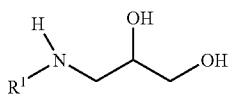

The present invention furthermore relates to compositions comprising a suitable vehicle, characterised in that the composition comprises 0.001 to 99% by weight of at least one compound of the formulae I and/or II or topically tolerated salts and/or derivatives thereof. One or more compounds of the formula I or II here are preferably present in the composition in amounts of 0.01 to 20% by weight, preferably 0.05 to 10% by weight and particularly preferably 0.1 to 5% by weight.

In a preferred embodiment of the present invention, the composition is a composition for protection of body cells against oxidative stress, in particular for reducing skin ageing, characterised in that it comprises one or more further antioxidants in addition to one or more compounds of the formula I or formula II.

There are many proven substances known from the specialist literature which can be used as antioxidants, for example amino acids (for example glycine, histidine, tyrosine, tryptophan) and derivatives thereof, imidazoles, (for example urocanic acid) and derivatives thereof, peptides, such as D,L-carnosine, D-carnosine, L-carnosine and derivatives thereof (for example anserine), carotinoids, carotenes (for example α-carotene, β-carotene, lycopene) and derivatives thereof, chlorogenic acid and derivatives thereof, lipoic acid and derivatives thereof (for example dihydrolipoic acid), aurothioglucose, propylthiouracil and other thiols (for example thioredoxin, glutathione, cysteine, cystamine and the glycosyl, N-acetyl, methyl, ethyl, propyl, amyl, butyl and lauryl, palmitoyl, oleyl, γ-linoleyl, cholesteryl and glyceryl esters thereof) and salts thereof, dilauryl thiodipropionate, distearyl thiodipropionate, thiodipropionic acid and derivatives thereof (esters, ethers, peptides, lipids, nucleotides, nucleosides and salts), and sulfoximine compounds (for example buthionine sulfoximines, homocysteine sulfoximine, buthionine sulfones, penta-, hexa- and heptathionine sulfoximine) in very low tolerated doses (for example pmol to µmol/kg), and also (metal) chelating agents, (for example α-hydroxy fatty acids, palmitic acid, phytic acid, lactoferrin), α-hydroxy acids (for example citric acid, lactic acid, malic acid), humic acid, bile acid, bile extracts, bilirubin, biliverdin, EDTA, EGTA and derivatives thereof, unsaturated fatty acids and derivatives thereof, vitamin C and derivatives (for example ascorbyl palmitate, magnesium ascorbyl phosphate, ascorbyl acetate), tocopherols and derivatives (for example vitamin E acetate), vitamin A and derivatives (for example vitamin A palmitate), and coniferyl benzoate of benzoin resin, rutinic acid and derivatives thereof, α-glycosyl rutin, ferulic acid, furfurylideneglucitol, carnosine, butylhydroxytoluene, butylhydroxyanisole, nordihydroguaiaretic acid, trihydroxybutyrophenone, quercetin, uric acid and derivatives thereof, mannose and derivatives thereof, zinc and derivatives thereof (for example ZnO, $ZnSO_4$), selenium and derivatives thereof (for example selenomethionine), stilbenes and derivatives thereof (for example stilbene oxide, trans-stilbene oxide).

Mixtures of antioxidants are likewise suitable for use in the cosmetic compositions according to the invention. Known and commercial mixtures are, for example, mixtures comprising, as active ingredients, lecithin, L-(+)-ascorbyl palmitate and citric acid (for example Oxynex® AP), natural tocopherols, L-(+)-ascorbyl palmitate, L-(+)-ascorbic acid and citric acid (for example Oxynex® K LIQUID), tocopherol extracts from natural sources, L-(+)-ascorbyl palmitate, L-(+)-ascorbic acid and citric acid (for example Oxynex® L LIQUID), DL-α-tocopherol, L-(+)-ascorbyl palmitate, citric acid and lecithin (for example Oxynex® LM) or butylhydroxytoluene (BHT), L-(+)-ascorbyl palmitate and citric acid (for example Oxynex® 2004). Antioxidants of this type are usually employed with compounds of the formula I or formula II in such compositions in ratios in the range from 1000:1 to 1:1000, preferably in amounts of 100:1 to 1:100.

The compositions according to the invention may comprise vitamins as further ingredients. The cosmetic compositions according to the invention preferably comprise vitamins and vitamin derivatives selected from vitamin A, vitamin A propionate, vitamin A palmitate, vitamin A acetate, retinol, vitamin B, thiamine chloride hydrochloride (vitamin $B_1$), riboflavin (vitamin $B_2$), nicotinamide, vitamin C (ascorbic acid), vitamin D, ergocalciferol (vitamin $D_2$), vitamin E, DL-α-tocopherol, tocopherol E acetate, tocopherol hydrogensuccinate, vitamin $K_1$, esculin (vitamin P active ingredient), thiamine (vitamin $B_1$), nicotinic acid (niacin), pyridoxine, pyridoxal, pyridoxamine, (vitamin $B_6$), pantothenic acid, biotin, folic acid and cobalamine (vitamin $B_{12}$), particularly preferably vitamin A palmitate, vitamin C and derivatives thereof, DL-α-tocopherol, tocopherol E acetate, nicotinic acid, pantothenic acid and biotin. Vitamins are usually employed here with compounds of the formula I or formula II in ratios in the range from 1000:1 to 1:1000, preferably in amounts of 100:1 to 1:100.

Of the phenols having an antioxidative action, the polyphenols, some of which are naturally occurring, are of particular interest for applications in the pharmaceutical, cosmetic or nutrition sector. For example, the flavonoids or bioflavonoids, which are principally known as plant dyes, frequently have an antioxidant potential. K. Lemanska, H. Szymusiak, B. Tyrakowska, R. Zielinski, I. M. C. M. Rietjens; Current Topics in Biophysics 2000, 24(2), 101-108, are concerned with effects of the substitution pattern of mono- and dihydroxyflavones. It is observed therein that dihydroxyflavones containing an OH group adjacent to the keto function or OH groups in the 3',4'- or 6,7- or 7,8-position have antioxidative properties, while other mono- and dihydroxyflavones in some cases do not have antioxidative properties.

Quercetin (cyanidanol, cyanidenolon 1522, meletin, sophoretin, ericin, 3,3',4',5,7-pentahydroxyflavone) is frequently mentioned as a particularly effective antioxidant (for example C. A. Rice-Evans, N. J. Miller, G. Paganga, Trends in Plant Science 1997, 2(4), 152-159). K. Lemanska, H. Szymusiak, B. Tyrakowska, R. Zielinski, A. E. M. F. Soffers, I. M. C. M. Rietjens; Free Radical Biology&Medicine 2001, 31(7), 869-881, are investigating the pH dependence of the antioxidant action of hydroxyflavones. Quercetin exhibits the greatest activity amongst the structures investigated over the entire pH range.

Suitable antioxidants are furthermore compounds of the formula III

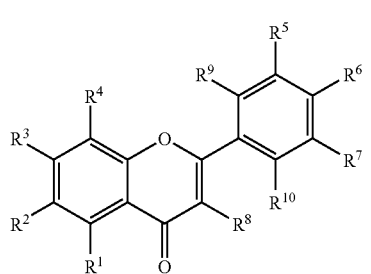

III where $R^1$ to $R^{10}$ may be identical or different and are selected from

H $OR^{11}$ straight-chain or branched $C_1$- to $C_{20}$-alkyl groups, straight-chain or branched $C_3$- to $C_{20}$-alkenyl groups, straight-chain or branched $C_1$- to $C_{20}$-hydroxyalkyl groups, where the hydroxyl group may be bonded to a primary or secondary carbon atom of the chain and furthermore the alkyl chain may also be interrupted by oxygen, and/or $C_3$- to $C_{10}$-cycloalkyl groups and/or $C_3$- to $C_{12}$-cycloalkenyl groups, where the rings may each also be bridged by —$(CH_2)_n$— groups, where n=1 to 3, where all $OR^{11}$, independently of one another, stand for

OH straight-chain or branched $C_1$- to $C_{20}$-alkoxy groups, straight-chain or branched $C_3$- to $C_{20}$-alkenyloxy groups, straight-chain or branched $C_1$- to $C_{20}$-hydroxyalkoxy groups, where the hydroxyl group(s) may be bonded to a primary or secondary carbon atom of the chain and furthermore the alkyl chain may also be interrupted by oxygen, and/or $C_3$- to $C_{10}$-cycloalkoxy groups and/or $C_3$- to $C_{12}$-cycloalkenyloxy groups, where the rings may each also be bridged by —$(CH_2)_n$— groups, where n=1 to 3, and/or mono- and/or oligoglycosyl radicals, with the proviso that at least 4 radicals from $R^1$ to $R^7$ stand for OH and that at least 2 pairs of adjacent —OH groups are present in the molecule, or $R^2$, $R^5$ and $R^6$ stand for OH and the radicals $R^1$, $R^3$, $R^4$ and $R^{7-10}$ stand for H, as described in German patent application DE-A 10244282.

Compositions which are preferred in accordance with the invention may also comprise further UV filters in addition to the compounds of the formula I or formula II.

On use of the dibenzoylmethane derivatives which are particularly preferred as UV-A filters in combination with the compounds of the formula I or formula II, an additional advantage arises: the UV-sensitive dibenzoylmethane derivatives are additionally stabilised by the presence of the compounds of the formula I or formula II. The present invention therefore furthermore relates to the use of the compounds of the formula I or formula II for the stabilisation of dibenzoylmethane derivatives in compositions.

In principle, all UV filters are suitable for combination with the compounds of the formula I or formula II according to the invention. Particular preference is given to UV filters whose physiological acceptability has already been demonstrated. Both for UVA and UVB filters, there are many proven substances known from the specialist literature, for example benzylidenecamphor derivatives, such as 3-(4'-methylbenzylidene)dl-camphor (for example Eusolex® 6300), 3-benzylidenecamphor (for example Mexoryl® SD), polymers of N-{(2 and 4)-[(2-oxoborn-3-ylidene)methyl]-benzyl}acrylamide (for example Mexoryl® SW), N,N,N-trimethyl-4-(2-oxoborn-3-ylidenemethyl)anilinium methylsulfate (for example Mexoryl® SK) or (2-oxoborn-3-ylidene)toluene-4-sulfonic acid (for example Mexoryl® SL), benzoyl- or dibenzoylmethanes, such as 1-(4-tert-butylphenyl)-3-(4-methoxyphenyl)propane-1,3-dione (for example Eusolex® 9020) or 4-isopropyldibenzoylmethane (for example Eusolex® 8020), benzophenones, such as 2-hydroxy-4-methoxybenzophenone (for example Eusolex® 4360) or 2-hydroxy-4-methoxybenzophenone-5-sulfonic acid and its sodium salt (for example Uvinul® MS-40), methoxycinnamic acid esters, such as octyl methoxycinnamate (for example Eusolex® 2292), isopentyl 4-methoxycinnamate, for example as a mixture of the isomers (for example Neo Heliopan® E 1000), salicylate derivatives, such as 2-ethylhexyl salicylate (for example Eusolex® OS), 4-isopropylbenzyl salicylate (for example Megasol®) or 3,3,5-trimethylcyclohexyl salicylate (for example Eusolex® HMS), 4-aminobenzoic acid and derivatives, such as 4-aminobenzoic acid, 2-ethylhexyl 4-(dimethylamino)benzoate (for example Eusolex® 6007), ethoxylated ethyl 4-aminobenzoate (for example Uvinul® P25), phenylbenzimidazolesulfonic acids, such as 2-phenylbenzimidazole-5-sulfonic acid and potassium, sodium and triethanolamine salts thereof (for example Eusolex® 232), 2,2-(1,4-phenylene)bisbenzimidazole-4,6-disulfonic acid and salts thereof (for example Neoheliopan® AP) or 2,2-(1,4-phenylene)bisbenzimidazole-6-sulfonic acid;

and further substances, such as 2-ethylhexyl 2-cyano-3,3-diphenylacrylate (for example Eusolex® OCR), 3.3'-(1,4-phenylenedimethylene)bis(7,7-dimethyl-2-oxo-bicyclo[2.2.1]-hept-1-ylmethanesulfonic acid and salts thereof (for example Mexoryl® SX) and 2,4,6-trianilino-(p-carbo-2'-ethylhexyl-1'-oxy)-1,3,5-triazine (for example Uvinul® T 150)

hexyl 2-(4-diethylamino-2-hydroxybenzoyl)benzoate (for example Uvinul®UVA Plus, BASF).

The compounds mentioned in the list should only be regarded as examples. It is of course also possible to use other UV filters.

These organic UV filters are generally incorporated into cosmetic formulations in an amount of 0.5 to 10 percent by weight, preferably 1-8%.

Further suitable organic UV filters are, for example,

-2-(2H-benzotriazol-2-yl)-4-methyl-6-(2-methyl-3-(1,3,3,3-tetramethyl-1-(trimethylsilyloxy)disiloxanyl)propyl)phenol (for example Silatrizole®), -2-ethylhexyl 4,4'-[(6-[4-((1,1-dimethylethyl)aminocarbonyl)phenylamino]-1,3,5-triazine-2,4-diyl)diimino]bis(benzoate) (for example Uvasorb® HEB), α-(trimethylsilyl)-ω-[trimethylsilyl)oxy]poly[oxy(dimethyl [and approximately 6% of methyl[2-[p-[2,2-bis(ethoxycarbonyl)vinyl]phenoxy]-1-methyleneethyl] and approximately 1.5% of methyl[3-[p-[2,2-bis(ethoxycarbonyl)vinyl])phenoxy)propenyl] and 0.1 to 0.4% of (methylhydrogen]silylene]] (n≈60) (CAS No. 207 574-74-1)

2.2'-methylenebis(6-(2H-benzotriazol-2-yl)-4-(1,1,3,3-tetramethylbutyl)phenol) (CAS No. 103 597-45-1)

2.2'-(1,4-phenylene)bis(1H-benzimidazole-4,6-disulfonic acid, monosodium salt) (CAS No. 180 898-37-7) and 2,4-bis{[4-(2-ethylhexyloxy)-2-hydroxy]phenyl}-6-(4-methoxyphenyl)-1,3,5-triazine (CAS No. 103 597-45-, 187 393-00-6).

2-ethylhexyl 4,4'-[(6-[4-((1,1-dimethylethyl)aminocarbonyl)phenylamino]-1,3,5-triazine-2,4-diyl)diimino]bis(benzoate) (for example Uvasorb® HEB), Further suitable UV filters are also methoxyflavones corresponding to the earlier German patent application DE-A 10232595.

Organic UV filters are generally incorporated into cosmetic formulations in an amount of 0.5 to 20 percent by weight, preferably 1-15%.

Conceivable inorganic UV filters are those from the group of the titanium dioxides, such as, for example, coated titanium dioxide (for example Eusolex® T-2000, Eusolex® T-AQUA, Eusolex® T-AVO), zinc oxides (for example Sachtotec®), iron oxides or also cerium oxides. These inorganic UV filters are generally incorporated into cosmetic compositions in an amount of 0.5 to 20 percent by weight, preferably 2-10%.

Preferred compounds having UV-filtering properties are 3-(4'-methylbenzylidene)dl-camphor, 1-(4-tert-butylphenyl)-3-(4-methoxyphenyl)propane-1,3-dione, 4-isopropyldibenzoylmethane, 2-hydroxy-4-methoxybenzophenone, octyl methoxycinnamate, 3,3,5-trimethylcyclohexyl salicylate, 2-ethylhexyl 4-(dimethylamino)benzoate, 2-ethylhexyl 2-cyano-3,3-diphenylacrylate, 2-phenylbenzimidazole-5-sulfonic acid and potassium, sodium and triethanolamine salts thereof.

The protective action against damaging effects of UV radiation can be optimised by combining one or more compounds of the formula I or formula II with further UV filters.

Optimised compositions may comprise, for example, the combination of UVA with UV filters of the formula I or II. This combination gives rise to broad-band protection, which can be supplemented by the addition of inorganic UV filters, such as titanium dioxide microparticles.

All the said UV filters can also be employed in encapsulated form. It is also possible to employ the compounds of the formula I or II in encapsulated form here. However, it is preferred here to employ the skin-adherent compounds of the formula I in unencapsulated form. In particular, it is advantageous to employ organic UV filters in encapsulated form. In detail, the following advantages arise:

The hydrophilicity of the capsule wall can be set independently of the solubility of the UV filter. Thus, for example, it is also possible to incorporate hydrophobic UV filters into purely aqueous compositions. In addition, the oily impression on application of the composition comprising hydrophobic UV filters, which is frequently regarded as unpleasant, is suppressed.

Certain UV filters, in particular dibenzoylmethane derivatives, exhibit only reduced photostability in cosmetic compositions. Encapsulation of these filters or compounds which impair the photostability of these filters, such as, for example, cinnamic acid derivatives, enables the photostability of the entire composition to be increased.

Skin penetration by organic UV filters and the associated potential for irritation on direct application to the human skin is repeatedly being discussed in the literature. The encapsulation of the corresponding substances which is proposed here suppresses this effect.

In general, encapsulation of individual UV filters or other ingredients enables composition problems caused by the interaction of individual composition constituents with one another, such as crystallisation processes, precipitation and agglomerate formation, to be avoided since the interaction is suppressed.

It is therefore preferred in accordance with the invention for one or more of the above-mentioned UV filters and/or the compounds of the formula I or II to be in encapsulated form. It is advantageous here for the capsules to be so small that they cannot be viewed with the naked eye. In order to achieve the above-mentioned effects, it is furthermore necessary for the capsules to be sufficiently stable and the encapsulated active ingredient (UV filter) only to be released to the environment to a small extent, or not at all.

Suitable capsules can have walls of inorganic or organic polymers. For example, U.S. Pat. No. 6,242,099 B1 describes the production of suitable capsules with walls of chitin, chitin derivatives or polyhydroxylated polyamines. Capsules which can particularly preferably be employed in accordance with the invention have walls which can be obtained by a sol-gel process, as described in the applications WO 00/09652, WO 00/72806 and WO 00/71084. Preference is again given here to capsules whose walls are built up from silica gel (silica; undefined silicon oxide hydroxide). The production of corresponding capsules is known to the person skilled in the art, for example from the cited patent applications, whose contents expressly also belong to the subject-matter of the present application.

The capsules in compositions according to the invention are preferably present in amounts which ensure that the encapsulated UV filters are pre-sent in the composition in the above-indicated amounts.

In accordance with the invention, it may be preferred here for the compositions to comprise active compounds which simplify skin penetration, so-called "penetration enhancers". These active compounds which simplify skin penetration can have the effect that the skin-adhering UV filters according to the invention penetrate into deeper skin layers, which are only repelled after a considerable time and thus provide particularly long-lasting UV protection. Suitable enhancers are various substances described in the literature, which are divided into three classes (Lambert W J, Kudlar R J, Hollard J M, Curry J T (1993) Int J Pharm, 45:181): solvents comprising H-bond acceptors, simple fatty acids and alcohols and weakly surface-active substances. A chemical classification distinguishes between alcohols, sulfoxides, fatty acids, fatty acid esters, polyols, surfactants, terpenes and organic acids (Kalbitz J, Neubert R, Wohirab W (1996) Modulation der Wirkstoffpenetration in die Haut [Modulation of Active Compound Penetration into the Skin]. *Pharmazie,* 51:619-637). Ethanol and 1,2-propanediol are amongst the active compounds which simplify skin penetration that are particularly preferred in accordance with the invention.

The compositions according to the invention may in addition comprise further conventional skin-protecting or skin-care active ingredients. These may in principle be any active ingredients known to the person skilled in the art.

It may furthermore be preferred for the composition according to the invention to comprise at least one repellent, where the repellent is preferably selected from N,N-diethyl-3-methylbenzamide, ethyl 3-(acetylbutylamino)-propionate, dimethyl phthalate, butopyronoxyl, 2,3,4,5-bis(2-butylene)-tetrahydro-2-furaldehyde, N,N-diethylcaprylamide, N,N-diethylbenzamide, o-chloro-N,N-diethylbenzamide, dimethyl carbate, di-n-propyl isocinchomeronate, 2-ethylhexane-1,3-diol, N-octylbicycloheptenedicarboximide, piperonyl butoxide, 1-(2-methylpropoxycarbonyl)-2-(hydroxyethyl)piperidine, or mixtures thereof, where it is particularly preferably selected from N,N-diethyl-3-methylbenzamide, ethyl 3-(acetylbutylamino)propionate 1-(2-methylpropoxycarbonyl)-2-(hydroxyethyl)piperidine, or mixtures thereof.

The compositions according to the invention which comprise repellents are preferably insect repellents. Insect repellents are available in the form of solutions, gels, sticks, rollers, pump sprays and aerosol sprays, with solutions and sprays forming the majority of the commercially available products. The basis for these two product forms is usually formed by alcoholic or aqueous/alcoholic solutions with addition of fatting substances and slight perfuming.

Particularly preferred active ingredients are, for example, also so-called compatible solutes. These are substances which are involved in the osmoregulation of plants or microorganisms and can be isolated from these organisms. The generic term compatible solutes here also encompasses the osmolytes described in German patent application DE-A-10133202. Suitable osmolytes are, for example, the polyols, methylamine compounds and amino acids and the respective precursors thereof. For the purposes of German patent application DE-A-10133202, osmolytes are taken to mean, in particular, substances from the group of the polyols, such as, for example, myo-inositol, mannitol or sorbitol and/or one or more of the osmolytically active substances mentioned below:

taurine, choline, betaine, phosphorylcholine, glycerophosphorylcholines, glutamine, glycine, α-alanine, glutamate, aspartate, proline, and taurine. Precursors of these substances are, for example, glucose, glucose polymers, phosphatidylcholine, phosphatidylinositol, inorganic phosphates, proteins, peptides and polyamino acids. Precursors are, for example, compounds which are converted into osmolytes by metabolic steps.

In accordance with the invention, compatible solutes are preferably substances selected from the group consisting of pyrimidinecarboxylic acids (such as ectoine and hydroxyectoine), proline, betaine, glutamine, cyclic diphosphoglycerate, N-acetylornithine, trimethylamine N-oxide, di-myo-inositol phosphate (DIP), cyclic 2,3-diphosphoglycerate (cDPG), 1,1-diglycerol phosphate (DGP), β-mannosyl glycerate (firoin), β-mannosylglyceramide (firoin A) or/and dimannosyl diinositol phosphate (DMIP) or an optical isomer, derivative, for example an acid, or a salt or ester of these compounds, or combinations thereof.

Of the pyrimidinecarboxylic acids, particular mention should be made here of ectoine ((S)-1,4,5,6-tetrahydro-2-methyl-4-pyrimidinecarboxylic acid) and hydroxyectoine ((S,S)-1,4,5,6-tetrahydro-5-hydroxy-2-methyl-4-pyrimidinecarboxylic acid) and derivatives thereof. These compounds stabilise enzymes and other biomolecules in aqueous solutions and organic solvents. Furthermore, they stabilise, in particular, enzymes against denaturing conditions, such as salts, extreme pH values, surfactants, urea, guanidinium chloride and other compounds.

Ectoine and ectoine derivatives, such as hydroxyectoine, can advantageously be used in medicaments. In particular, hydroxyectoine can be employed for the preparation of a medicament for the treatment of skin diseases. Other areas of application of hydroxyectoine and other ectoine derivatives are typically in areas in which, for example, trehalose is used as additive. Thus, ectoine derivatives, such as hydroxyectoine, can be used as protectant in dried yeast and bacteria cells. Pharmaceutical products, such as non-glycosylated, pharmaceutically active peptides and proteins, for example t-PA, can also be protected with ectoine or its derivatives.

Of the cosmetic applications, particular mention should be made of the use of ectoine and ectoine derivatives for the care of aged, dry or irritated skin. Thus, European patent application EP-A-0 671 161 describes, in particular, that ectoine and hydroxyectoine are employed in cosmetic compositions, such as powders, soaps, surfactant-containing cleansing products, lipsticks, rouge, make-ups, care creams and sunscreen compositions.

Preference is given here to the use of a tetrahydropyrimidinecarboxylic acid of the following formula IV

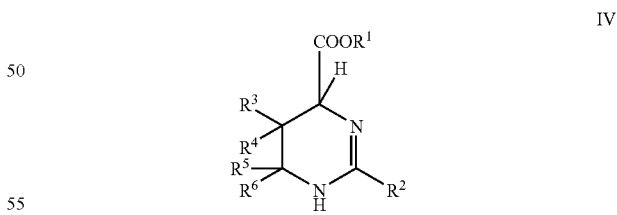

in which $R^1$ is a radical H or $C_{1-8}$-alkyl, $R^2$ is a radical H or $C_{1-4}$-alkyl, and $R^3$, $R^4$, $R^5$ and $R^6$ are each, independently of one another, a radical from the group H, OH, $NH_2$ and $C_{1-4}$-alkyl. Preference is given to the use of pyrimidinecarboxylic acids in which $R^2$ is a methyl or ethyl group, and $R^1$ or $R^5$ and $R^6$ are H. Particular preference is given to the use of the pyrimidinecarboxylic acids ectoine ((S)-1,4,5,6-tetrahydro-2-methyl-4-pyrimidinecarboxylic acid) and hydroxyectoine ((S,S)-1,4,5,6-tetrahydro-5-hydroxy-2-methyl-4-pyrimidinecarboxylic acid). The compositions according to the invention preferably comprise pyrimidinecarboxylic acids of this type in amounts of up to 15% by weight. The pyrimidinecarboxylic acids are preferably employed here in ratios of from 100:1 to 1:100 with respect to the compounds of the formula I, with ratios in the range from 1:10 to 10:1 being particularly preferred.

It is particularly preferred in accordance with the invention if the compatible solutes are selected from di-myo-inositol phosphate (DIP), cyclic 2,3-diphosphoglycerate (cDPG), 1,1-diglycerol phosphate (DGP), β-mannosyl glycerate (firoin), β-mannosylglyceramide (firoin-A) or/and di-mannosyl diinositol phosphate (DMIP), ectoine, hydroxyectoine or mixtures thereof.

Of the aryl oximes that are likewise preferably employed, preference is given to the use of 2-hydroxy-5-methyllaurophenone oxime, which is also known as HMLO, LPO or F5. Its suitability for use in cosmetic compositions is disclosed, for example, in DE-A-41 16 123. Compositions which comprise 2-hydroxy-5-methyllaurophenone oxime are accordingly suitable for the treatment of skin diseases which are accompanied by inflammation. It is known that compositions of this type can be used, for example, for the therapy of psoriasis, various forms of eczema, irritative and toxic dermatitis, UV dermatitis and further allergic and/or inflammatory diseases of the skin and integumentary appendages. Compositions according to the invention which, in addition to the compound of the formula I, additionally comprise an aryl oxime, preferably 2-hydroxy-5-methyllaurophenone oxime, exhibit surprising antiinflammatory suitability. The compositions here preferably comprise 0.01 to 10% by weight of the aryl oxime, it being particularly preferred for the composition to comprise 0.05 to 5% by weight of aryl oxime.

In a further, likewise preferred embodiment of the present invention, the composition according to the invention comprises at least one self-tanning agent.

Advantageous self-tanning agents which can be employed are, inter alia:

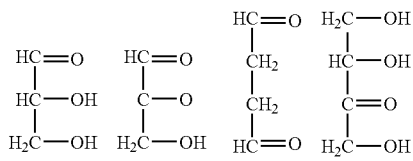

glycerolaldehyde   hydroxymethylglyoxal   succinaldehyde
erythrulose

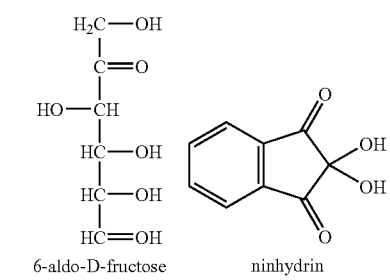

6-aldo-D-fructose         ninhydrin

Mention should also be made of 5-hydroxy-1,4-naphthoquinone (juglone), which is extracted from the shells of fresh walnuts

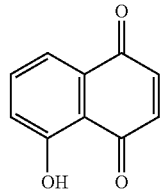

5-hydroxy-1,4-naphthoquinone (juglone)
and 2-hydroxy-1,4-naphthoquinone (lawsone), which occurs in henna leaves.

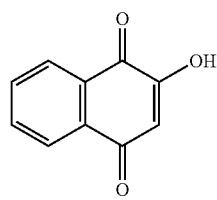

2-hydroxy-1,4-naphthoquinone (lawsone)

Very particular preference is given to 1,3-dihydroxyacetone (DHA), a trifunctional sugar which occurs in the human body, and derivatives thereof.

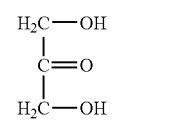

1,3-dihydroxyacetone (DHA)

Furthermore, the compositions according to the invention may also comprise dyes and coloured pigments. The dyes and coloured pigments can be selected from the corresponding positive list in the German Cosmetics Regulation or the EC list of cosmetic colorants. In most cases, they are identical with the dyes approved for foods. Advantageous coloured pigments are, for example, titanium dioxide, mica, iron oxides (for example $Fe_2O_3$, $Fe_3O_4$, $FeO(OH)$) and/or tin oxide. Advantageous dyes are, for example, carmine, Berlin Blue, Chromium Oxide Green, Ultramarine Blue and/or Manganese Violet. It is particularly advantageous to select the dyes and/or coloured pigments from the following list. The Colour Index numbers (CINs) are taken from the Rowe Colour Index, 3rd Edition, Society of Dyers and Colourists, Bradford, England, 1971.

| Chemical or other name | CIN | Colour |
|---|---|---|
| Pigment Green | 10006 | green |
| Acid Green 1 | 10020 | green |
| 2,4-Dinitrohydroxynaphthalene-7-sulfonic acid | 10316 | yellow |
| Pigment Yellow 1 | 11680 | yellow |
| Pigment Yellow 3 | 11710 | yellow |
| Pigment Orange 1 | 11725 | orange |
| 2,4-Dihydroxyazobenzene | 11920 | orange |
| Solvent Red 3 | 12010 | red |
| 1-(2'-chloro-4'-nitro-1'-phenylazo)-2-hydroxynaphthalene | 12085 | red |
| Pigment Red 3 | 12120 | red |
| Ceres Red; Sudan Red; Fat Red G | 12150 | red |
| Pigment Red 112 | 12370 | red |
| Pigment Red 7 | 12420 | red |
| Pigment Brown 1 | 12480 | brown |
| 4-(2'-Methoxy-5'sulfonyldiethylamide-1'-phenylazo)-3-hydroxy-5''-chloro-2'',4''-dimethoxy2-naphthanilide | 12490 | red |
| Disperse Yellow 16 | 12700 | yellow |
| 1-(4-Sulfo-1-phenylazo)-4-aminobenzene-5-sulfonic acid | 13015 | yellow |
| 2,4-Dihydroxyazobenzene-4'-sulfonic acid | 14270 | orange |
| 2-(2,4-Dimethylphenylazo-5-sulfonyl)-1-hydroxynaphthalene-4-sulfonic acid | 14700 | red |
| 2-(4-Sulfo-1-naphthylazo)-1-naphthol-4-sulfonic acid | 14720 | red |
| 2-(6-Sulfo-2,4-xylylazo)-1-naphthol-5-sulfonic acid | 14815 | red |
| 1-(4'-Sulfophenylazo)-2-hydroxynaphthalene | 15510 | orange |
| 1-(2-Sulfonyl-4-chloro-5-carboxy-1-phenylazo)-2-hydroxynaphthalene | 15525 | red |
| 1-(3-Methylphenylazo-4-sulfonyl)-2-hydroxynaphthalene | 15580 | red |
| 1-(4',(8')-Sulfonylnaphthylazo)-2-hydroxynaphthalene | 15620 | red |
| 2-Hydroxy-1,2'-azonaphthalene-1'-sulfonic acid | 15630 | red |
| 3-Hydroxy-4-phenylazo-2-naphthalenecarboxylic acid | 15800 | red |
| 1-(2-Sulfo-4-methyl-1-phenylazo)-2-naphthalenecarboxylic acid | 15850 | red |
| 1-(2-Sulfo-4-methyl-5-chloro-1-phenylazo)-2-hydroxynaphthalene-3-carboxylic acid | 15865 | red |
| 1-(2-Sulfo-1-naphthylazo)-2-hydroxynaphthalene-3-carboxylic acid | 15880 | red |
| 1-(3-Sulfo-1-phenylazo)-2-naphthol-6-sulfonic acid | 15980 | orange |
| 1-(4-Sulfo-1-phenylazo)-2-naphthol-6-sulfonic acid | 15985 | yellow |
| Allura Red | 16035 | red |
| 1-(4-Sulfo-1-naphthylazo)-2-naphthol-3,6-disulfonic acid | 16185 | red |
| Acid Orange 10 | 16230 | orange |
| 1-(4-Sulfo-1-naphthylazo)-2-naphthol-6,8-disulfonic acid | 16255 | red |
| 1-(4-Sulfo-1-naphthylazo)-2-naphthol-3,6,8-trisulfonic acid | 16290 | red |
| 8-Amino-2-phenylazo-1-naphthol-3,6-dinsulfonic acid | 17200 | red |
| Acid Red 1 | 18050 | red |
| Acid Red 155 | 18130 | red |
| Acid Yellow 121 | 18690 | yellow |
| Acid Red 180 | 18736 | red |
| Acid Yellow 11 | 18820 | yellow |
| Acid Yellow 17 | 18965 | yellow |
| 4-(4-Sulfo-1-phenylazo)-1-(4-sulfophenyl)-5-hydroxy-pyrazolone-3-carboxylic acid | 19140 | yellow |
| Pigment Yellow 16 | 20040 | yellow |
| 2,6-(4'-Sulfo-2'',4''-dimethyl)bisphenylazo)1,3-dihydroxy-benzene | 20170 | orange |
| Acid Black 1 | 20470 | black |
| Pigment Yellow 13 | 21100 | yellow |
| Pigment Yellow 83 | 21108 | yellow |
| Solvent Yellow | 21230 | yellow |
| Acid Red 163 | 24790 | red |
| Acid Red 73 | 27290 | red |
| 2-[4'-(4''-Sulfo-1''-phenylazo)-7'-sulfo-1'-naphthylazo]-1-hydroxy-7-aminonaphthalene-3,6-disulfonic acid | 27755 | black |
| 4-[4''-Sulfo-1''-phenylazo)-7'-sulfo-1'-naphthylazo]-1-hydroxy-8-acetylaminonaphthalene-3,5-disulfonic acid | 28440 | black |
| Direct Orange 34, 39, 44, 46, 60 | 40215 | orange |
| Food Yellow | 40800 | orange |
| trans-β-Apo-8'-carotene aldehyde ($C_{30}$) | 40820 | orange |
| trans-Apo-8'-carotinic acid ($C_{30}$) ethyl ester | 40850 | orange |
| Canthaxanthine | 40850 | orange |
| Acid Blue 1 | 42045 | blue |
| 2,4-Disulfo-5-hydroxy-4'-4''-bis(diethylamino)triphenylcarbinol | 42051 | blue |
| 4-[(-4-N-Ethyl-p-sulfobenzylamino)phenyl-(4-hydroxy-2-sulfophenyl)(methylene)-1-(N-ethylN-p-sulfobenzyl)-2,5-cyclohexadienimine] | 42053 | green |
| Acid Blue 7 | 42080 | blue |

-continued

| Chemical or other name | CIN | Colour |
|---|---|---|
| (N-Ethyl-p-sulfobenzylamino)phenyl-(2-sulfophenyl)-methylene-(N-ethyl-N-p-sulfobenzyl)$\Delta^{2,5}$-cyclohexadienimine | 42090 | blue |
| Acid Green 9 | 42100 | green |
| Diethyldisulfobenzyldi-4-amino-2-chlorodi-2-methylfuchsonimmonium salt | 42170 | green |
| Basic Violet 14 | 42510 | violet |
| Basic Violet 2 | 42520 | violet |
| 2'-Methyl-4'-(N-ethyl-N-m-sulfobenzyl)amino-4"-(N-diethyl)amino-2-methyl-N-ethyl-N-m-sulfobenzyl-fuchsonimmonium salt | 42735 | blue |
| 4'-(N-Dimethyl)amino-4"-(N-phenyl)aminonaphtho-N-dimethylfuchsonimmonium salt | 44045 | blue |
| 2-Hydroxy-3,6-disulfo-4,4'-bisdimethylaminonaphtho-fuchsonimmonium salt | 44090 | green |
| Acid Red 52 | 45100 | red |
| 3-(2'-Methylphenylamino)-6-(2'-methyl-4'-sulfophenylamino)-9-(2''-carboxyphenyl)xanthenium salt | 45190 | violet |
| Acid Red 50 | 45220 | red |
| Phenyl-2-oxyfluorone-2-carboxylic acid | 45350 | yellow |
| 4,5-Dibromofluorescein | 45370 | orange |
| 2,4,5,7-Tetrabromofluorescein | 45380 | red |
| Solvent Dye | 45396 | orange |
| Acid Red 98 | 45405 | red |
| 3',4',5',6'-Tetrachloro-2,4,5,7-tetrabromofluorescein | 45410 | red |
| 4,5-Diiodofluorescein | 45425 | red |
| 2,4,5,7-Tetraiodofluorescein | 45430 | red |
| Quinophthalone | 47000 | yellow |
| Quinophthalonedisulfonic acid | 47005 | yellow |
| Acid Violet 50 | 50325 | violet |
| Acid Black 2 | 50420 | black |
| Pigment Violet 23 | 51319 | violet |
| 1,2-Dioxyanthraquinone, calcium/aluminium complex | 58000 | red |
| 3-Oxypyrene-5,8,10-trisulfonic acid | 59040 | green |
| 1-Hydroxy-4-N-phenylaminoanthraquinone | 60724 | violet |
| 1-Hydroxy-4-(4'-methylphenylamino)anthraquinone | 60725 | violet |
| Acid Violet 23 | 60730 | violet |
| 1,4-Di(4'-methylphenylamino)anthraquinone | 61565 | green |
| 1,4-Bis(o-sulfo-p-toluidino)anthraquinone | 61570 | green |
| Acid Blue 80 | 61585 | blue |
| Acid Blue 62 | 62045 | blue |
| N,N'-Dihydro-1,2,1',2'-anthraquinonazine | 69800 | blue |
| Vat Blue 6; Pigment Blue 64 | 69825 | blue |
| Vat Orange 7 | 71105 | orange |
| Indigo | 73000 | blue |
| Indigodisulfonic acid | 73015 | blue |
| 4,4'-Dimethyl-6,6'-dichlorothioindigo | 73360 | red |
| 5,5'Dichloro-7,7'-dimethylthioindigo | 73385 | violet |
| Quinacridone Violet 19 | 73900 | violet |
| Pigment Red 122 | 73915 | red |
| Pigment Blue 16 | 74100 | blue |
| Phthalocyanines | 74160 | blue |
| Direct Blue 86 | 74180 | blue |
| chlorinated phthalocyanines | 74260 | green |
| Natural Yellow 6, 19; Natural Red 1 | 75100 | yellow |
| Bixin, Nor-Bixin | 75120 | orange |
| Lycopene | 75125 | yellow |
| trans-alpha-, -beta- or -gamma-Carotene | 75130 | orange |
| Keto and/or hydroxyl derivatives of carotene | 75135 | yellow |
| Guanine or pearlescent agent | 75170 | white |
| 1,7-Bis(4-hydroxy-3-methoxyphenyl)1,6-heptadiene-3,5-dione | 75300 | yellow |
| Complex salt (Na, Al, Ca) of carminic acid | 75470 | red |
| chlorophyll a and b; copper compounds of chlorophylls and chlorophyllines | 75810 | green |
| Aluminium | 77000 | white |
| Aluminium hydroxide | 77002 | white |
| Water-containing aluminium silicates | 77004 | white |
| Ultramarine | 77007 | blue |
| Pigment Red 101 and 102 | 77015 | red |
| Barium sulfate | 77120 | white |
| Bismuth oxychloride and mixtures thereof with mica | 77163 | white |
| Calcium carbonate | 77220 | white |
| Calcium sulfate | 77231 | white |
| Carbon | 77266 | black |
| Pigment Black 9 | 77267 | black |
| Carbo medicinalis vegetabilis | 77268:1 | black |

-continued

| Chemical or other name | CIN | Colour |
|---|---|---|
| Chromium oxide | 77288 | green |
| Chromium oxide, water-containing | 77278 | green |
| Pigment Blue 28, Pigment Green 14 | 77346 | green |
| Pigment Metal 2 | 77400 | brown |
| Gold | 77480 | brown |
| Iron oxides and hydroxides | 77489 | orange |
| Iron oxide | 77491 | red |
| Iron oxide hydrate | 77492 | yellow |
| Iron oxide | 77499 | black |
| Mixtures of iron(II) and iron(III) hexacyanoferrate | 77510 | blue |
| Pigment White 18 | 77713 | white |
| Manganese ammonium diphosphate | 77742 | violet |
| Manganese phosphate; $Mn_3(PO_4)_2 \cdot 7\ H_2O$ | 77745 | red |
| Silver | 77820 | white |
| Titanium dioxide and mixtures thereof with mica | 77891 | white |
| Zinc oxide | 77947 | white |
| 6,7-Dimethyl-9-(1'-D-ribityl)isoalloxazine, lactoflavin | | yellow |
| Sugar dye | | brown |
| Capsanthin, capsorubin | | orange |
| Betanin | | red |
| Benzopyrylium salts, anthocyans | | red |
| Aluminium, zinc, magnesium and calcium stearate | | white |
| bromothymol Blue | | blue |

It may furthermore be favourable to select, as dye, one or more sub-stances from the following group:

2,4-dihydroxyazobenzene, 1-(2'-chloro-4'-nitro-1'phenylazo)-2-hydroxynaphthalene, Ceres Red, 2-(4-sulfo-1-naphthylazo)-1-naphthol-4-sulfonic acid, the calcium salt of 2-hydroxy-1,2'-azonaphthalene-1'-sulfonic acid, the calcium and barium salts of 1-(2-sulfo-4-methyl-1-phenylazo)-2-naphthylcarboxylic acid, the calcium salt of 1-(2-sulfo-1-naphthylazo)-2-hydroxynaphthalene-3-carboxylic acid, the aluminium salt of 1-(4-sulfo-1-phenylazo)-2-naphthol-6-sulfonic acid, the aluminium salt of 1-(4-sulfo-1-naphthylazo)-2-naphthol-3,6-disulfonic acid, 1-(4-sulfo-1-naphthylazo)-2-naphthol-6,8-disulfonic acid, the aluminium salt of 4-(4-sulfo-1-phenylazo)-2-(4-sulfophenyl)-5-(big blank)pyrazolone-3-carboxylic acid, the aluminium and zirconium salts of 4,5-dibromofluorescein, the aluminium and zirconium salts of 2,4,5,7-tetrabromofluorescein, 3',4',5',6'-tetrachloro-2,4,5,7-tetrabromofluorescein and its aluminium salt, the aluminium salt of 2,4,5,7-tetraiodofluorescein, the aluminium salt of quinophthalonedisulfonic acid, the aluminium salt of indigodisulfonic acid, red and black iron oxide (CIN: 77 491 (red) and 77 499 (black)), iron oxide hydrate (CIN: 77492), manganese ammonium diphosphate and titanium dioxide.

Also advantageous are oil-soluble natural dyes, such as, for example, paprika extract, β-carotene or cochineal.

Also advantageous for the purposes of the present invention are gel creams comprising pearlescent pigments. Particular preference is given to the types of pearlescent pigment listed below:

1. Natural pearlescent pigments, such as, for example,
    1. "pearl essence" (guanine/hypoxanthine mixed crystals from fish scales) and
    2. "mother-of-pearl" (ground mussel shells)
    3.
2. Monocrystalline pearlescent pigments, such as, for example, bismuth oxychloride (BiOCl)
3. Layered substrate pigments: for example mica/metal oxide The basis for pearlescent pigments is formed by, for example, pulverulent pigments or castor oil dispersions of bismuth oxychloride and/or titanium dioxide as well as bismuth oxychloride and/or titanium dioxide on mica. The lustre pigment listed under CIN 77163, for example, is particularly advantageous.

Also advantageous are, for example, the following pearlescent pigment types based on mica/metal oxide:

| Group | Coating/layer thickness | Colour |
|---|---|---|
| Silver-white pearlescent pigments | $TiO_2$: 40-60 nm | silver |
| Interference pigments | $TiO_2$: 60-80 nm | yellow |
| | $TiO_2$: 80-100 nm | red |
| | $TiO_2$: 100-140 nm | blue |
| | $TiO_2$: 120-160 nm | green |
| Coloured lustre pigments | $Fe_2O_3$ | bronze |
| | $Fe_2O_3$ | copper |
| | $Fe_2O_3$ | red |
| | $Fe_2O_3$ | red-violet |
| | $Fe_2O_3$ | red-green |
| | $Fe_2O_3$ | black |
| Combination pigments | $TiO_2/Fe_2O_3$ | gold shades |
| | $TiO_2/Cr_2O_3$ | green |
| | $TiO_2$/Berlin Blue | dark blue |

Particular preference is given to, for example, the pearlescent pigments available from Merck under the trade names Timiron, Colorona or Dichrona.

The list of the said pearlescent pigments is of course not intended to be limiting. Pearlescent pigments which are advantageous for the purposes of the present invention can be obtained by numerous routes known per se. For example, other substrates apart from mica can also be coated with further metal oxides, such as, for example, silica and the like. For example, $TiO_2$— and $Fe_2O_3$-coated $SiO_2$ particles ("Ronasphere" grades), which are marketed by Merck and are particularly suitable for the optical reduction of fine wrinkles, are advantageous.

It may additionally be advantageous to completely omit a substrate such as mica. Particular preference is given to pearlescent pigments prepared using $SiO_2$. Such pigments, which may additionally also have goniochromatic effects, are available, for example, from BASF under the trade name Sicopearl Fantastico.

It may also be advantageous to employ Engelhard/Mearl pigments based on calcium sodium borosilicate coated with titanium dioxide. These are available under the name Reflecks. Due to their particle size of 40-80 μm, they have a glitter effect in addition to the colour.

Also particularly advantageous are effect pigments available from Flora Tech under the trade name Metasomes Standard/Glitter in various colours (yellow, red, green, blue). The glitter particles here are in the form of mixtures with various assistants and dyes (such as, for example, the dyes with the Colour Index (CI) numbers 19140, 77007, 77289, 77491).

The dyes and pigments can be in individual form or in the form of a mixture and mutually coated with one another, with different colour effects generally being caused by different coating thicknesses. The total amount of dyes and colouring pigments is advantageously selected from the range from, for example, 0.1% by weight to 30% by weight, preferably 0.5 to 15% by weight, in particular 1.0 to 10% by weight, in each case based on the total weight of the compositions.

All compounds or components which can be used in the compositions are either known or commercially available or can be synthesised by known processes.

One or more compounds of the formula I or II can be incorporated into cosmetic or dermatological compositions in the customary manner. Suitable compositions are those for external use, for example in the form of a cream, lotion or gel or as a solution which can be sprayed onto the skin. Suitable for internal use are administration forms such as capsules, coated tablets, powders, tablets or solutions.

Use forms of the compositions according to the invention that may be mentioned are, for example, solutions, suspensions, emulsions, PIT emulsions, pastes, ointments, gels, creams, lotions, powders, soaps, surfactant-containing cleansing preparations, oils, aerosols and sprays. Examples of other use forms are sticks, shampoos and shower compositions. Any desired customary vehicles, assistants and, if desired, further active ingredients may be added to the composition.

Preferred assistants originate from the group of the preservatives, antioxidants, stabilisers, solubilisers, vitamins, colorants and odour improvers.

Ointments, pastes, creams and gels may comprise the customary vehicles, for example animal and vegetable fats, waxes, paraffins, starch, tragacanth, cellulose derivatives, polyethylene glycols, silicones, bentonites, silica, talc and zinc oxide, or mixtures of these substances.

Powders and sprays may comprise the customary vehicles, for example lactose, talc, silica, aluminium hydroxide, calcium silicate and polyamide powder, or mixtures of these substances. Sprays may additionally comprise the customary propellants, for example chlorofluorocarbons, propane/butane or dimethyl ether.

Solutions and emulsions may comprise the customary vehicles, such as solvents, solubilisers and emulsifiers, for example water, ethanol, isopropanol, ethyl carbonate, ethyl acetate, benzyl alcohol, benzyl benzoate, propylene glycol, 1,3-butyl glycol, oils, in particular cottonseed oil, peanut oil, wheatgerm oil, olive oil, castor oil and sesame oil, glycerol fatty acid esters, polyethylene glycols and fatty acid esters of sorbitan, or mixtures of these substances.

Suspensions may comprise the customary vehicles, such as liquid diluents, for example water, ethanol or propylene glycol, suspending agents, for example ethoxylated isostearyl alcohols, polyoxyethylene sorbitol esters and polyoxyethylene sorbitan esters, microcrystalline cellulose, aluminium metahydroxide, bentonite, agar-agar and tragacanth, or mixtures of these substances.

Soaps may comprise the customary vehicles, such as alkali metal salts of fatty acids, salts of fatty acid monoesters, fatty acid protein hydrolysates, isethionates, lanolin, fatty alcohol, vegetable oils, plant extracts, glycerol, sugars, or mixtures of these substances.

Surfactant-containing cleansing products may comprise the customary vehicles, such as salts of fatty alcohol sulfates, fatty alcohol ether sulfates, sulfosuccinic acid monoesters, fatty acid protein hydrolysates, isethionates, imidazolinium derivatives, methyl taurates, sarcosinates, fatty acid amide ether sulfates, alkylamidobetaines, fatty alcohols, fatty acid glycerides, fatty acid diethanolamides, vegetable and synthetic oils, lanolin derivatives, ethoxylated glycerol fatty acid esters, or mixtures of these substances.

Face and body oils may comprise the customary vehicles, such as synthetic oils, such as fatty acid esters, fatty alcohols, silicone oils, natural oils, such as vegetable oils and oily plant extracts, paraffin oils or lanolin oils, or mixtures of these substances.

Further typical cosmetic use forms are also lipsticks, lipcare sticks, mascara, eyeliner, eye-shadow, rouge, powder make-up, emulsion make-up and wax make-up, and sunscreen, pre-sun and after-sun preparations.

The preferred composition forms according to the invention include, in particular, emulsions.

Emulsions according to the invention are advantageous and comprise, for example, the said fats, oils, waxes and other fatty substances, as well as water and an emulsifier, as usually used for a composition of this type. The lipid phase may advantageously be selected from the following group of substances:

mineral oils, mineral waxes;
oils, such as triglycerides of capric or caprylic acid, furthermore natural oils, such as, for example, castor oil;
fats, waxes and other natural and synthetic fatty substances, preferably esters of fatty acids with alcohols having a low carbon number, for example with isopropanol, propylene glycol or glycerol, or esters of fatty alcohols with alkanoic acids having a low carbon number or with fatty acids;
silicone oils, such as dimethylpolysiloxanes, diethylpolysiloxanes, diphenylpolysiloxanes and mixed forms thereof.

For the purposes of the present invention, the oil phase of the emulsions, oleogels or hydrodispersions or lipodispersions is advantageously selected from the group of the esters of saturated and/or unsaturated, branched and/or unbranched alkanecarboxylic acids having a chain length of 3 to 30 C atoms and saturated and/or unsaturated, branched and/or unbranched alcohols having a chain length of 3 to 30 C atoms, or from the group of the esters of aromatic carboxylic acids and saturated and/or unsaturated, branched and/or unbranched alcohols having a chain length of 3 to 30 C atoms. Ester oils of this type can then advantageously be selected from the group isopropyl myristate, isopropyl palmitate, isopropyl stearate, isopropyl oleate, n-butyl stearate, n-hexyl laurate, n-decyl oleate, isooctyl stearate, isononyl stearate, isononyl isononanoate, 2-ethylhexyl palmitate, 2-ethylhexyl laurate, 2-hexyldecyl stearate, 2-octyldodecyl palmitate, oleyl oleate, oleyl erucate, erucyl oleate, erucyl erucate and synthetic, semi-synthetic and natural mixtures of esters of this type, for example jojoba oil.

The oil phase may furthermore advantageously be selected from the group of the branched and unbranched hydrocarbons and waxes, silicone oils, dialkyl ethers, or the group of the saturated and unsaturated, branched and unbranched alcohols, and fatty acid triglycerides, specifically the triglycerol esters of saturated and/or unsaturated, branched and/or unbranched alkanecarboxylic acids having a chain length of 8 to 24, in particular 12-18, C atoms. The fatty acid triglycerides may advantageously be selected, for example, from the group of the synthetic, semi-synthetic and natural oils, for example olive oil, sunflower oil, soya oil, peanut oil, rapeseed oil, almond oil, palm oil, coconut oil, palm kernel oil and the like.

Any desired mixtures of oil and wax components of this type may also advantageously be employed for the purposes of the present invention. It may also be advantageous to employ waxes, for example cetyl palmitate, as the only lipid component of the oil phase.

The oil phase is advantageously selected from the group 2-ethylhexyl isostearate, octyldodecanol, isotridecyl isononanoate, isoeicosane, 2-ethylhexyl cocoate, $C_{12-15}$-alkyl benzoate, caprylic/capric acid triglyceride and dicapryl ether.

Particularly advantageous are mixtures of $C_{12-15}$-alkyl benzoate and 2-ethylhexyl isostearate, mixtures of $C_{12-15}$-alkyl benzoate and isotridecyl isononanoate, as well as mixtures of $C_{12-15}$-alkyl benzoate, 2-ethylhexyl isostearate and isotridecyl isononanoate.

Of the hydrocarbons, paraffin oil, squalane and squalene may advantageously be used for the purposes of the present invention.

Furthermore, the oil phase may also advantageously have a content of cyclic or linear silicone oils or consist entirely of oils of this type, although it is preferred to use an additional content of other oil-phase components in addition to the silicone oil or the silicone oils.

The silicone oil to be used in accordance with the invention is advantageously cyclomethicone (octamethylcyclotetrasiloxane). However, it is also advantageous for the purposes of the present invention to use other silicone oils, for example hexamethylcyclotrisiloxane, polydimethylsiloxane or poly (methylphenylsiloxane).

Also particularly advantageous are mixtures of cyclomethicone and isotridecyl isononanoate and of cyclomethicone and 2-ethylhexyl isostearate.

The aqueous phase of the compositions according to the invention optionally advantageously comprises alcohols, diols or polyols having a low carbon number, and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products, furthermore alcohols having a low carbon number, for example ethanol, isopropanol, 1,2-propanediol or glycerol, and, in particular, one or more thickeners, which may advantageously be selected from the group silicon dioxide, aluminium silicates, polysaccharides and derivatives thereof, for example hyaluronic acid, xanthan gum, hydroxypropylmethylcellulose, particularly advantageously from the group of the polyacrylates, preferably a polyacrylate from the group of the so-called Carbopols, for example Carbopol grades 980, 981, 1382, 2984 or 5984, in each case individually or in combination.

In particular, mixtures of the above-mentioned solvents are used. In the case of alcoholic solvents, water may be a further constituent.

Emulsions according to the invention are advantageous and comprise, for example, the said fats, oils, waxes and other fatty substances, as well as water and an emulsifier, as usually used for a formulation of this type.

In a preferred embodiment, the compositions according to the invention comprise hydrophilic surfactants.

The hydrophilic surfactants are preferably selected from the group of the alkylglucosides, acyl lactylates, betaines and coconut amphoacetates.

The alkylglucosides are themselves advantageously selected from the group of the alkylglucosides which are distinguished by the structural formula

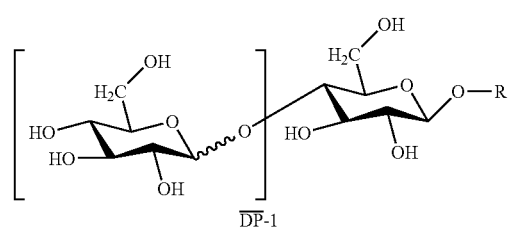

where R is a branched or unbranched alkyl radical having 4 to 24 carbon atoms, and where $\overline{DP}$ denotes a mean degree of glucosylation of up to 2.

The value $\overline{DP}$ represents the degree of glucosidation of the alkylglucosides used in accordance with the invention and is defined as $$\overline{DP} = \frac{p_1}{100} \cdot 1 + \frac{p_2}{100} \cdot 2 + \frac{p_3}{100} \cdot 3 + \ldots = \sum \frac{p_i}{100} \cdot i$$

in which $p_1, p_2, p_3 \ldots p_i$ represent the proportion of mono-, di-, tri- ... i-fold glucosylated products in percent by weight. Products which are advantageous according to the invention are those having degrees of glucosylation of 1-2, particularly advantageously of 1.1 to 1.5, very particularly advantageously of 1.2-1.4, in particular of 1.3.

The value DP takes into account the fact that alkylglucosides are generally, as a consequence of their preparation, in the form of mixtures of mono- and oligoglucosides. A relatively high content of monoglucosides, typically in the order of 40-70% by weight, is advantageous in accordance with the invention.

Alkylglycosides which are particularly advantageously used for the purposes of the invention are selected from the group octyl glucopyranoside, nonyl glucopyranoside, decyl glucopyranoside, undecyl glucopyranoside, dodecyl glucopyranoside, tetradecyl glucopyranoside and hexadecyl glucopyranoside.

It is likewise advantageous to employ natural or synthetic raw materials and assistants or mixtures which are distinguished by an effective content of the active ingredients used in accordance with the invention, for example Plantaren® 1200 (Henkel KGaA), Oramix® NS 10 (Seppic).

The acyllactylates are themselves advantageously selected from the group of the substances which are distinguished by the structural formula

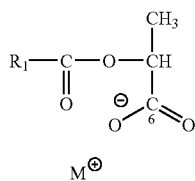

where $R^1$ is a branched or unbranched alkyl radical having 1 to 30 carbon atoms, and $M^+$ is selected from the group of the alkali metal ions and the group of the ammonium ions which are substituted by one or more alkyl and/or one or more hydroxyalkyl radicals, or corresponds to half an equivalent of an alkaline earth metal ion.

For example, sodium isostearyl lactylate, for example the product Pathionic® ISL from the American Ingredients Company, is advantageous.

The betaines are advantageously selected from the group of the sub-stances which are distinguished by the structural formula

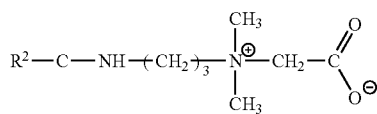

where $R^2$ is a branched or unbranched alkyl radical having 1 to 30 carbon atoms.

$R^2$ is particularly advantageously a branched or unbranched alkyl radical having 6 to 12 carbon atoms.

For example, capramidopropylbetaine, for example the product Tego® Betain 810 from Th. Goldschmidt AG, is advantageous.

A coconut amphoacetate which is advantageous for the purposes of the invention is, for example, sodium coconut amphoacetate, as available under the name Miranol® Ultra C32 from Miranol Chemical Corp.

The compositions according to the invention are advantageously characterised in that the hydrophilic surfactant(s) is (are) present in concentrations of 0.01-20% by weight, preferably 0.05-10% by weight, particularly preferably 0, 1-5% by weight, in each case based on the total weight of the composition.

For use, the cosmetic and dermatological compositions are applied in sufficient amount to the skin and/or hair in the usual manner for cosmetics.

Cosmetic and dermatological compositions according to the invention may exist in various forms. Thus, they may be, for example, a solution, a waterfree composition, an emulsion or microemulsion of the water-in-oil (W/O) or oil-in-water (O/W) type, a multiple emulsion, for example of the water-in-oil-in-water (W/O/W) type, a gel, a solid stick, an ointment or an aerosol. It is also advantageous to administer ectoines in encapsulated form, for example in collagen matrices and other conventional encapsulation materials, for example as cellulose encapsulations, in gelatine, wax matrices or liposomally encapsulated. In particular, wax matrices, as described in DE-A 43 08 282, have proven favourable. Preference is given to emulsions. O/W emulsions are particularly preferred. Emulsions, W/O emulsions and O/W emulsions are obtainable in a conventional manner.

Emulsifiers that can be used are, for example, the known W/O and O/W emulsifiers. It is advantageous to use further conventional co-emulsifiers in the preferred O/W emulsions according to the invention.

Co-emulsifiers which are advantageous according to the invention are, for example, O/W emulsifiers, principally from the group of the substances having HLB values of 11-16, very particularly advantageously having HLB values of 14.5-15.5, so long as the O/W emulsifiers have saturated radicals R and R'. If the O/W emulsifiers have unsaturated radicals R and/or R' or in the case of isoalkyl derivatives, the preferred HLB value of such emulsifiers may also be lower or higher.

It is advantageous to select the fatty alcohol ethoxylates from the group of the ethoxylated stearyl alcohols, cetyl alcohols, cetylstearyl alcohols (cetearyl alcohols). Particular preference is given to the following: polyethylene glycol (13) stearyl ether (steareth-13), polyethylene glycol (14) stearyl ether (steareth-14), polyethylene glycol (15) stearyl ether (steareth-15), polyethylene glycol (16) stearyl ether (steareth-16), polyethylene glycol (17) stearyl ether (steareth-17), polyethylene glycol (18) stearyl ether (steareth-18), polyethylene glycol (19) stearyl ether (steareth-19), polyethylene glycol (20) stearyl ether (steareth-20), polyethylene glycol (12) isostearyl ether (isosteareth-12), polyethylene glycol (13) isostearyl ether (isosteareth-13), polyethylene glycol (14) isostearyl ether (isosteareth-14), polyethylene glycol (15) isostearyl ether (isosteareth-15), polyethylene glycol (16) isostearyl ether (isosteareth-16), polyethylene glycol (17) isostearyl ether (isosteareth-17), polyethylene glycol (18) isostearyl ether (isosteareth-18), polyethylene glycol (19) isostearyl ether (isosteareth-19), polyethylene glycol (20) isostearyl ether (isosteareth-20), polyethylene glycol (13) cetyl ether (ceteth-13), polyethylene glycol (14) cetyl ether (ceteth-14), polyethylene glycol (15) cetyl ether (ceteth-15), polyethylene glycol (16) cetyl ether (ceteth-16), polyethylene glycol (17) cetyl ether (ceteth-17), polyethylene glycol (18) cetyl ether (ceteth-18), polyethylene glycol (19) cetyl ether (ceteth-19), polyethylene glycol (20) cetyl ether (ceteth-20), polyethylene glycol (13) isocetyl ether (isoceteth-13), polyethylene glycol (14) isocetyl ether (isoceteth-14), polyethylene glycol (15) isocetyl ether (isoceteth-15), polyethylene glycol (16) isocetyl ether (isoceteth-16), polyethylene glycol (17) isocetyl ether (isoceteth-17), polyethylene glycol (18) isocetyl ether (isoceteth-18), polyethylene glycol (19) isocetyl ether (isoceteth-19), polyethylene glycol (20) isocetyl ether (isoceteth-20), polyethylene glycol (12) oleyl ether (oleth-12), polyethylene glycol (13) oleyl ether (oleth-13), polyethylene glycol (14) oleyl ether (oleth-14), polyethylene glycol (15) oleyl ether (oleth-15), polyethylene glycol (12) lauryl ether (laureth-12), polyethylene glycol (12) isolauryl ether (isolaureth-12), polyethylene glycol (13) cetylstearyl ether (ceteareth-13), polyethylene glycol (14) cetylstearyl ether (ceteareth-14), polyethylene glycol (15) cetylstearyl ether (ceteareth-15), polyethylene glycol (16) cetylstearyl ether (ceteareth-16), polyethylene glycol (17) cetylstearyl ether (ceteareth-17), polyethylene glycol (18) cetylstearyl ether (ceteareth-18), polyethylene glycol (19) cetylstearyl ether (ceteareth-19), polyethylene glycol (20) cetylstearyl ether (ceteareth-20).

It is furthermore advantageous to select the fatty acid ethoxylates from the following group:

polyethylene glycol (20) stearate, polyethylene glycol (21) stearate, polyethylene glycol (22) stearate, polyethylene glycol (23) stearate, polyethylene glycol (24) stearate, polyethylene glycol (25) stearate, polyethylene glycol (12) isostearate, polyethylene glycol (13) isostearate, polyethylene glycol

(14) isostearate, polyethylene glycol (15) isostearate, polyethylene glycol (16) isostearate, polyethylene glycol (17) isostearate, polyethylene glycol (18) isostearate, polyethylene glycol (19) isostearate, polyethylene glycol (20) isostearate, polyethylene glycol (21) isostearate, polyethylene glycol (22) isostearate, polyethylene glycol (23) isostearate, polyethylene glycol (24) isostearate, polyethylene glycol (25) isostearate, polyethylene glycol (12) oleate, polyethylene glycol (13) oleate, polyethylene glycol (14) oleate, polyethylene glycol (15) oleate, polyethylene glycol (16) oleate, polyethylene glycol (17) oleate, polyethylene glycol (18) oleate, polyethylene glycol (19) oleate, polyethylene glycol (20) oleate.

An ethoxylated alkyl ether carboxylic acid or salt thereof which can advantageously be used is sodium laureth-11 carboxylate. An alkyl ether sulfate which can advantageously be used is sodium laureth-4 sulfate. An ethoxylated cholesterol derivative which can advantageously be used is polyethylene glycol (30) cholesteryl ether. Polyethylene glycol (25) soyasterol has also proven successful. Ethoxylated triglycerides which can advantageously be used are the polyethylene glycol (60) evening primrose glycerides.

It is furthermore advantageous to select the polyethylene glycol glycerol fatty acid esters from the group polyethylene glycol (20) glyceryl laurate, polyethylene glycol (21) glyceryl laurate, polyethylene glycol (22) glyceryl laurate, polyethylene glycol (23) glyceryl laurate, polyethylene glycol (6) glyceryl caprate/caprinate, polyethylene glycol (20) glyceryl oleate, polyethylene glycol (20) glyceryl isostearate, polyethylene glycol (18) glyceryl oleate cocoate.

It is likewise favourable to select the sorbitan esters from the group polyethylene glycol (20) sorbitan monolaurate, polyethylene glycol (20) sorbitan monostearate, polyethylene glycol (20) sorbitan monoisostearate, polyethylene glycol (20) sorbitan monopalmitate, polyethylene glycol (20) sorbitan monooleate.

Optional W/O emulsifiers, but ones which may nevertheless be advantageous for the purposes of the invention can be the following:

fatty alcohols having 8 to 30 C atoms, monoglycerol esters of saturated and/or unsaturated, branched and/or unbranched alkanecarboxylic acids having a chain length of 8 to 24 C atoms, in particular 12-18 C atoms, diglycerol esters of saturated and/or unsaturated, branched and/or unbranched alkanecarboxylic acids having a chain length of 8 to 24 C atoms, in particular 12-18 C atoms, monoglycerol ethers of saturated and/or unsaturated, branched and/or unbranched alcohols having a chain length of 8 to 24 C atoms, in particular 12-18 C atoms, diglycerol ethers of saturated and/or unsaturated, branched and/or unbranched alcohols having a chain length of 8 to 24 C atoms, in particular 12-18 C atoms, propylene glycol esters of saturated and/or unsaturated, branched and/or unbranched alkanecarboxylic acids having a chain length of 8 to 24 C atoms, in particular 12-18 C atoms, and sorbitan esters of saturated and/or unsaturated, branched and/or unbranched alkanecarboxylic acids having a chain length of 8 to 24 C atoms, in particular 12-18 C atoms.

Particularly advantageous W/O emulsifiers are glyceryl monostearate, glyceryl monoisostearate, glyceryl monomyristate, glyceryl monooleate, diglyceryl monostearate, diglyceryl monoisostearate, propylene glycol monostearate, propylene glycol monoisostearate, propylene glycol monocaprylate, propylene glycol monolaurate, sorbitan monoisostearate, sorbitan monolaurate, sorbitan monocaprylate, sorbitan monoisooleate, sucrose distearate, cetyl alcohol, stearyl alcohol, arachidyl alcohol, behenyl alcohol, isobehenyl alcohol, selachyl alcohol, chimyl alcohol, polyethylene glycol (2) stearyl ether (steareth-2), glyceryl monolaurate, glyceryl monocaprinate and glyceryl monocaprylate.

Preferred compositions according to the invention are particularly suitable for protecting human skin against ageing processes and against oxidative stress, i.e. against damage by free radicals, as are produced, for example, by sunlight, heat or other influences. In this connection, they are in the various administration forms usually used for this application. For example, they may, in particular, be in the form of a lotion or emulsion, such as in the form of a cream or milk (O/W, W/O, O/W/O, W/O/W), in the form of oily-alcoholic, oily-aqueous or aqueous-alcoholic gels or solutions, in the form of solid sticks or may be formulated as an aerosol.

The composition may comprise cosmetic adjuvants which are usually used in this type of composition, such as, for example, thickeners, softeners, moisturizers, surfactants, emulsifiers, preservatives, antifoams, perfumes, waxes, lanolin, propellants, dyes and/or pigments which colour the composition itself or the skin, and other ingredients usually used in cosmetics.

The dispersant or solubiliser used can be an oil, wax or other fatty substance, a lower monoalcohol or lower polyol or mixtures thereof. Particularly preferred monoalcohols or polyols include ethanol, isopropanol, propylene glycol, glycerol and sorbitol.

A preferred embodiment of the invention is an emulsion in the form of a protective cream or milk which, apart from the compound(s) of the formula I or formula II, comprises, for example, fatty alcohols, fatty acids, fatty acid esters, in particular triglycerides of fatty acids, lanolin, natural and synthetic oils or waxes and emulsifiers in the presence of water.

Further preferred embodiments are oily lotions based on natural or synthetic oils and waxes, lanolin, fatty acid esters, in particular triglycerides of fatty acids, or oily-alcoholic lotions based on a lower alcohol, such as ethanol, or a glycerol, such as propylene glycol, and/or a polyol, such as glycerol, and oils, waxes and fatty acid esters, such as triglycerides of fatty acids.

The composition according to the invention may also be in the form of an alcoholic gel which comprises one or more lower alcohols or polyols, such as ethanol, propylene glycol or glycerol, and a thickener, such as siliceous earth. The oily-alcoholic gels also comprise natural or synthetic oil or wax.

The solid sticks consist of natural or synthetic waxes and oils, fatty alcohols, fatty acids, fatty acid esters, lanolin and other fatty substances.

If a composition is formulated as an aerosol, the customary propellants, such as alkanes, fluoroalkanes and chlorofluoroalkanes, are generally used.

The cosmetic composition may also be used to protect the hair against photochemical damage in order to prevent changes of colour shade, bleaching or damage of a mechanical nature. In this case, a suitable formulation is in the form of a rinse-out shampoo, lotion, gel or emulsion, the composition in question being applied before or after shampooing, before or after colouring or bleaching or before or after permanent waving. It is also possible to select a composition in the form of a lotion or gel for styling or treating the hair, in the form of a lotion or gel for brushing or blow-waving, in the form of a hair lacquer, permanent waving composition, colorant or bleach for the hair. Besides the compound(s) of the formula I or formula II, the composition having light-protection properties may comprise various adjuvants used in this type of composition, such as surfactants, thickeners, polymers, softeners, preservatives, foam stabilisers, electrolytes, organic solvents, silicone derivatives, oils, waxes, antigrease agents, dyes and/or pigments which colour the composition itself or the hair, or other ingredients usually used for hair care.

The present invention furthermore relates to a process for the preparation of a composition which is characterised in that at least one compound of the formula I or formula II containing radicals as described above is mixed with a cosmetically or dermatologically or food-suitable vehicle, and to the use of a compound of the formula I or formula II for the preparation of a composition.

The compositions according to the invention can be prepared herewith the aid of techniques which are well known to the person skilled in the art.

The mixing can result in dissolution, emulsification or dispersal of the compound of the formula I or formula II in the vehicle.

It has also been noted that compounds of the formula I or formula II can have a stabilising effect on the composition. When used in corresponding products, the latter are thus also stable for longer and do not change their appearance. In particular, the effectiveness of the ingredients, for example vitamins, is retained even in the case of application over extended periods or extended storage. This is, inter alia, particularly advantageous in the case of compositions for protecting the skin against the effect of UV rays since these cosmetics are exposed to particularly high stresses by UV radiation.

The positive effects of compounds of the formula I or formula II give rise to their particular suitability for use in cosmetic or pharmaceutical compositions.

The properties of compounds of the formula I or formula II should likewise be regarded as positive for use in foods or as food supplements or as functional foods. The further explanations given for foods also apply correspondingly to food supplements and functional foods.

The foods which can be enriched with one or more compounds of the formula I or formula II in accordance with the present invention include all materials which are suitable for consumption by animals or consumption by humans, for example vitamins and provitamins thereof, fats, minerals or amino acids. (The foods may be solid, but also liquid, i.e. in the form of a beverage). The present invention accordingly furthermore relates to the use of a compound of the formula I or formula II as food additive for human or animal nutrition, and to compositions which are foods or food supplements and comprise corresponding vehicles.

Foods which can be enriched with one or more compounds of the formula I or formula II in accordance with the present invention are, for example, also foods which originate from a single natural source, such as, for example, sugar, unsweetened juice, squash or puree of a single plant species, such as, for example, unsweetened apple juice (for example also a mixture of different types of apple juice), grapefruit juice, orange juice, apple compote, apricot squash, tomato juice, tomato sauce, tomato puree, etc. Further examples of foods which can be enriched with one or more compounds of the formula I or formula II in accordance with the present invention are corn or cereals from a single plant species and materials produced from plant species of this type, such as, for example, cereal syrup, rye flour, wheat flour or oat bran. Mixtures of foods of this type are also suitable for being enriched with one or more compounds of the formula I or formula II in accordance with the present invention, for example multivitamin preparations, mineral mixtures or sweetened juice. As further examples of foods which can be enriched with one or more compounds of the formula I or formula II in accordance with the present invention, mention may be made of food compositions, for example prepared cereals, biscuits, mixed drinks, foods prepared especially for children, such as yoghurt, diet foods, low-calorie foods or animal feeds.

The foods which can be enriched with one or more compounds of the formula I or formula II in accordance with the present invention thus include all edible combinations of carbohydrates, lipids, proteins, inorganic elements, trace elements, vitamins, water or active metabolites of plants and animals.

The foods which can be enriched with one or more compounds of the formula I or formula II in accordance with the present invention are preferably administered orally, for example in the form of meals, pills, tablets, capsules, powders, syrup, solutions or suspensions.

The foods according to the invention enriched with one or more compounds of the formula I or formula II can be prepared with the aid of techniques which are well known to the person skilled in the art.

Furthermore, compounds of the formula I have only a weak inherent colour. The weak inherent colour is, for example, a major advantage if an inherent colour of the ingredients is undesired in the products for aesthetic reasons.

The proportion of the compounds of the formula I or II in the composition is preferably 0.01 to 20% by weight, particularly preferably 0.05 to 10% by weight and especially preferably 0.1 to 5% by weight, based on the composition as a whole. The proportion of the compounds of the formula I or II in the composition is very particularly preferably 0.1 to 2% by weight, based on the composition as a whole.

Even without further comments, it is assumed that a person skilled in the art will be able to utilise the above description in the broadest scope. The preferred embodiments should therefore merely be regarded as descriptive disclosure which is absolutely not limiting in any way. The complete disclosure content of all applications and publications mentioned above and below is incorporated into this application by way of reference. The following examples are intended to illustrate the present invention. However, they should in no way be regarded as limiting. All compounds or components which can be used in the compositions are either known and commercially available or can be synthesised by known methods. The INCI names of the raw materials used are as follows:

EXAMPLES

Example 1a

Reaction of dihydroxyacetone (DHA) with (E)-(4-methoxy)cinnamyl chloride

A solution of (E)-(4-methoxy)cinnamyl chloride (1.00 g, 5 mmol) in abs. dichloromethane (15 ml) is slowly added dropwise with stirring at 0-5° C. to a solution of dihydroxyacetone (2.70 g, 30 mmol) in abs. pyridine (50 ml) in a three-necked flask. The mixture is subsequently stirred at 10° C. for 1 h and then at room temperature for 5 h. The solvent is then distilled off, and the crude product which remains is taken up in water (100 ml) and extracted with ethyl acetate (3×20 ml). The combined organic phases are washed with water (2×50 ml) and dried over magnesium sulfate. The crude product remaining after evaporation of the ethyl acetate in vacuo is recrystallised from ethanol (7 ml). The precipitated 1,3-bis-[(E)-3-(4-methoxyphenyl)-2-propenoyloxy]-2-oxopropane is filtered off and washed with ethanol (2×5 ml). The filtrate is evaporated in vacuo and worked up by column chromatography using (ethyl acetate:cyclohexane—3:1).

1st fraction: ($R_f$=0.38):

1,3-Bis-[(E)-3-(4-methoxyphenyl)-2-propenoyloxy]-2-oxopropane

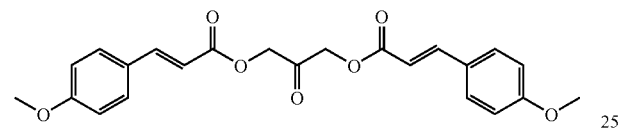

Yield 32%

$C_{23}H_{22}O_7$; M=410.43

$R_f$=0.38 (ethyl acetate:cyclohexane—3:1), as white crystals of m.p. 146-148° C. (ethanol).

$^1$H-NMR (300 MHz, DMSO-$d_6$): 7.73 (d, J=8.76, 4H, Ar—H), 7.69 (d, J=15.95, 2H, CH=CHCO), 7.00 (d, J=8.76, 4H, Ar—H), 6.60 (d, J=15.95, 2H, Ar—CH=CH), 5.05 (s, 4H, $CH_2$), 3.81 (s, 6H, $OCH_3$).

$^{13}$C-NMR (75 MHz, DMSO-$d_6$): 198.6, 165.6, 161.3, 145.4, 130.3, 126.4, 114.3, 114.2, 65.8, 55.3.

MS (EI): 410 (20) [M$^+$], 219 (20), 161 (100), 133 (6).

UV-VIS (1 mg/100 ml; $\lambda_{max}$[nm], $\epsilon$): 307.0 (1.140).

2nd fraction: ($R_f$=0.61):

1-Hydroxy-3-[(E)-3-(4-methoxyphenyl)-2-propenoyloxy]-2-oxopropane

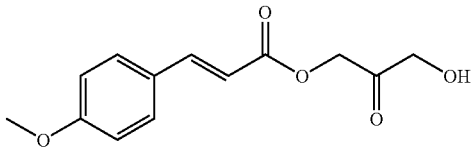

Yield 62%.

$C_{13}H_{14}O_5$; M=250.25

$R_f$=0.61 (ethyl acetate:cyclohexane—3:1), white crystals of m.p. 172-174° C.

$^1$H-NMR (300 MHz, DMSO-$d_6$): 7.73 (d, J=8.71 Hz, 2H, Ar—H), 7.65 (d, J=16.05 Hz, 1H, CH=CHCO), 6.98 (d, J=8.71 Hz, 2H, Ar—H), 6.57 (d, J=16.05 Hz, 1H, CH=CHCO), 5.42 (t, J=5.99 Hz, 1H, OH, exchangeable with $D_2O$), 4.99 (s, 2H, $OCH_2CO$), 4.17 (d, J=5.99 Hz, 2H, $CH_2OH$), 3.80 (s, 3H, OMe).

$^{13}$C-NMR (75 MHz, DMSO-$d_6$): 203.7, 164.5, 160.0, 143.8, 129.0, 125.2, 113.6, 113.1, 65.0, 64.5, 54.1.

MS (EI): 250 (24) [M$^+$], 219 (22), 178 (10), 161 (100), 133 (23), 118 (7).

UV-VIS (1 mg/100 ml; $\lambda_{max}$[nm], $\epsilon$): 301.0 (0.947) (cf. FIG. 2).

Example 1b

1-Hydroxy-3-(2-cyano-3,3-diphenylacryloyloxy)-2-oxopropane is obtained from 2-cyano-3,3-diphenylacryloyl chloride in accordance with the working procedure from Example 1a.

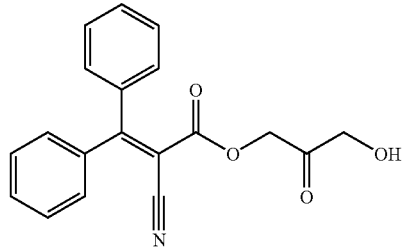

Yield: 69%.

$C_{19}H_{15}NO_4$; M=321.34

$R_f$=0.37 (chloroform:methanol—95:5), as pale-yellowish solid of m.p. 204° C. (decomp.).

$^1$H-NMR (300 MHz, DMSO-$d_6$): 7.20-7.70 (m, 10H, Ar—H), 5.43 (t, J=5.99 Hz, 1H, OH, exchangeable with $D_2O$), 5.00 (s, 2H, $OCH_2CO$), 4.17 (d, J=5.99 Hz, 2H, $CH_2OH$).

MS (EI): 321 (4) [M$^+$], 290 (6), 262 (24), 249 (100), 232 (74), 220 (6), 204 (86), 190 (7), 176 (32), 165 (23), 151 (11), 77 (14).

UV-VIS (1 mg/100 ml; $\lambda_{max}$[nm], $\epsilon$): 303.0 (0.375) (cf. FIG. 1).

The second product obtained is:

1,3-Bis-(2-cyano-3,3-diphenylacryloyloxy)-2-oxopropane

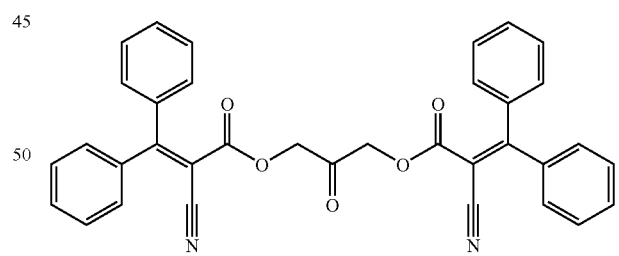

Yield: 30%.

$C_{35}H_{24}N_2O_5$; M=552.59

$R_f$=0.92 (chloroform:methanol—95:5), as white solid of m.p. 209° C.

$^1$H-NMR (300 MHz, DMSO-$d_6$): 7.23 (m, 4H, Ar—H), 7.37-7.65 (m, 16H, Ar—H), 4.95 (s, 4H, $OCH_2CO$).

$^{13}$C-NMR (75 MHz, DMSO-$d_6$): 196.5, 170.8, 160.7, 138.4, 137.8, 131.5, 130.5, 129.8, 128.6, 128.1, 116.6, 102.5, 67.1.

MS (FD): 552 (75) [M$^+$].

UV-VIS (1 mg/100 ml; $\lambda_{max}$[nm], $\epsilon$): 304.0 (0.031).

Example 2

Reaction of 1-(tert-butyldimethylsilyloxy)-3-hydroxy-2-oxopropane with 4-dimethylaminobenzoyl chloride 4-Dimethylaminobenzoyl chloride (400 mg, 2 mmol) is added in one portion at RT to a solution of 1-(tert-butyldimethylsilyloxy)-3-hydroxy-2-oxopropane (E. L. Ferroni, V. DiTella, N. Ghanayem, R. Jeske, C. Jodlowski, et al., *J. Org. Chem.* 1999, 64, 4943) (480 mg, 2 mmol) in abs. pyridine (20 ml). The mixture is stirred at RT for 1 h and then at 60-70° C. for 2 h. The solvent is removed in vacuo, and the crude product which remains is taken up in water (100 ml), and the water solution is extracted with ethyl acetate (3×20 ml). The combined organic phases are washed with saturated sodium chloride solution (2×20 ml) and dried over magnesium sulfate. The residue remaining after evaporation of the ethyl acetate in vacuo is worked up by column chromatography.

1-(tert-Butyldimethylsilyloxy)-2-oxopropyl 4-dimethylaminobenzoate

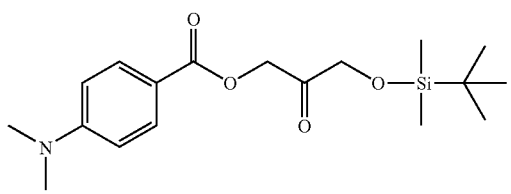

Yield: 84% (590 mg).
$C_{18}H_{29}NO_4Si$; M=351.52.
$R_f$=0.57 (ethyl acetate:cyclohexane—1:1), as white crystals of mp. 91-92° C.
$^1$H-NMR (300 MHz, DMSO-$d_6$): 7.70 (d, J=9.02 Hz, 2H, Ar—H), 6.65 (d, J=9.02 Hz, 2H, Ar—H), 4.92 (s, 2H, OCH$_2$CO), 4.34 (s, 2H, CH$_2$OSi), 2.93 (s, 6H, NMe$_2$), 0.80 (1s, 9H, 3Me), 0.00 (1s, 6H, 2Me).
$^{13}$C-NMR (75 MHz, DMSO-$d_6$): 203.4, 165.2, 153.4, 130.9, 114.9, 110.7, 67.0, 65.8, 39.4, 25.6, 17.9, −5.6.
MS (EI): [M+] 251 (32), 294 (48), 164 (24), 148 (100), 129 (12), 117 (16), 77 (9), 73 (41).
UV-VIS (1 mg/100 ml; $\lambda_{max}$[nm], $\epsilon$): 299.0 (0.67).

Example 3

Reaction of 1-(tert-butyldimethylsilyloxy)-2-oxopropyl esters/amides with hydrofluoric acid The corresponding starting material from Example 2 (1 mmol) is dissolved in an acetonitrile/water 3:1 mixture (30 ml), and 48% hydrofluoric acid (2 ml) is added at RT. The mixture is stirred at RT until the starting material has completely reacted (TLC check). A solution of sodium hydrogencarbonate in water is then added dropwise to the reaction mixture with stirring (to about pH=8). Water (50 ml) is added, the reaction mixture is extracted with dichloromethane (4×25 ml), and the combined organic extracts are dried over magnesium sulfate. The solvent is removed in vacuo. Recrystallisation of the residue from ethanol or work-up by column chromatography using the eluent indicated gives the corresponding 3-hydroxy-2-oxopropyl ester (or amide).

3-Hydroxy-2-oxopropyl 4-dimethylaminobenzoate is prepared in accordance with the general working procedure.

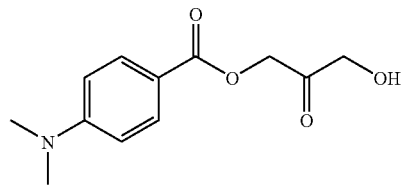

Yield: 96%.
$C_{12}H_{15}NO_4$; M=237.26.
$R_f$=0.24 (ethyl acetate:cyclohexane—1:2), white crystals of m.p. 129-131° C.
$^1$H-NMR (300 MHz, DMSO-$d_6$): 7.70 (d, J=9.02 Hz, 2H, Ar—H), 6.65 (d, J=9.02 Hz, 2H, Ar—H), 4.93 (s, 2H, OCH$_2$CO), 4.09 (s, 2H, CH$_2$OH), 2.93 (s, 6H, NMe$_2$).
$^{13}$C-NMR (75 MHz, DMSO-$d_6$): 205.3, 165.2, 153.4, 130.9, 114.9, 110.8, 66.2, 65.7, 39.1.
MS (EI): [M+] 237 (22), 164 (19), 148 (100), 120 (6), 105 (7), 77 (9).
UV-VIS (1 mg/100 ml; $\lambda_{max}$[nm], $\epsilon$): 311.0 (1.213).

Example 4

4-(4-Dimethylaminophenylcarbonyloxymethyl)-2,2-dimethyl-1,3-dioxolane

4-Dimethylaminobenzoyl chloride (1.00 g, 5 mmol) is added in one portion to a mixture of 4-hydroxymethyl-2,2-dimethyl-1,3-dioxolane (1.19 g, 10 mmol) and abs. pyridine (20 ml), and the mixture is stirred at room temperature for 10 min. The mixture is subsequently stirred at 80-90° C. for 2 h. Water (50 ml) is added, the reaction mixture is extracted with dichloromethane (3×25 ml), and the combined organic extracts are dried over magnesium sulfate. The solvent is removed in vacuo, and the residue is purified by column chromatography.

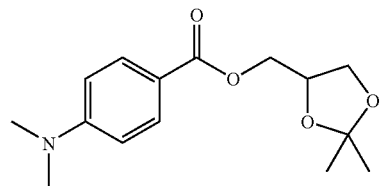

Yield: 94%.
$C_{15}H_{21}NO_4$; M=279.34
$^1$H-NMR (300 MHz, DMSO-$d_6$): 7.70 (d, J=9.02 Hz, 2H, Ar—H), 6.65 (d, J=9.02 Hz, 2H, Ar—H), 4.41, 4.10, 3.73 (3m, 2H+2H+1H, aliphatic protons), 1.37, 1.32 (3H+3H, 2s, 2CH$_3$), 2.93 (s, 6H, NMe$_2$).
MS (FD): [M+] 279 (64).
UV-VIS (1 mg/100 ml; $\lambda_{max}$[nm], $\epsilon$): 310.0 (0.86).

Example 5

2,3-Dihydroxypropyl 4-dimethylaminobenzoate 4-(4-Dimethylaminophenylcarbonyloxymethyl)-2,2-dimethyl-1,3-dioxolane from Example 4 (3 mmol) is dissolved in the diglyme/H$_2$O 8:2 mixture (25 ml), and boric acid (2 g) is added. The reaction mixture is stirred at 100° C. for 3 h. The solvent is then distilled off in vacuo, the crude product which remains is taken up in water (100 ml) and extracted with ethyl acetate (3×20 ml). The combined organic phases are washed with water (2×50 ml) and dried over magnesium sulfate. The crude product remaining after evaporation of the ethyl acetate in vacuo is employed without further purification for subsequent reactions.

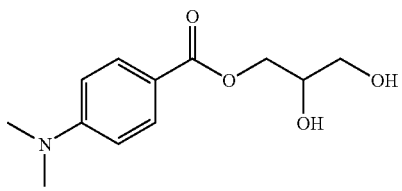

Yield: 98%.
C$_{12}$H$_{17}$NO$_4$; M=239.27
$^1$H-NMR (300 MHz, CDCl$_3$): 7.72 (d, J=9.02 Hz, 2H, Ar—H), 6.63 (d, J=9.02 Hz, 2H, Ar—H), 4.10, 4.07, 3.75 (2H+2H+1H, 3m, aliphatic protons), 2.93 (s, 6H, NMe$_2$).
MS (FD): [M+] 239 (25).
UV-VIS (1 mg/100 ml; λ$_{max}$[nm], ε): 310.0 (1.01).

Example 6

Reaction of 1,2-diols with tert-butyldimethylsilyl chloride

The corresponding 1,2-diol from Example 5 (2 mmol) is dissolved in abs. pyridine (10 ml) in a round-bottomed flask. After addition of tert-butyldimethylsilyl chloride (2.2 mmol), the mixture is stirred at room temperature for 12 h. The solvent is then distilled off in vacuo, and the crude product which remains is taken up in water (100 ml) and extracted with dichloromethane (3×20 ml). The combined organic phases are washed with water (2×50 ml) and dried over magnesium sulfate. The crude product remaining after evaporation of the dichloromethane in vacuo is worked up by column chromatography using the eluent indicated.

3-(tert-Butyldimethylsilyloxy)-2-hydroxypropyl 4-dimethylaminobenzoate

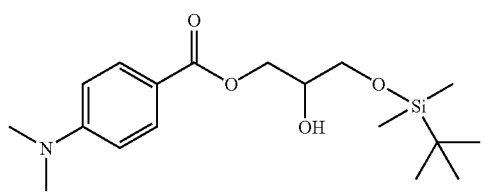

Yield: 88%.
C$_{18}$H$_{31}$NO$_4$Si; M=253.54
R$_f$=0.55 (ethyl acetate:cyclohexane—1:3), as colourless oil.
$^1$H-NMR (300 MHz, DMSO-d$_6$): 7.72 (d, J=9.02 Hz, 2H, Ar—H), 6.63 (d, J=9.02 Hz, 2H, Ar—H), 4.81 (d, 1H, CHOH, exchangeable with D$_2$O), 4.08, 3.74 (2m, 4H, OCH$_2$CHCH$_2$OSi), 3.61 (m, 1H, CH), 2.93 (s, 6H, NMe$_2$), 1.37, 1.35, 1.32 (3H+3H+3H, 3s, 3CH$_3$), 0.01 (s, 6H, SiMe$_2$).
MS (FD): [M+] 239 (25).
UV-VIS (1 mg/100 ml; λ$_{max}$[nm], ε): 310.0 (1.01).

Example 7

Oxidation of 3-(tert-butyldimethylsilyloxy)-2-hydroxypropyl derivatives from Example 2 using dimethyl sulfoxide/oxalyl dichloride (Swern oxidation)

A 100 ml one-necked flask with magnetic stirrer and three-way tap is evacuated, dried by heating and filled with dry protective gas. Under protective gas, a solution of (1.0 ml, 11 mmol) of oxalyl dichloride in 25 ml of dichloromethane is subsequently introduced into the flask through the three-way tap using an injection syringe. After cooling for a few minutes (internal temperature about −60° C.), a solution of dimethyl sulfoxide (1.7 ml, 22 mmol) in dichloromethane (5 ml) is added with stirring. After a short reaction time, 10 mmol of the alcohol to be oxidised in dichloromethane (10 ml) are subsequently added in portions over the course of 5 min. After a further 15 min, triethylamine (7 ml, 50 mmol) is added, the mixture is stirred for a further 5 min and subsequently warmed slowly to room temperature. Water (50 ml) is subsequently added to the reaction mixture, the organic phase is separated off, and the aqueous phase is extracted with dichloromethane (2×30 ml). The combined organic phases are washed with 100 ml of saturated sodium chloride solution and dried over magnesium sulfate. After removal of the solvent, the ketone obtained is generally sufficiently pure for further reactions. For further purification, the crude product can be worked up by column chromatography.

Example 7a

1-(tert-Butyldimethylsilyloxy)-2-oxopropyl 4-dimethylaminobenzoate

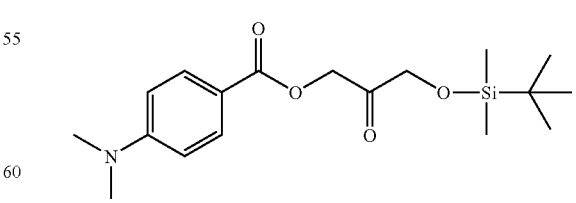

is obtained from 3-(t-butyldimethylsilyloxy)-2-hydroxypropyl 4-dimethylaminobenzoate (from Example 6) in 95% yield in accordance with the above general working procedure.

Example 8

Preparation of 3-[4-(3-hydroxy-2,2-dimethoxypropoxymethyl)benzylidene]-4,7,7-trimethylbicyclo[2.2.1]heptan-2-one A solution of 3-(4-bromomethylbenzylidene)-4,7,7-trimethylbicyclo[2.2.1]-heptan-2-one (C. Bouillon, C. Vayssie, in *Ger. Offen.*, (Oreal S. A., Fr.). Appl: DE 19780314. 78-2811041, 1978, p. 71. C. Bouillon, C. Vayssie, in *Fr. Demande*, (Oreal S. A., Fr.), Fr, Number 2421878, 1979, p. 31. C. Bouillon, C. Vayssie, (Oreal S. A., Fr.). Ca, Number 1113480, 1981, p. 61) (10.0 g, 30 mmol) in THF (30 ml) is slowly added dropwise at 40° C. with stirring to a solution of 2,2-dimethoxy-1,3-propanediol (M. W. Chun, D. H. Shin, H. R. Moon, J. Lee, H. Park, L. S. Jeong, *Bioorg. Med. Chem. Lett* 1997, 7, 1475. E. Cesarotti, P. Antognazza, M. Pallavicini, L. Villa, *Helv. Chim. Acta* 1993, 76, 2344. E. L. Ferroni, V. DiTella, N. Ghanayem, R. Jeske, C. Jodlowski, et al., *J. Org. Chem.* 1999, 64, 4943) (8.17 g, 60 mmol) and t-BuOK (4.50 g, 40 mmol) in t-BuOH (150 ml). E is stirred at 40° C. for 30 min and subsequently at the reflux temperature for 1 h. After the reaction mixture has been cooled, diethyl ether (30 ml) and water (100 ml) are added. The organic phase is separated off, and the aqueous phase is extracted with diethyl ether (3×50 ml). The combined organic phases are washed with saturated sodium chloride solution (3×70 ml) and dried over magnesium sulfate; the solvent is removed. Work-up by column chromatography using ethyl acetate:cyclohexane 1:1 gives

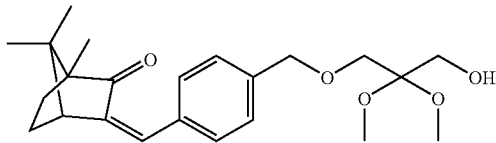

as clear oil.

$C_{23}H_{32}O_5$: 388 g/mol $R_f$=0.24 (ethyl acetate:cyclohexane—1:1).

$^1$H-NMR (300 MHz, DMSO-$d_6$): 7.54 (d, J=8.19 Hz, 2H, Ar—H), 7.40 (d, J=8.19 Hz, 2H, Ar—H), 7.11 (s, 1H, C=CH), 4.81 (t, J=5.60 Hz, 1H, $CH_2OH$, exchangeable with $D_2O$), 4.53 (s, 2H, Ar—$CH_2$), 3.48 (s, 2H, $OCH_2C$), 3.46 (d, J=5.60 Hz, 2H, $CH_2OH$), 3.20 (d, J=4.0 Hz, CH-camphor), 2.19, 1.81, 1.54-1.32 (3m, 4H, $CH_2CH_2$-camphor), 0.99, 0.95, 0.75 (3s, 3H+3H+3H, 3Me).

$^{13}$C-NMR (75 MHz, DMSO-$d_6$): 206.6, 141.9, 139.3, 134.1, 129.6, 127.9, 126.3, 100.6, 71.9, 66.1, 57.9, 56.4, 48.5, 47.3, 46.2, 30.0, 25.5, 20.1, 17.8, 9.2.

MS (EI): [M$^+$] 388 (1), 357 (12), 268 (4), 253 (11), 225 (3), 169 (3), 141 (7), 105 (100), 45 (9).

UV-VIS (1 mg/100 ml; $\lambda_{max}$[nm], ε): 298.0 (0.615).

Example 9

Preparation of 3-[4-(3-hydroxy-2-oxopropoxymethyl)benzylidene]-4,7,7-trimethylbicyclo[2.2.1]heptan-2-one 3-[4-(3-Hydroxy-2,2-dimethoxypropoxymethyl)benzylidene]-4,7,7-trimethylbicyclo[2.2.1]heptan-2-one from Example 8 (2 mmol) is dissolved in the $H_2O$/3N HCl 2:3 mixture (10 ml) and stirred at room temperature for 2 h. A solution of sodium hydrogencarbonate in water is then added dropwise to the reaction mixture with stirring (to about pH=8), and the reaction mixture is extracted with dichloromethane (3×10 ml). The combined organic extracts are dried over magnesium sulfate. The solvent is removed in vacuo, and the residue is purified by column chromatography using (ethyl acetate:cyclohexane—1:1).

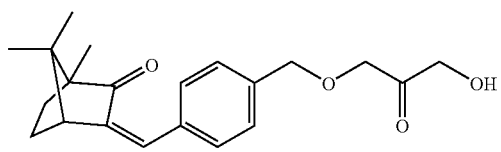

$C_{21}H_{26}O_4$: 342 g/mol

Yield: 95%.

$R_f$=0.39 (ethyl acetate:cyclohexane—1:1), as white crystals of m.p. 98-100° C.

$^1$H-NMR (300 MHz, DMSO-$d_6$): 7.55 (d, J=8.18 Hz, 2H, Ar—H), 7.41 (d, J=8.18 Hz, 2H, Ar—H), 7.10 (s, 1H, C=CH), 5.08 (t, J=5.61 Hz, 1H, $CH_2OH$, exchangeable with $D_2O$), 4.55 (s, 2H, Ar—$CH_2$), 4.30 (s, 2H, $OCH_2CO$), 4.16 (d, J=5.61 Hz, 2H, $CH_2OH$), 3.15 (d, J=4.0 Hz, CH camphor), 2.17, 1.79, 1.52-1.32 (3m, 4H, $CH_2CH_2$), 0.98, 0.93, 0.72 (3s, 3H+3H+3H, 3Me).

$^{13}$C-NMR (75 MHz, DMSO-$d_6$): 208.2, 206.6, 141.9, 138.8, 134.3, 129.6, 127.9, 126.2, 72.8, 71.8, 66.3, 65.8, 48.5, 46.1, 30.0, 25.5, 20.1, 17.8, 9.1.

MS (EI): [M$^+$] 342 (26), 270 (100), 253 (66), 169 (96), 141 (61), 41 (72).

UV-VIS (1 mg/100 ml; $\lambda_{max}$[nm], ε): 296.0 (0.874) (cf. FIG. 2).

Example 10

Reaction of acid chlorides with 3-amino-2,3-propanediols

The relevant 1-amino-2,3-propanediol (5 mmol) is dissolved in abs. dioxane (40 ml) under a protective-gas atmosphere in a 100 ml round-bottomed flask, and abs. triethylamine (0.76 ml, 5.5 mmol) is added. The solution of acid chloride (5 mmol) in dioxane (10 ml) is then slowly added dropwise with stirring at 5° C. The mixture is subsequently stirred at room temperature for 1 h and then at 80-90° C. for 1 h. The solvent is then distilled off, and the crude product which remains is taken up in water (100 ml) and extracted with ethyl acetate (3×20 ml). The combined organic phases are washed with saturated sodium chloride solution (15 ml) and dried over magnesium sulfate. The solvent is removed in vacuo, and the residue is purified by column chromatography.

Example 10a

N-(2,3-dihydroxypropyl)-(E)-3-(4-methoxyphenyl)acrylamide is prepared from (E)-(4-methoxy)cinnamyl chloride and amino-2,3-propanediol in accordance with the above general working procedure.

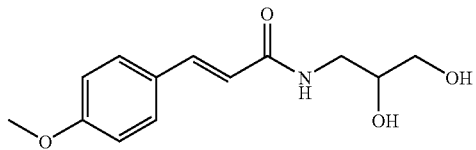

Yield: 90%
$C_{13}H_{17}NO_4$; M=251.28 g/mol
$R_f$=0.28 (chloroform:methanol—9:1) as white crystals of m.p. 104-106° C.
$^1$H-NMR (300 MHz, 90° C., DMSO-$d_6$): 8.04 (tr, J=5.62 Hz, NHCO), 7.52 (d, J=8.75 Hz, 2H, Ar—H), 7.38 (d, J=15.76 Hz, 1H, CH=CHCO), 6.97 (d, J=15.76 Hz, 1H, CH=CHCO), 6.59 (d, J=8.75 Hz, 2H, Ar—H), 4.87 (d, J=4.88, 1H, CHOH exchangeable with $D_2O$), 4.63 (tr, J=5.85 Hz, 1H, $CH_2OH$), 3.78 (s, 3H, OMe), 3.57, 3.35, 3.10 (3m, 1H+2H+2H, NH $CH_2CHCH_2OH$).
$^{13}$C-NMR (75 MHz, DMSO-$d_6$): 165.7, 160.2, 138.2, 128.9, 127.4, 119.7, 114.3, 70.5, 63.6, 55.1, 48.5, 42.2.
MS (EI): [M$^+$] 251 (7), 233 (4), 220 (6), 176 (9), 161 (100), 133 (18).
UV-VIS (1 mg/100 ml; $\lambda_{max}$[nm], $\epsilon$): 298.0 (0.940) (cf. FIG. 2).

Example 10b

N-(2,3-dihydroxypropyl)-N-methyl-(E)-3-(4-methoxyphenyl)acrylamide is prepared from (E)-(4-methoxy)cinnamyl chloride and 1-(methyl)amino-2,3-propanediol in accordance with the above general working procedure.

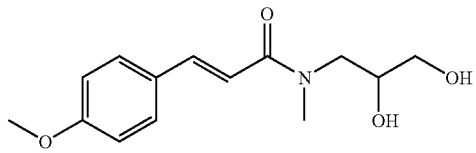

$C_{14}H_{19}O_4N$, 265.28 g/mol
Yield: 90%
$R_f$=0.31 (ethyl acetate:cyclohexane—2:5), as white crystals of m.p. 81-83° C.
$^1$H-NMR (300 MHz, 90° C., DMSO-$d_6$): 7.55 (d, J=8.70 Hz, 2H, Ar—H), 7.41 (d, J=15.69 Hz, 1H, CH=CHCO), 6.98 (d, J=15.69 Hz, 1H, CH=CHCO), 6.64 (d, J=8.70 Hz, 2H, Ar—H), 4.5, 4.3 (2bs, 1H+1H, 2OH, exchangeable with $D_2O$), 3.79 (s, 3H, OMe), 3.7, 3.54, 3.4 (3m, 1H+1H+3H, $NCH_2CHCH_2$), 3.08 (s, 3H, NMe).
$^{13}$C-NMR (75 MHz, 25° C., DMSO-$d_6$): (166.4), 166.0, (160.4), 160.2, (141.0), 139.9, (129.5), 129.2, 127.9, (127.7), 116.7, (115.9), 114.1, 70.5, (70.1), (63.7), 63.4, 55.1, 52.3, (51.1), (36.9), 34.8. The compound exists in two rotameric forms in DMSO solution at room temperature. Data in brackets relate to the rotamer which is present in smaller amount.
MS (EI): 265 (5) [M+], 247 (4), 204 (4), 190 (6), 161 (100), 142 (8), 133 (14), 121 (7), 91 (7).
UV-VIS (1 mg/100 ml; $\lambda_{max}$[nm], $\epsilon$): 301.0 (0.934) (cf. FIG. 2).

Example 10c

N-(2,3-dihydroxypropyl)-(E)-[4-(2-ethylhexyloxyphenyl)]acrylamide is prepared from (4-ethylhexyloxy)cinnamyl chloride and 1-amino-2,3-propanediol in accordance with the above general working procedure.

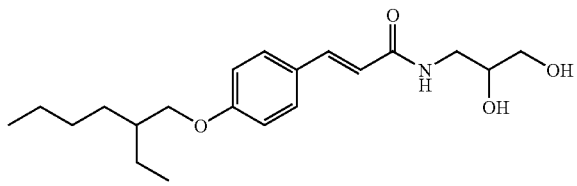

Yield: 90%
$C_{20}H_{31}NO_4$; M=449.47
$R_f$=0.27 (ethyl acetate:methanol—9:1), as colourless oil.
$^1$H-NMR (300 MHz, DMSO-$d_6$): 8.02 (tr, J=5.74 Hz, 1H, $CONHCH_2$), 7.49 (d, J=8.72 Hz, 2H, Ar—H), 7.37 (d, J=15.76 Hz, 1H, CH=CHCO), 6.96 (d, J=8.72 Hz, 2H, Ar—H), 6.59 (d, J=15.76 Hz, 1H, CH=CHCO), 4.86 (d, 1H, CHOH, exchangeable with $D_2O$), 4.60 (tr, 1H, $CH_2OH$, exchangeable with $D_2O$), 3.89 (d, J=6.05 Hz, 2H, $ArOCH_2CH$), 3.54, 3.36, 3.09 (3m, 5H, $NHCH_2CHCH_2OSi$), 1.68, 1.45, 1.27, 0.85 (4m, 15H).
$^{13}$C-NMR (75 MHz, DMSO-$d_6$): 165.7, 159.8, 138.2, 129.0, 127.3, 119.6, 114.7, 70.5, 69.9, 63.6, 42.2, 38.5, 29.8, 28.3, 23.2, 22.4, 13.9, 10.8.
MS (FD): [M$^+$] 449 (54).
UV-VIS (1 mg/100 ml; $\lambda_{max}$[nm], $\epsilon$): 307.0 (0.688).

Example 10d

N-(2,3-dihydroxypropyl)-4-dimethylaminobenzamide is prepared from 4-dimethylaminobenzoyl chloride and amino-2,3-propanediol in accordance with the above general working procedure.

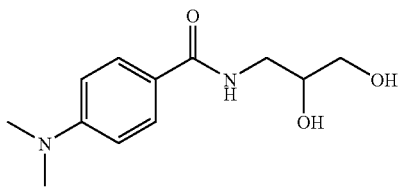

Yield: 95%.
$C_{12}H_{18}N_2O_3$; M=238.29.
$R_f$=0.26 (chloroform:methanol—9:1)
as white crystals of m.p. 152-153° C. (EtOH)

¹H-NMR (300 MHz, DMSO-d$_6$): 8.08 (tr, J=5.60 Hz, 1H, NHCO), 7.73 (d, J=9.02 Hz, 2H, Ar—H), 6.69 (d, J=9.02 Hz, 2H, Ar—H), 4.85 (d, J=4.88 Hz, 1H, CHOH exchangeable with D$_2$O), 4.60 (d, J=5.77 Hz, 1H, CH$_2$OH exchangeable with D$_2$O), 3.62, 3.36, 3.21 (3m, 5H, NHCH$_2$CHCH$_2$), 2.92 (s, 6H, NMe$_2$).

¹³C-NMR (75 MHz, DMSO-d$_6$): 166.7, 152.0, 128.5, 120.9, 110.7, 70.7, 63.8, 42.8, 39.7.

MS (EI): [M+] 238 (29), 207 (4), 178 (4), 164 (17), 148 (100), 119 (7), 105 (8), 91 (6), 77 (15).

UV-VIS (1 mg/100 ml; λ$_{max}$[nm], ε): 301.0 (0.947).

Example 11

3-(4-{[(2,3-Dihydroxypropyl)methylamino]methyl}benzylidene)-4,7,7-trimethylbicyclo[2.2.1]heptan-2-one 3-Methylamino-1,2-propanediol (1.05 g, 10 mmol) is dissolved in abs. DMF (20 ml) under a protective-gas atmosphere in a reaction vessel which has been dried by heating and flushed with pre-dried nitrogen, and abs. triethylamine (11 mmol) is added. 3-(4-Bromomethylbenzylidene)-4,7,7-trimethylbicyclo[2.2.1]heptan-2-one (C. Bouillon, C. Vayssie, in *Ger. Offen.*, (Oreal S. A., Fr.). Appl: DE 19780314. 78-2811041, 1978, p. 71. C. Bouillon, C. Vayssie, in *Fr. Demande*, (Oreal S. A., Fr.), Fr, Number 2421878, 1979, p. 31. C. Bouillon, C. Vayssie, (Oreal S. A., Fr.). Ca, Number 1113480, 1981, p. 61) (3.3 g, 10 mmol) is then added in one portion, and the mixture is stirred at 50° C. for 5 h. The solvent is removed in vacuo. Water (50 ml) is added to the residue, and the mixture is extracted with dichloromethane (3×20 ml). The combined organic phases are washed with water (20 ml) and dried over magnesium sulfate. The crude product remaining after evaporation of the dichloromethane is purified by column chromatography using chloroform/methanol—9:1.

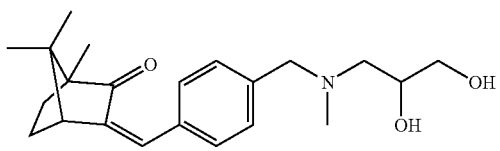

C$_{22}$H$_{31}$O$_3$N: 357 g/mol

R$_f$=0.27 (CH$_3$Cl:MeOH—9:1), as colourless oil.

¹H-NMR (300 MHz, DMSO-d$_6$): 7.51 (d, J=8.19 Hz, 2H, Ar—H), 7.38 (d, J=8.19 Hz, 2H, Ar—H), 7.10 (s, 1H, C═CH), 4.34 (d, J=3.8 Hz, 1H, CHOH, exchangeable with D$_2$O), 3.66 (m, 1H, CH$_2$OH, exchangeable with D$_2$O), 3.54 (d, J=3.9 Hz, 2H, NCH$_2$), 3.53 (m, 1H, CHOH), 3.23 (s, 2H, Ar—CH$_2$), 3.17 (d, J=4.2 Hz, 1H, CH-camphor), 2.39 (m, 2H, CH$_2$OH), 2.17 (s and m, 4H, NMe and CH camphor), 1.80, 1.53-1.32 (3m, 3H, CH$_2$CH$_2$), 0.98, 0.93, 0.72 (3s, 3H+3H+3H, 3Me)

¹³C-NMR (75 MHz, DMSO-d$_6$): 206.6, 141.7, 140.4, 133.7, 129.5, 129.1, 126.4, 69.2, 64.8, 61.8, 60.6, 56.4, 48.6, 46.1, 42.5, 30.0, 25.5, 20.1, 17.9, 9.2.

MS (EI): [M+] 357 (4), 296 (70), 253 (100), 225 (28), 169 (9), 141 (14).

UV-VIS (1 mg/100 ml; λ$_{max}$[nm], ε): 296.0 (0.711).

Example 12

N-[3-(tert-butyldimethylsilyloxy)-2-hydroxypropyl]-(E)-3-(4-methoxyphenyl)acrylamide is prepared from the product from Example 10a in accordance with Example 6.

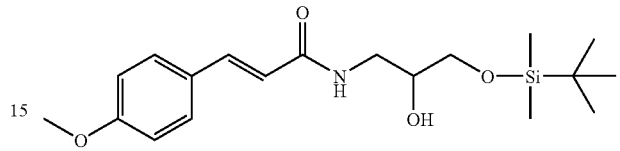

Yield: 86%.

C$_{19}$H$_{31}$NO$_4$Si; M=365.55 g/mol

R$_f$=0.49 (ethyl acetate:cyclohexane—1:2), as white crystals of m.p. 107-109° C.

¹H-NMR (300 MHz, DMSO-d$_6$): 7.92 (tr, J=5.62 Hz, NHCO), 7.46 (d, J=8.59 Hz, 2H, Ar—H), 7.32 (d, J=15.76 Hz, 1H, CH═CHCO), 6.92 (d, J=8.59 Hz, 2H, Ar—H), 6.53 (d, J=15.77 Hz, 1H, CH═CHCO), 4.88 (d, J=4.88, 1H, CHOH exchangeable with D$_2$O), 3.73 (s, 3H, OMe), 3.54, 3.47, 3.36, 3.03 (4m, 5H, NHCH$_2$CHCH$_2$OH), 0.8 (1s, 9H, 3Me), 0.01 (1s, 6H, 2Me).

¹³C-NMR (75 MHz, DMSO-d$_6$): 165.5, 160.2, 138.1, 128.9, 127.5, 119.8, 114.3, 70.2, 65.5, 55.2, 42.2, 25.8, 17.9, −5.4.

MS (FD): [M+] 365 (100).

UV-VIS (1 mg/100 ml; λ$_{max}$[nm], ε): 291.0 (0.481).

Example 13

N-[3-(tert-butyldimethylsilyloxy)-2-hydroxypropyl]-N-methyl-(E)-3-(4-methoxyphenyl)acrylamide is prepared from the product from Example 10b in accordance with Example 6.

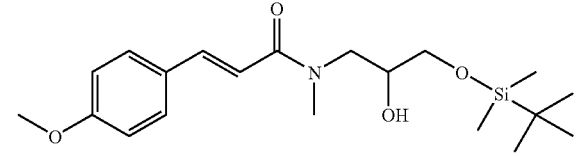

C$_{20}$H$_{33}$O$_4$NSi: 379 g/mol

Yield: 91%.

R$_f$=0.26 (ethyl acetate:cyclohexane—6:3), as white crystals of m.p. 82-83° C.

¹H-NMR (500 MHz, DMSO-d$_6$): 7.58 (d, J=8.59 Hz, 2H, Ar—H), 7.43 (d, J=15.76 Hz, 1H, CH═CHCO), 7.02 (d, J=15.77 Hz, 1H, CH═CHCO), 6.97 (d, J=8.59 Hz, 2H, Ar—H), 4.45 (s, 1H, OH exchangeable with D$_2$O), 3.83 (s, 3H, OMe), 3.74, 3.58, 3.42 (3m, 5H, NCH$_2$CHCH$_2$OH), 3.08 (s, 3H, NMe), 0.88 (1s, 9H, 3Me), 0.01 (1s, 6H, 2Me).

Example 14

N-[3-(tert-butyldimethylsilyloxy)-2-hydroxypropyl]-(E)-3-[4-(2-ethylhexyloxyphenyl)]acrylamide is prepared from the product from Example 10c in accordance with Example 6.

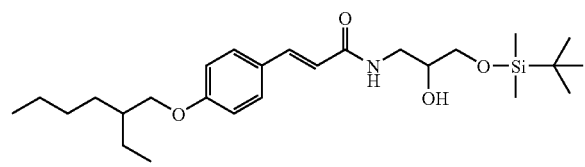

Yield: 91%.

$C_{26}H_{45}NO_4Si$; M=463.74 g/mol $R_f$=0.48 (ethyl acetate:cyclohexane—1:1), as colourless oil.

¹H-NMR (300 MHz, DMSO-$d_6$): 7.91 (tr, J=5.74 Hz, 1H, CONHCH₂), 7.42 (d, J=8.72 Hz, 2H, Ar—H), 7.30 (d, J=15.76 Hz, 1H, CH=CHCO), 6.91 (d, J=8.72 Hz, 2H, Ar—H), 6.53 (d, J=15.76 Hz, 1H, CH=CHCO), 4.86 (d, 1H, CHOH, exchangeable with D₂O), 3.82 (d, J=6.05 Hz, 2H, ArOCH₂CH), 3.44, 3.32 (2m, 4H, NHCH₂CHCH₂OSi), 3.01 (m, 1H, CH), 1.7, 1.45, 1.27, 0.85 (4m, 24H), 0.01 (s, 6H, SiMe₂).

MS (FD): [M⁺] 463 (61).

Example 15

N-[3-(tert-butyldimethylsilyloxy)-2-hydroxypropyl]-4-dimethylaminobenzamide is prepared from the product from Example 10d in accordance with Example 6.

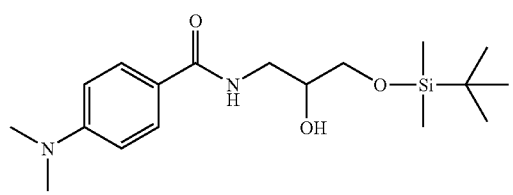

Yield: 88%.

$C_{18}H_{32}N_2O_3Si$; M=352.55.

$R_f$=0.30 (ethyl acetate:cyclohexane—1:1), as white crystals of m.p. 127-128° C.

¹H-NMR (300 MHz, DMSO-$d_6$): 7.98 (tr, J=5.60 Hz, 1H, NHCO), 7.69 (d, J=9.02 Hz, 2H, Ar—H), 6.66 (d, J=9.02 Hz, 2H, Ar—H), 4.87 (d, J=4.88 Hz, 1H, CHOH exchangeable with D₂O), 3.47 (d, J=5.47, 2H, CHCH₂OSi), 3.62, 3.36, 3.10 (3m, 3H, NHCH₂CH), 2.92 (s, 6H, NMe₂), 0.82, 0.00 (2s, 15H, 5Me).

MS (EI): [M⁺] 352 (6), 295 (13), 148 (100).

UV-VIS (1 mg/100 ml; $\lambda_{max}$[nm], ε): 301.0 (0.64).

Example 16

3-[4-({[3-(tert-butyldimethylsilyloxy)-2-hydroxypropyl]-methylamino}methyl)benzylidene]-4,7,7-trimethylbicyclo[2.2.1]heptan-2-one is prepared from the product from Example 11 in accordance with Example 6.

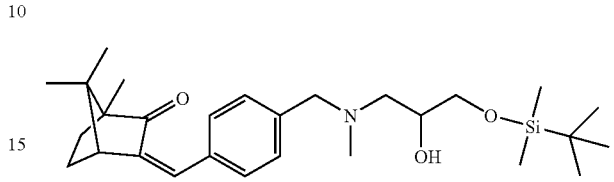

$C_{28}H_{45}O_3NSi$: 471 g/mol $R_f$=0.31 (ethyl acetate:cyclohexane—2:5), as white crystals of m.p. 56-57° C.

¹H-NMR (500 MHz, DMSO-$d_6$): 7.48 (d, J=8.19 Hz, 2H, Ar—H), 7.37 (d, J=8.19 Hz, 2H, Ar—H), 7.09 (s, 1H, C=CH), 4.45 (bs, 1H, CHOH, exchangeable with D₂O), 3.52, 3.48 (2m, 3H, NCH₂ and CHOH), 3.29 (s, 2H, Ar—CH₂), 3.13 (d, J=4.2 Hz, 1H, CH-camphor), 2.46 (dd, J=12.8, 4.9, 2H, CH₂OSi), 2.17, 2.18 (s and m, 4H, NMe and CH-camphor), 1.77, 1.46, 1.36 (3m, 3H, CH₂CH₂), 0.97, 0.93, 0.72 (3s, 3H+3H+3H, 3Me), 0.83 (s, 9H, CMe₃), 0.0 (s, 6H, SiMe₂).

¹³C-NMR (75 MHz, DMSO-$d_6$): 206.6, 141.3, 140.3, 133.5, 129.5, 129.0, 126.4, 69.2, 65.8, 61.9, 59.7, 56.3, 48.6, 46.1, 42.9, 30.0, 25.7, 25.5, 20.1, 17.9, 9.2.

MS (EI): [M⁺] 471 (2), 414 (7), 296 (83), 253 (100), 225 (12), 169 (5), 141 (7), 73 (7).

UV-VIS (1 mg/100 ml; $\lambda_{max}$[nm], ε): 297.0 (0.545).

Example 17

N-[3-(tert-butyldimethylsilyloxy)-2-oxopropyl]-(E)-3-(4-methoxyphenyl)acrylamide is prepared from the product from Example 12 in accordance with Example 7.

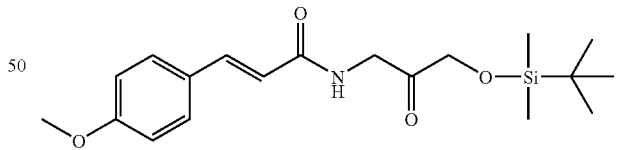

$C_{19}H_{29}NO_4Si$; M=363.53

$R_f$=0.63 (ethyl acetate:cyclohexane—1:2), as white crystals of m.p. 151-152° C.

¹H-NMR (300 MHz, DMSO-$d_6$): 8.16 (tr, J=5.62 Hz, 1H, NHCO), 7.46 (d, J=8.59 Hz, 2H, Ar—H), 7.32 (d, J=15.76 Hz, 1H, CH=CHCO), 6.90 (d, J=8.59 Hz, 2H, Ar—H), 6.54 (d, J=15.77 Hz, 1H, CH=CHCO), 4.31 (s, 2H, CH₂OSi), 4.05 (d, 2H, NHCH₂CO), 3.72 (s, 3H, OMe), 0.08 (1s, 9H, 3Me), 0.00 (1s, 6H, 2Me).

¹³C-NMR (75 MHz, DMSO-$d_6$): 205.3, 165.5, 160.3, 138.8, 129.1, 127.3, 119.0, 114.3, 67.5, 55.2, 45.6, 25.6, 17.9, −5.5.

MS (EI): [M+] 363 (7), 306 (38), 218 (6), 161 (100), 133 (14), 129 (22).
UV-VIS (1 mg/100 ml; $\lambda_{max}$[nm], $\epsilon$): 300.0 (0.843).

Example 18

N-[3-(tert-butyldimethylsilyloxy)-2-oxopropyl]-(E)-3-[4-(2-ethylhexyloxyphenyl)]acrylamide is prepared from the product from Example 14 in accordance with Example 7.

$C_{26}H_{43}NO_4Si$; M=461.72
$R_f$=0.45 (ethyl acetate:cyclohexane—1:2), as colourless oil.
$^1$H-NMR (300 MHz, DMSO-$d_6$): 8.22 (tr, J=5.74 Hz, 1H, CONHCH$_2$), 7.52 (d, J=8.72 Hz, 2H, Ar—H), 7.38 (d, J=15.76 Hz, 1H, CH=CHCO), 6.98 (d, J=8.72 Hz, 2H, Ar—H), 6.60 (d, J=15.76 Hz, 1H, CH=CHCO), 4.31 (s, 2H, CH$_2$OSi), 4.06 (d, J=5.74 Hz, 2H, NHCH$_2$CO), 3.81 (d, J=6.05 Hz, 2H, ArOCH$_2$CH), 1.7, 1.45, 1.27, 0.85 (4m, 24H), 0.05 (s, 6H, SiMe$_2$).
$^{13}$C-NMR (75 MHz, DMSO-$d_6$): 205.3, 165.5, 160.0, 138.8, 129.1, 127.1, 118.9, 114.8, 69.9, 67.4, 66.2, 38.5, 29.8, 28.3, 25.7, 23.2, 22.4, 17.9, 13.9, 10.8, −5.5.
MS (FD): [M+] 461 (72).

Example 19

N-[3-(tert-butyldimethylsilyloxy)-2-oxopropyl]-4-dimethylaminobenzamide is prepared from the product from Example 15 in accordance with Example 7.

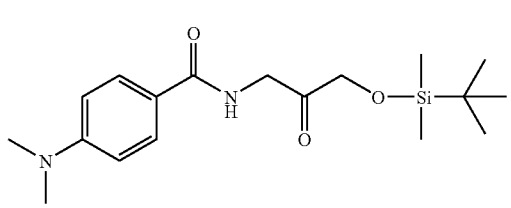

$C_{18}H_{30}N_2O_3Si$; M=350.54.
$R_f$=0.61 (ethyl acetate:cyclohexane—1:1), as white crystals.
$^1$H-NMR (300 MHz, DMSO-$d_6$): 8.28 (tr, J=5.60 Hz, 1H, NHCO), 7.70 (d, J=9.02 Hz, 2H, Ar—H), 6.65 (d, J=9.02 Hz, 2H, Ar—H), 4.34 (s, 2H, CH$_2$OSi), 4.33 (d, J=5.60 Hz, 2H, NHCH$_2$CO), 2.93 (s, 6H, NMe$_2$), 0.82, 0.00 (2s, 15H, 5Me).

$^{13}$C-NMR (75 MHz, DMSO-$d_6$): 205.1, 164.9, 152.4, 129.5, 119.4, 110.7, 67.5, 45.9, 42.7, 25.6, 17.9, −5.5.
UV-VIS (1 mg/100 ml; $\lambda_{max}$[nm], $\epsilon$): 312.0 (0.713).

Example 20

N-(3-hydroxy-2-oxopropyl)-(E)-3-(4-methoxyphenyl)acrylamide is prepared from the product from Example 17 in accordance with Example 3.

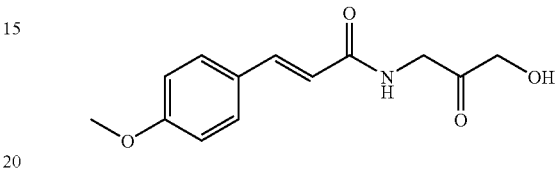

Yield: 95%
$C_{13}H_{15}NO_4$; M=249.27
$R_f$=0.32 (chloroform:methanol—9:1), as white crystals of m.p. 160-162° C.
$^1$H-NMR (300 MHz, DMSO-$d_6$): 8.24 (tr, J=5.62 Hz, 1H, NHCO), 7.54 (d, J=8.59 Hz, 2H, Ar—H), 7.39 (d, J=15.76 Hz, 1H, CH=CHCO), 6.98 (d, J=8.59 Hz, 2H, Ar—H), 6.63 (d, J=15.77 Hz, 1H, CH=CHCO), 5.28 (tr, J=5.98 Hz, 1H, OH, exchangeable with D$_2$O), 4.16 (d, 4H, NHCH$_2$COCH$_2$OH), 3.80 (s, 3H, OMe).
$^{13}$C-NMR (75 MHz, DMSO-$d_6$): 207.3, 165.5, 160.3, 138.8, 129.1, 127.3, 119.1, 114.3, 66.2, 55.2, 45.9.
MS (EI): [M+] 249 (11), 218 (15), 191 (6), 161 (100), 133 (16), 118 (4).
UV-VIS (1 mg/100 ml; $\lambda_{max}$[nm], $\epsilon$): 294.0 (0.941).

Example 21

N-(3-hydroxy-2-oxopropyl)-(E)-3-[4-(2-ethylhexyloxyphenyl)]acrylamide is prepared from the product from Example 18 in accordance with Example 3.

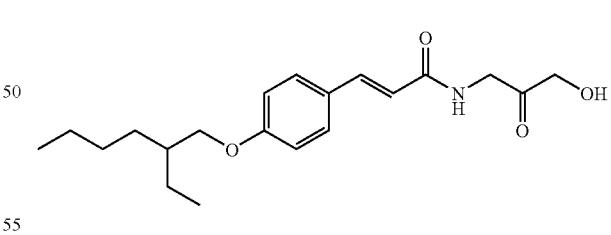

Yield: 93%
$C_{20}H_{29}NO_4$; M=347.46
$R_f$=0.46 (ethyl acetate:methanol—8:2), as white crystals of m.p. 155-157° C.
$^1$H-NMR (300 MHz, DMSO-$d_6$): 8.23 (tr, J=5.74 Hz, 1H, CONHCH$_2$), 7.52 (d, J=8.72 Hz, 2H, Ar—H), 7.38 (d, J=15.76 Hz, 1H, CH=CHCO), 6.98 (d, J=8.72 Hz, 2H, Ar—H), 6.62 (d, J=15.76 Hz, 1H, CH=CHCO), 5.29 (tr, J=6.10 Hz, 1H, OH, exchangeable with D$_2$O), 4.16 (2d, 4H, CONHCH$_2$COCH$_2$OH), 3.89 (d, J=6.05 Hz, 2H, ArOCH$_2$CH), 1.7, 1.45, 1.27, 0.85 (4m, 15H).

$^{13}$C-NMR (75 MHz, DMSO-d$_6$): 207.3, 165.5, 160.0, 138.8, 129.1, 127.1, 118.9, 114.8, 69.9, 66.2, 45.9, 38.5, 29.8, 28.3, 23.2, 22.4, 13.9, 10.8.

MS (EI): [M$^+$] 347 (26), 316 (14), 259 (55), 204 (36), 177 (18), 147 (100).

UV-VIS (1 mg/100 ml; λ$_{max}$[nm], ε): 307.5 (0.706).

Example 22

N-(3-hydroxy-2-oxopropyl)-4-dimethylaminobenzamide is prepared from the product from Example 19 in accordance with Example 3.

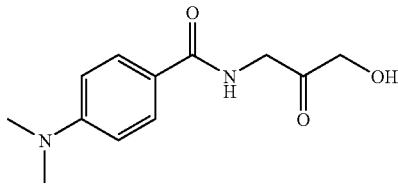

Yield: 95%
C$_{12}$H$_{16}$N$_2$O$_3$; M=236.27.
White crystals
$^1$H-NMR (300 MHz, DMSO-d$_6$): 8.28 (tr, J=5.60 Hz, 1H, NHCO), 7.73 (d, J=9.02 Hz, 2H, Ar—H), 6.72 (d, J=9.02 Hz, 2H, Ar—H), 5.27 (tr, J=6.10 Hz, 1H, OH, exchangeable with D$_2$O), 4.16 (m, 4H, CONHCH$_2$COCH$_2$OH), 2.93 (s, 6H, NMe$_2$).

UV-VIS (1 mg/100 ml; λ$_{max}$[nm], ε): 298.0 (0.575).

Example 23

Reaction of dihydroxyacetone (DHA) with (E)-(4-methoxy)cinnamyl chloride

DHA (90 mg, 1 mmol) is dissolved in abs. pyridine (10 ml) under a protective-gas atmosphere in a 50 ml round-bottomed flask, and 4-dimethylaminopyridine (10 mg) is added. (E)-(4-methoxy)cinnamyl chloride (0.59 mg, 3 mmol) is then added in one portion, and the mixture is stirred at room temperature for 10 min and at 90-100° C. for 1 h. After the mixture has been cooled to room temperature, the solvent is distilled off, and the crude product which remains is taken up in water (25 ml) and extracted with dichloromethane (3×10 ml). The combined organic phases are washed with water (2×10 ml) and dried over magnesium sulfate. The crude product remaining after evaporation of the dichloromethane in vacuo is recrystallised from ethanol (10 ml) and dried in vacuo. Yield 380 mg (92%) of 1,3-bis-[(E)-3-(4-methoxyphenyl)-2-propenoyloxy]-2-oxopropane as white solid of m.p. 146-148° C.

1,3-Bis-[(E)-3-(4-methoxyphenyl)-2-propenoyloxy]-2-oxopropane

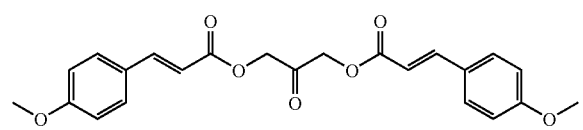

C$_{23}$H$_{22}$O$_7$: 410 g/mol
$^1$H-NMR (300 MHz, DMSO-d$_6$): 7.73 (d, J=8.76, 4H, Ar—H), 7.69 (d, J=15.95, 2H, CH═CHCO), 7.00 (d, J=8.76, 4H, Ar—H), 6.60 (d, J=15.95, 2H, Ar—CH═CH), 5.05 (s, 4H, CH$_2$), 3.81 (s, 6H, OCH$_3$).

$^{13}$C-NMR (75 MHz, DMSO-d$_6$): 198.6, 165.6, 161.3, 145.4, 130.3, 126.4, 114.3, 114.2, 65.8, 55.3.

MS (EI): [M$^+$] 410 (20), 219 (20), 161 (100), 133 (6).

UV-VIS (1 mg/100 ml, λ$_{max}$[nm], ε): 307.0 (1.140).

Example 23a 1,3-Bis-[(E)-3-(4-(2-ethylhexyloxyphenyl)-2-propenoyloxy]-2-oxopropane is obtained analogously to Example 23

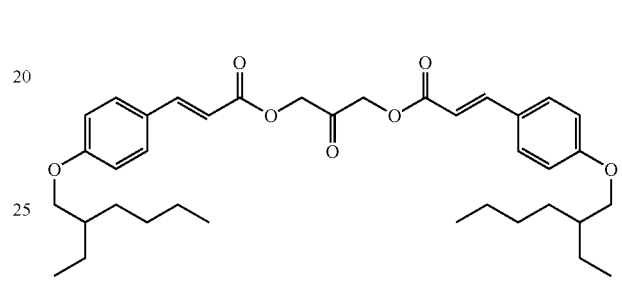

C$_{37}$H$_{50}$O$_7$; M=606.80
as white crystals of m.p. 77-79° C. (ethanol).
$^1$H-NMR (300 MHz, CDCl$_3$): 7.76 (d, J=15.95, 2H, CH═CHCO), 7.48 (d, J=8.76, 4H, Ar—H), 6.92 (d, J=8.76, 4H, Ar—H), 6.33 (d, J=15.95, 2H, Ar—CH═CH), 5.05 (s, 4H, CH$_2$), 3.87 (d, J=5.73 Hz, 4H, OCH$_2$), 1.8-0.9 (4m, 30H, aliphatic H).

MS (EI): [M$^+$] 606 (2), 276 (19), 164 (100), 147 (15).

UV-VIS (1 mg/100 ml, λ$_{max}$[nm], ε): 301.0 (0.947).

Example 23b 1,3-Bis-(2-cyano-3,3-diphenylacryloyloxy)-2-oxopropane is obtained analogously to Example 23.

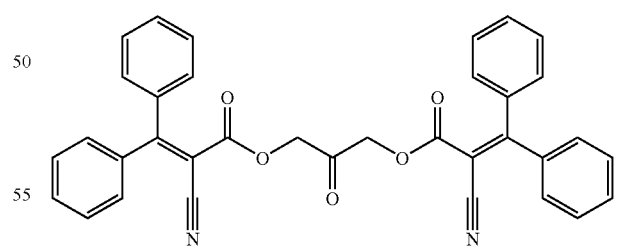

Yield: 94%.
C$_{35}$H$_{24}$N$_2$O$_5$; M=552.59
as white crystals of m.p. 209° C.
$^1$H-NMR (300 MHz, DMSO-d$_6$): 7.23 (m, 4H, Ar—H), 7.37-7.65 (m, 16H, Ar—H), 4.95 (s, 4H, OCH$_2$CO).

$^{13}$C-NMR (75 MHz, DMSO-d$_6$): 196.5, 170.8, 160.7, 138.4, 137.8, 131.5, 130.5, 129.8, 129.8, 128.6, 128.1, 116.6, 102.5, 67.1.

MS (FD): 552 (75) [M⁺].
UV-VIS (1 mg/100 ml, $\lambda_{max}$[nm], ε): 304.0 (0.031).

Example 24

Reaction of 1-(tert-butyldimethylsilyloxy)-3-hydroxy-2-oxopropane with 4-dimethylaminobenzoyl chloride 4-Dimethylaminobenzoyl chloride (0.4 g, 2 mmol) is added to a solution of 1-(tert-butyldimethylsilyloxy)-3-hydroxy-2-oxopropane (J. Schröder, P. Welzel, *Tetrahedron* 1994, 50, 6839) (2 mmol) in abs. pyridine (20 ml). The mixture is stirred at RT for 1 h and at 60-70° C. for 2 h. The solvent is removed, and the crude product which remains is taken up in water (100 ml) and extracted with ethyl acetate (3×20 ml). The combined organic phases are washed with 100 ml of saturated sodium chloride solution and dried over magnesium sulfate. The residue remaining after evaporation of the ethyl acetate is worked up by column chromatography, giving 1-(tert-butyldimethylsilyloxy)-2-oxopropyl 4-dimethylaminobenzoate

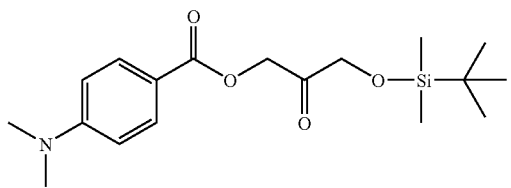

Yield: 84% (590 mg).
$C_{18}H_{29}NO_4Si$; M=351.52.
$R_f$=0.57 (ethyl acetate:cyclohexane—1:1), as white crystals of m.p. 91-92° C.

¹H-NMR (300 MHz, DMSO-d₆): 7.70 (d, J=9.02 Hz, 2H, Ar—H), 6.65 (d, J=9.02 Hz, 2H, Ar—H), 4.92 (s, 2H, OCH₂CO), 4.34 (s, 2H, CH₂OSi), 2.93 (s, 6H, NMe₂), 0.80, 0.00 (2s, 15H, 5Me).
¹³C-NMR (75 MHz, DMSO-d₆): 203.4, 165.2, 153.4, 130.9, 114.9, 110.7, 67.0, 65.8, 39.4, 25.6, 17.9, −5.6.
MS (EI): [M⁺] 251 (32), 294 (48), 164 (24), 148 (100), 129 (12), 117 (16), 77 (9), 73 (41).
UV-VIS (1 mg/100 ml, $\lambda_{max}$[nm], ε): 299.0 (0.67).

Example 25

N-[3-(tert-butyldimethylsilyloxy)-2-oxopropyl]-4-dimethylaminobenzamide is obtained in accordance with Example 7

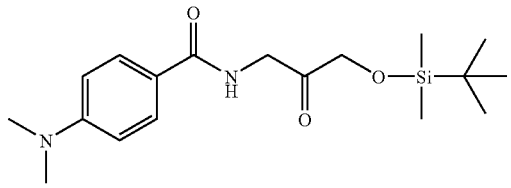

$C_{18}H_{30}N_2O_3Si$; M=350.54.
$R_f$=0.61 (ethyl acetate:cyclohexane—1:1), as white crystals.
¹H-NMR (300 MHz, DMSO-d₆): 8.28 (tr, J=5.60 Hz, 1H, NHCO), 7.70 (d, J=9.02 Hz, 2H, Ar—H), 6.65 (d, J=9.02 Hz, 2H, Ar—H), 4.34 (s, 2H, CH₂OSi), 4.33 (d, J=5.60 Hz, 2H, NHCH₂CO), 2.93 (s, 6H, NMe₂), 0.82, 0.00 (2s, 15H, 5Me).
¹³C-NMR (75 MHz, DMSO-d₆): 205.1, 164.9, 152.4, 129.5, 119.4, 110.7, 67.5, 45.9, 42.7, 25.6, 17.9, −5.5.
UV-VIS (1 mg/100 ml, $\lambda_{max}$[nm], ε): 312.0 (0.713).

Example 26

UV Absorption

UV absorption data are shown in the following table:

| Structural formula | Solvent for spectrosc. | c (mg/100 ml) | UVA (400-320 nm) max. abs | UVA max. at λ [nm] | UVB (280-320 nm) max. abs | UVB max. at λ [nm] |
|---|---|---|---|---|---|---|
| | 2-Propanol | 1 | | | 0.107 | 300.67 |
| | 2-Propanol | 1 | | | 0.893 | 311.33 |

| Structural formula | Solvent for spectrosc. | c (mg/ 100 ml) | UVA (400-320 nm) max. abs | UVA max. at λ [nm] | UVB (280-320 nm) max. abs | UVB max. at λ [nm] |
|---|---|---|---|---|---|---|
| 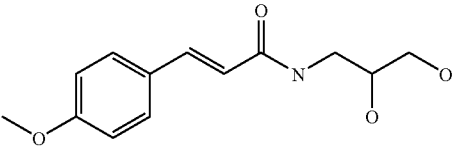 | 2-Propanol | 1 | — | — | 0.936 | 292.00 |
| 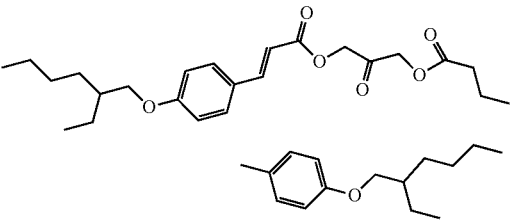 | 2-Propanol | 1 | — | — | 0.761 | 307.00 |
| 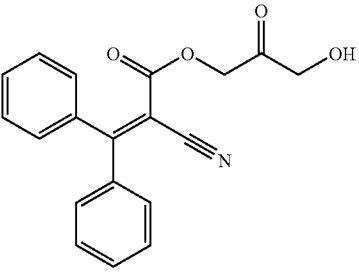 | 2-Propanol | 1 | | | 0.375 | 303.0 |
| 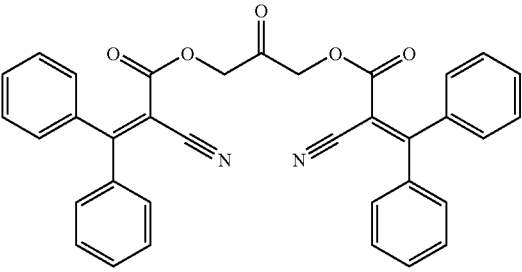 | 2-Propanol | 1 | | | 0.031 | 304.0 |
| 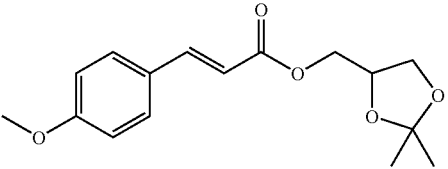 | 2-Propanol | 1 | | | 0.796 | 306.0 |
| 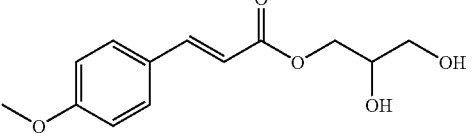 | 2-Propanol | 1 | | | 0.881 | 302.0 |
| 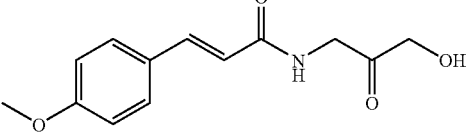 | 2-Propanol | 1 | | | 0.941 | 294.0 |

-continued

| Structural formula | Solvent for spectrosc. | c (mg/ 100 ml) | UVA (400-320 nm) max. abs | UVA max. at λ [nm] | UVB (280-320 nm) max. abs | UVB max. at λ [nm] |
|---|---|---|---|---|---|---|
| [structure: 4-dimethylamino-N-(2,3-dihydroxypropyl)benzamide] | 2-Propanol | 1 | | | 0.947 | 301.0 |
| [structure: 4-dimethylaminobenzoic acid 3-hydroxy-2-oxopropyl ester] | 2-Propanol | 1 | | | 1.213 | 311.0 |
| [structure: 4-dimethylamino-N-[3-(tert-butyldimethylsilyloxy)-2-hydroxypropyl]benzamide] | 2-Propanol | 1 | | | 0.64 | 301.0 |
| [structure: 4-dimethylamino-N-(3-hydroxy-2-oxopropyl)benzamide] | 2-Propanol | 1 | | | 0.575 | 298.0 |
| [structure: 4-dimethylamino-N-[3-(tert-butyldimethylsilyloxy)-2-oxopropyl]benzamide] | 2-Propanol | 1 | | | 0.713 | 312.0 |
| [structure: 2-hydroxy-4-(2,3-dihydroxypropoxy)benzophenone] | 2-Propanol | 1 | 0.363 | 327.5 | 0.537 | 287.9 |
| [structure: 2-hydroxy-4-[(2,2-dimethyl-1,3-dioxolan-4-yl)methoxy]benzophenone] | 2-Propanol | 1 | 0.312 | 328.3 | 0.473 | 286.1 |

| Structural formula | Solvent for spectrosc. | c (mg/ 100 ml) | UVA (400-320 nm) max. abs | UVA max. at λ [nm] | UVB (280-320 nm) max. abs | UVB max. at λ [nm] |
|---|---|---|---|---|---|---|
| | 2-Propanol | 1 | | | 0.688 | 307.0 |
| | 2-Propanol | 1 | | | 0.706 | 307.5 |
| | 2-Propanol | 1 | | | 0.692 | 298.0 |
| | 2-Propanol | 1 | | | 0.615 | 298.0 |
| | 2-Propanol | 1 | | | 0.694 | 289 |
| | 2-Propanol | 1 | | | 0.914 | 289 |
| | 2-Propanol | 1 | | | 0.874 | 296 |

| Structural formula | Solvent for spectrosc. | c (mg/ 100 ml) | UVA (400- 320 nm) max. abs | UVA max. at λ [nm] | UVB (280- 320 nm) max. abs | UVB max. at λ [nm] |
|---|---|---|---|---|---|---|
| [structure] | 2-Propanol | 1 | | | 0.715 | 292 |
| [structure] | 2-Propanol | 1 | | | 0.481 | 291 |
| [structure] | 2-Propanol | 1 | | | 0.545 | 297 |
| [structure] | 2-Propanol | 1 | | | 0.711 | 296 |

Example 27

Lotion (W/O) for Application to the Skin

| | | % by wt. |
|---|---|---|
| A | Polyglyceryl 2-dipolyhydroxystearate | 5.0 |
| | Beeswax | 0.5 |
| | Zinc stearate | 0.5 |
| | Hexyl laurate | 9.0 |
| | Cetyl isononanoate | 6.0 |
| | Shea butter | 0.5 |
| | DL-α-tocopherol acetate | 1.0 |
| | Product from one of Examples 1-25 | 0.5 |
| B | Glycerin | 5.0 |
| | Magnesium sulfate heptahydrate | 1.0 |
| | Preservatives | q.s. |
| | Water, demineralised | to 100 |

Preparation

Phase A is warmed to 75° C. and phase B to 80° C. Phase B is slowly added to phase A with stirring. After homogenisation, the mixture is cooled with stirring. Perfume substances are added at a temperature of 40° C.

The following are used as preservatives:
0.05% of propyl 4-hydroxybenzoate
0.15% of methyl 4-hydroxybenzoate

Example 28

Lotion (W/O) for Application to the Skin

| | | % by wt. |
|---|---|---|
| A | Polyglyceryl 2-dipolyhydroxystearate | 5.0 |
| | Beeswax | 0.5 |
| | Zinc stearate | 0.5 |
| | Hexyl laurate | 9.0 |
| | Cetyl isononanoate | 6.0 |
| | Shea butter | 0.5 |
| | DL-α-tocopherol acetate | 1.0 |
| B | Product from one of Examples 1-25 | 1.0 |
| | Glycerin | 5.0 |
| | Magnesium sulfate heptahydrate | 1.0 |
| | Preservatives | q.s. |
| | Water, demineralised | to 100 |

Preparation

Phase A is warmed to 75° C. and phase B to 80° C. Phase B is slowly added to phase A with stirring. After homogenisation, the mixture is cooled with stirring. Perfume substances are added at a temperature of 40° C.

The following are used as preservatives:
0.05% of propyl 4-hydroxybenzoate
0.15% of methyl 4-hydroxybenzoate

Example 29

Lotion (W/O) for Application to the Skin

|   |                                      | % by wt. |
|---|--------------------------------------|----------|
| A | Product from one of Examples 1-25    | 1.0      |
|   | Polyglyceryl 2-dipolyhydroxystearate | 5.0      |
|   | Beeswax                              | 0.5      |
|   | Zinc stearate                        | 0.5      |
|   | Hexyl laurate                        | 9.0      |
|   | Cetyl isononanoate                   | 6.0      |
|   | Shea butter                          | 0.5      |
|   | DL-α-tocopherol acetate              | 1.0      |
|   | 5,7-Dihydroxy-2-methylchromen-4-one  | 1.0      |
| B | Glycerin                             | 5.0      |
|   | Magnesium sulfate heptahydrate       | 1.0      |
|   | Preservatives                        | q.s.     |
|   | Water, demineralised                 | to 100   |

Preparation

Phase A is warmed to 75° C. and phase B to 80° C. Phase B is slowly added to phase A with stirring. After homogenisation, the mixture is cooled with stirring. Perfume substances are added at a temperature of 40° C.

The following are used as preservatives:
0.05% of propyl 4-hydroxybenzoate
0.15% of methyl 4-hydroxybenzoate

Example 30

A Cream (O/W) Comprising Ectoine is Prepared from the Following Components

|   |                                   |     | % by wt. |
|---|-----------------------------------|-----|----------|
| A | Paraffin, liquid                  | (1) | 8.0      |
|   | Isopropyl myristate               | (1) | 4.0      |
|   | Mirasil CM5                       | (2) | 3.0      |
|   | Stearic acid                      | (1) | 3.0      |
|   | Arlacel 165 V                     | (3) | 5.0      |
|   | Product from one of Examples 1-25 |     | 1.0      |
| B | Glycerin (87%)                    | (1) | 3.0      |
|   | Germaben II                       | (4) | 0.5      |
|   | Water, demineralised              |     | to 100   |
| C | RonaCare ™ ectoine                | (1) | 1.0      |

Preparation

Firstly, phases A and B are warmed separately to 75° C. Phase A is then slowly added to phase B with stirring, and stirring is continued until a homogeneous mixture has formed. After homogenisation of the emulsion, the mixture is cooled to 30° C. with stirring. The mixture is subsequently warmed to 35° C., phase C is added, and the mixture is stirred to homogeneity.

Sources of supply
(1) Merck KGaA
(2) Rhodia
(3) Uniqema
(4) ISP

Example 31

Topical Composition as W/O Emulsion

|   |                                   |     | % by wt. |
|---|-----------------------------------|-----|----------|
| A | Isolan PDI                        | (2) | 3.0      |
|   | Paraffin oil, liq.                | (1) | 17.0     |
|   | Isopropyl myristate               |     | 5.0      |
|   | Beeswax                           |     | 0.2      |
|   | Cutina HR                         | (2) | 0.3      |
|   | Product from one of Examples 1-25 |     | 1.0      |
| B | Water, demineralised              |     | to 100   |
|   | Glycerin (87%)                    |     | 4.0      |
|   | Magnesium sulfate                 |     | 1.0      |
|   | Germaben II-E                     | (3) | 1.0      |
| C | RonaCare ™ LPO                    | (1) | 2.0      |

Preparation

Phases A and B are warmed to 75° C. Phase B is added to phase A with stirring. The mixture is subsequently homogenised for 2 min. at 9000 rpm using a Turrax. The resultant mixture is cooled to 30 to 35° C., and C is stirred in.

Sources of supply
(1) Merck KGaA
(2) Goldschmidt AG
(3) ISP

Example 32

Compositions

Illustrative formulations for cosmetic compositions which comprise compounds selected from Examples 1-25 are indicated below. The compounds are named here corresponding to the details in the description. In addition, the INCI names of the commercially available compounds are indicated.

UV Pearl, OMC stands for the composition having the INCI name:

Water (for EU: Aqua), Ethylhexyl Methoxycinnamate, Silica, PVP, Chlorophenesin, BHT; this composition is commercially available from Merck KGaA, Darmstadt, under the name Eusolex®UV Pearl™OMC.

The other UV Pearl products indicated in the tables each have an analogous composition, with OMC being replaced by the UV filters indicated.

TABLE 1

| W/O emulsions (numbers in % by weight) | | | | | | | | | | |
|---|---|---|---|---|---|---|---|---|---|---|
| | 1-1 | 1-2 | 1-3 | 1-4 | 1-5 | 1-6 | 1-7 | 1-8 | 1-9 | 1-10 |
| Titanium dioxide | | 2 | 5 | | | | | | | 3 |
| 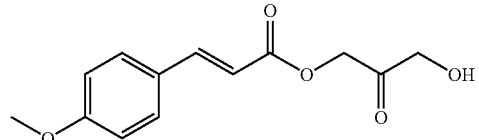 | 5 | 3 | 2 | 1 | 2 | | | | 1 | 1 |
| 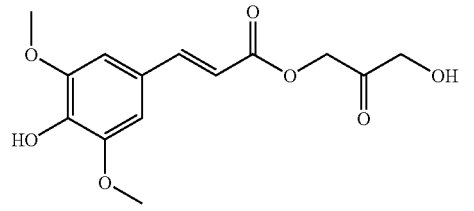 | | | | | | 1 | 2 | 1 | | |
| Zinc oxide | | | | | | | | 5 | 2 | |
| UV-Pearl, OMC | 30 | 15 | 15 | 15 | 15 | 15 | 15 | 15 | 15 | 15 |
| Polyglyceryl-3-Dimerate | 3 | 3 | 3 | 3 | 3 | 3 | 3 | 3 | 3 | 3 |
| Cera Alba | 0.3 | 0.3 | 0.3 | 0.3 | 0.3 | 0.3 | 0.3 | 0.3 | 0.3 | 0.3 |
| Hydrogenated Castor Oil | 0.2 | 0.2 | 0.2 | 0.2 | 0.2 | 0.2 | 0.2 | 0.2 | 0.2 | 0.2 |
| Paraffinium Liquidum | 7 | 7 | 7 | 7 | 7 | 7 | 7 | 7 | 7 | 7 |
| Caprylic/Capric Triglyceride | 7 | 7 | 7 | 7 | 7 | 7 | 7 | 7 | 7 | 7 |
| Hexyl Laurate | 4 | 4 | 4 | 4 | 4 | 4 | 4 | 4 | 4 | 4 |
| PVP/Eicosene Copolymer | 2 | 2 | 2 | 2 | 2 | 2 | 2 | 2 | 2 | 2 |
| Propylene Glycol | 4 | 4 | 4 | 4 | 4 | 4 | 4 | 4 | 4 | 4 |
| Magnesium Sulfate | 0.6 | 0.6 | 0.6 | 0.6 | 0.6 | 0.6 | 0.6 | 0.6 | 0.6 | 0.6 |
| Tocopherol | 0.5 | 0.5 | 0.5 | 0.5 | 0.5 | 0.5 | 0.5 | 0.5 | 0.5 | 0.5 |
| Tocopheryl Acetate | 0.5 | 0.5 | 0.5 | 0.5 | 0.5 | 0.5 | 0.5 | 0.5 | 0.5 | 0.5 |
| Cyclomethicone | 0.5 | 0.5 | 0.5 | 0.5 | 0.5 | 0.5 | 0.5 | 0.5 | 0.5 | 0.5 |
| Propylparabene | 0.05 | 0.05 | 0.05 | 0.05 | 0.05 | 0.05 | 0.05 | 0.05 | 0.05 | 0.05 |
| Methylparabene | 0.15 | 0.15 | 0.15 | 0.15 | 0.15 | 0.15 | 0.15 | 0.15 | 0.15 | 0.15 |
| Water | to 100 | to 100 | to 100 | to 100 | to 100 | to 100 | to 100 | to 100 | to 100 | to 100 |

| | 1-11 | 1-12 | 1-13 | 1-14 | 1-15 | 1-16 | 1-17 | 1-18 |
|---|---|---|---|---|---|---|---|---|
| Titanium dioxide | 3 | | 2 | | 3 | | 2 | 5 |
| Benzylidene malonate polysiloxane | | 1 | 0.5 | | | | | |
| Methylene Bis-Benztriazolyl Tetramethylbutylphenol | 1 | 1 | 0.5 | | | | | |
| 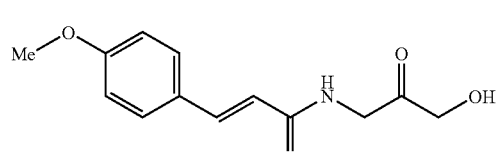 | 5 | 3 | 2 | 5 | 1 | 3 | 7 | 2 |
| Polyglyceryl-3-Dimerate | 3 | 3 | 3 | 3 | | | | |
| Cera Alba | 0.3 | 0.3 | 0.3 | 0.3 | 2 | 2 | 2 | 2 |
| Hydrogenated Castor Oil | 0.2 | 0.2 | 0.2 | 0.2 | | | | |
| Paraffinium Liquidum | 7 | 7 | 7 | 7 | | | | |
| Caprylic/Capric Triglyceride | 7 | 7 | 7 | 7 | | | | |
| Hexyl Laurate | 4 | 4 | 4 | 4 | | | | |
| PVP/Eicosene Copolymer | 2 | 2 | 2 | 2 | | | | |
| Propylene Glycol | 4 | 4 | 4 | 4 | | | | |
| Magnesium Sulfate | 0.6 | 0.6 | 0.6 | 0.6 | | | | |
| Tocopherol | 0.5 | 0.5 | 0.5 | 0.5 | | | | |
| Tocopheryl Acetate | 0.5 | 0.5 | 0.5 | 0.5 | 1 | 1 | 1 | 1 |
| Cyclomethicone | 0.5 | 0.5 | 0.5 | 0.5 | | | | |
| Propylparabene | 0.05 | 0.05 | 0.05 | 0.05 | 0.05 | 0.05 | 0.05 | 0.05 |
| Methylparabene | 0.15 | 0.15 | 0.15 | 0.15 | 0.15 | 0.15 | 0.15 | 0.15 |
| Dicocoyl Pentyerythrityl Citrate (and) Sorbitan Sesquioleate (and) Cera Alba (and) Aluminium Stearate | | | | | 6 | 6 | 6 | 6 |
| PEG-7 Hydrogenated Castor Oil | | | | | 1 | 1 | 1 | 1 |
| Zinc Stearate | | | | | 2 | 2 | 2 | 2 |

TABLE 1-continued

| | | | | | | | | |
|---|---|---|---|---|---|---|---|---|
| Oleyl Erucate | | | | | 6 | 6 | 6 | 6 |
| Decyl Oleate | | | | | 6 | 6 | 6 | 6 |
| Dimethicone | | | | | 5 | 5 | 5 | 5 |
| Tromethamine | | | | | 1 | 1 | 1 | 1 |
| Glycerin | | | | | 5 | 5 | 5 | 5 |
| Allantoin | | | | | 0.2 | 0.2 | 0.2 | 0.2 |
| Water | to 100 | to 100 | to 100 | to 100 | to 100 | to 100 | to 100 | to 100 |

| | 1-19 | 1-20 | 1-21 | 1-22 | 1-23 | 1-24 | 1-25 | 1-26 | 1-27 | 1-28 | 1-29 |
|---|---|---|---|---|---|---|---|---|---|---|---|
| Titanium dioxide | | 2 | 5 | | | | | | | 3 | 3 |
| Benzylidene malonate polysiloxane | | | | 1 | | | | | 1 | 1 | |
| Zinc oxide | | | | | | | 5 | 2 | | | |

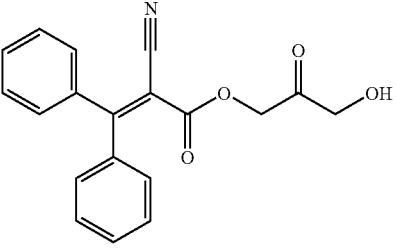

| | 1-19 | 1-20 | 1-21 | 1-22 | 1-23 | 1-24 | 1-25 | 1-26 | 1-27 | 1-28 | 1-29 |
|---|---|---|---|---|---|---|---|---|---|---|---|
| | 5 | 5 | 5 | 5 | 7 | 5 | 5 | 5 | 5 | 5 | 8 |
| UV-Pearl, OCR | | 10 | | | | | | | | | 5 |
| UV-Pearl, EthylhexylDimethylPABA | | | 10 | | | | | | | | |
| UV-Pearl, Homosalate | | | | 10 | | | | | | | |
| UV-Pearl, Ethylhexyl salicylate | | | | | 10 | | | | | | |
| UV-Pearl, OMC, BP-3 | | | | | | 10 | | | | | |
| UV-Pearl, OCR, BP-3 | | | | | | | 10 | | | | |
| UV-Pearl, Ethylhexyl Dimethyl PABA, BP-3 | | | | | | | | 10 | | | |
| UV-Pearl, Homosalate, BP-3 | | | | | | | | | 10 | | |
| UV-Pearl, Ethylhexyl salicylate, BP-3 | | | | | | | | | | 10 | |

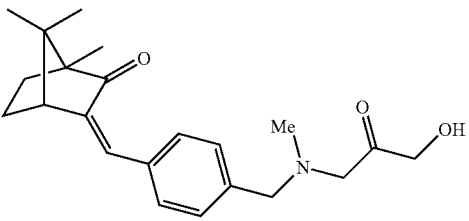

| | 1-19 | 1-20 | 1-21 | 1-22 | 1-23 | 1-24 | 1-25 | 1-26 | 1-27 | 1-28 | 1-29 |
|---|---|---|---|---|---|---|---|---|---|---|---|
| | | | | | | | | | | | 2 |
| UV-Pearl OMC, 4-Methylbenzylidene Camphor | 25 | | | | | | | | | | |
| Polyglyceryl-3-Dimerate | 3 | 3 | 3 | 3 | 3 | 3 | 3 | 3 | 3 | 3 | 3 |
| Cera Alba | 0.3 | 0.3 | 0.3 | 0.3 | 0.3 | 0.3 | 0.3 | 0.3 | 0.3 | 0.3 | 0.3 |
| Hydrogenated Castor Oil | 0.2 | 0.2 | 0.2 | 0.2 | 0.2 | 0.2 | 0.2 | 0.2 | 0.2 | 0.2 | 0.2 |
| Paraffinium Liquidum | 7 | 7 | 7 | 7 | 7 | 7 | 7 | 7 | 7 | 7 | 7 |
| Caprylic/Capric Triglyceride | 7 | 7 | 7 | 7 | 7 | 7 | 7 | 7 | 7 | 7 | 7 |
| Hexyl Laurate | 4 | 4 | 4 | 4 | 4 | 4 | 4 | 4 | 4 | 4 | 4 |
| PVP/Eicosene Copolymer | 2 | 2 | 2 | 2 | 2 | 2 | 2 | 2 | 2 | 2 | 2 |
| Propylene Glycol | 4 | 4 | 4 | 4 | 4 | 4 | 4 | 4 | 4 | 4 | 4 |
| Magnesium Sulfate | 0.6 | 0.6 | 0.6 | 0.6 | 0.6 | 0.6 | 0.6 | 0.6 | 0.6 | 0.6 | 0.6 |
| Tocopherol | 0.5 | 0.5 | 0.5 | 0.5 | 0.5 | 0.5 | 0.5 | 0.5 | 0.5 | 0.5 | 0.5 |
| Tocopheryl Acetate | 0.5 | 0.5 | 0.5 | 0.5 | 0.5 | 0.5 | 0.5 | 0.5 | 0.5 | 0.5 | 0.5 |
| Cyclomethicone | 0.5 | 0.5 | 0.5 | 0.5 | 0.5 | 0.5 | 0.5 | 0.5 | 0.5 | 0.5 | 0.5 |
| Propylparaben | 0.05 | 0.05 | 0.05 | 0.05 | 0.05 | 0.05 | 0.05 | 0.05 | 0.05 | 0.05 | 0.05 |
| Methylparaben | 0.15 | 0.15 | 0.15 | 0.15 | 0.15 | 0.15 | 0.15 | 0.15 | 0.15 | 0.15 | 0.15 |
| Water | | | | | | to 100 | | | | | |

TABLE 2

| O/W emulsions, numbers in % by weight | | | | | | | | | | |
|---|---|---|---|---|---|---|---|---|---|---|
| | 2-1 | 2-2 | 2-3 | 2-4 | 2-5 | 2-6 | 2-7 | 2-8 | 2-9 | 2-10 |
| Titanium dioxide | | 2 | 5 | | | | | | | 3 |
| Methylene Bis-Benztriazolyl Tetramethylbutylphenol | | | | | | 1 | 2 | 1 | | |
| (sinapoyl glycolate structure) | | | | 1 | 2 | | | | 1 | 1 |
| 4'-Methoxy-6-hydroxyflavon | 1 | 3 | | 2 | | 5 | | 5 | 2 | |
| (2-ethylhexyloxy cinnamoyl amide structure) | 5 | 5 | 5 | 5 | 5 | 5 | 5 | 5 | 5 | 5 |
| (methoxy cinnamoyl N-methyl amide structure) | 1 | 5 | 4 | | 6 | | 7 | | 2 | 1 |
| (methoxy cinnamate glycolate structure) | | 2 | | 3 | 4 | 3 | | 2 | | |
| (camphor benzyl ether structure) | 1 | 3 | | 3 | 3 | | 3 | 3 | 3 | |
| Stearyl Alcohol (and) Steareth-7 (and) Steareth-10 | 3 | 3 | 3 | 3 | 3 | 3 | 3 | 3 | 3 | 3 |
| Glyceryl Stearate (and) Ceteth-20 | 3 | 3 | 3 | 3 | 3 | 3 | 3 | 3 | 3 | 3 |
| Glyceryl Stearate | 3 | 3 | 3 | 3 | 3 | 3 | 3 | 3 | 3 | 3 |
| Microwax | 1 | 1 | 1 | 1 | 1 | 1 | 1 | 1 | 1 | 1 |
| Cetearyl Octanoate | 11.5 | 11.5 | 11.5 | 11.5 | 11.5 | 11.5 | 11.5 | 11.5 | 11.5 | 11.5 |
| Caprylic/Capric Triglyceride | 6 | 6 | 6 | 6 | 6 | 6 | 6 | 6 | 6 | 6 |
| Oleyl Oleate | 6 | 6 | 6 | 6 | 6 | 6 | 6 | 6 | 6 | 6 |
| Propylene Glycol | 4 | 4 | 4 | 4 | 4 | 4 | 4 | 4 | 4 | 4 |
| Glyceryl Stearate SE | | | | | | | | | | |
| Stearic Acid | | | | | | | | | | |
| Persea Gratissima | | | | | | | | | | |
| Propylparabene | 0.05 | 0.05 | 0.05 | 0.05 | 0.05 | 0.05 | 0.05 | 0.05 | 0.05 | 0.05 |
| Methylparabene | 0.15 | 0.15 | 0.15 | 0.15 | 0.15 | 0.15 | 0.15 | 0.15 | 0.15 | 0.15 |
| Tromethamine | | | 1.8 | | | | | | | |
| Glycerin | | | | | | | | | | |
| Water | to 100 | to 100 | to 100 | to 100 | to 100 | to 100 | to 100 | to 100 | to 100 | to 100 |

TABLE 2-continued
|  | 2-11 | 2-12 | 2-13 | 2-14 | 2-15 | 2-16 | 2-17 | 2-18 |
|---|---|---|---|---|---|---|---|---|
| Titanium dioxide |  | 3 |  | 2 |  |  | 2 | 5 |
| 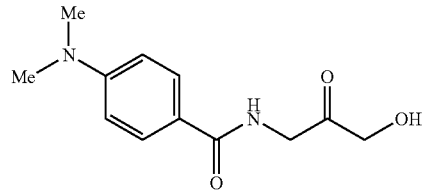 |  |  | 1 | 0.5 |  |  |  |  |
| Methylene Bis-Benztriazolyl Tetramethylbutylphenol |  | 1 | 1 | 0.5 |  |  |  |  |
| 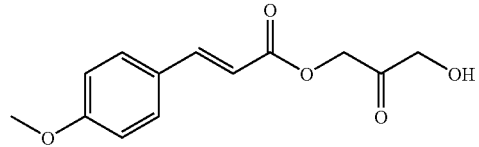 |  |  |  |  | 1 | 2 |  |  |
| 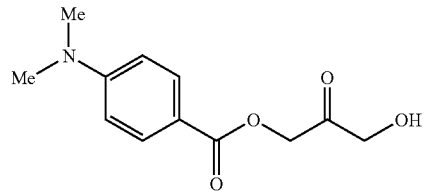 |  | 1 | 3 | 2 |  | 5 |  | 5 |
| 2-Carboxyl-7-hydroxy-chromen-4-on | 5 | 5 | 5 | 5 | 5 | 5 | 5 | 5 |
| 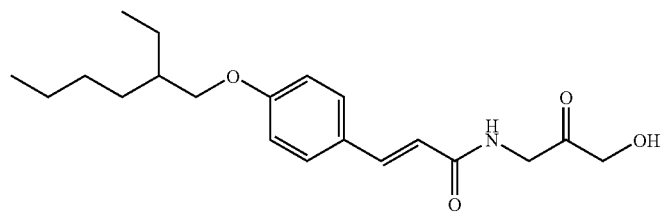 | 1 | 5 | 4 |  | 6 |  | 7 |  |
| Zinc oxide |  |  |  | 2 |  |  |  |  |
| UV-Pearl, OMC | 15 | 15 | 15 | 30 | 30 | 30 | 15 | 15 |
| 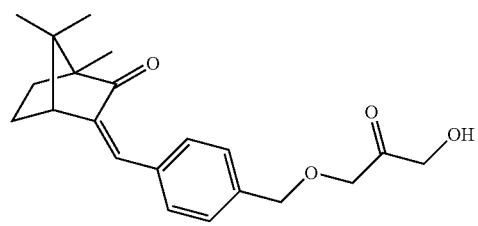 |  |  |  | 3 |  |  |  |  |
| 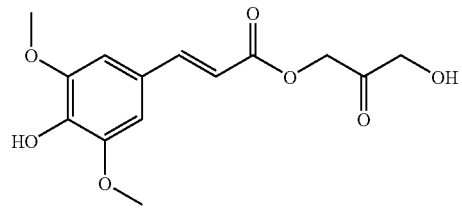 |  |  |  | 1 |  |  |  |  |

TABLE 2-continued

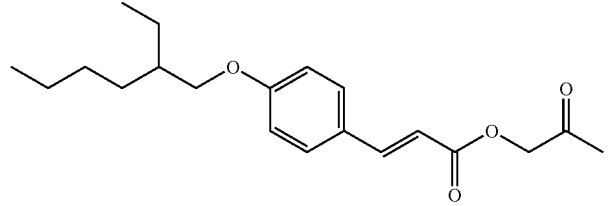

|  |  |  |  | 4 |
|---|---|---|---|---|

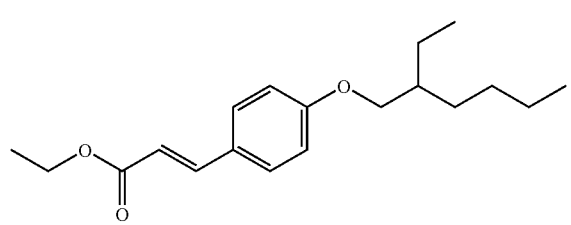

| Ingredient | | | | | | | | |
|---|---|---|---|---|---|---|---|---|
| Stearyl Alcohol (and) Steareth-7 (and) Steareth-10 | 3 | 3 | 3 | 3 | | | | |
| Glyceryl Stearate (and) Ceteth-20 | 3 | 3 | 3 | 3 | | | | |
| Glyceryl Stearate | 3 | 3 | 3 | 3 | | | | |
| Microwax | 1 | 1 | 1 | 1 | | | | |
| Cetearyl Octanoate | 11.5 | 11.5 | 11.5 | 11.5 | | | | |
| Caprylic/Capric Triglyceride | 6 | 6 | 6 | 6 | 14 | 14 | 14 | 14 |
| Oleyl Oleate | 6 | 6 | 6 | 6 | | | | |
| Propylene Glycol | 4 | 4 | 4 | 4 | | | | |
| Glyceryl Stearate SE | | | | | 6 | 6 | 6 | 6 |
| Stearic Acid | | | | | 2 | 2 | 2 | 2 |
| Persea Gratissima | | | | | 8 | 8 | 8 | 8 |
| Propylparabene | 0.05 | 0.05 | 0.05 | 0.05 | 0.05 | 0.05 | 0.05 | 0.05 |
| Methylparabene | 0.15 | 0.15 | 0.15 | 0.15 | 0.15 | 0.15 | 0.15 | 0.15 |
| Tromethamine | | | | | 1.8 | | | |
| Glycerin | | | | | 3 | 3 | 3 | 3 |
| Water | to 100 | to 100 | to 100 | to 100 | to 100 | to 100 | to 100 | to 100 |

| | 2-19 | 2-20 | 2-21 | 2-22 | 2-23 | 2-24 | 2-25 | 2-26 | 2-27 | 2-28 |
|---|---|---|---|---|---|---|---|---|---|---|
| Titanium dioxide | | | | | | | 3 | 3 | | 2 |
| Benzylidene malonate polysiloxane | 1 | 2 | | | | 1 | 1 | | 1 | 0.5 |
| 7,8,3',4'-Tetrahydroxyflavon | | | 1 | 2 | | | | | 1 | 1 |
| 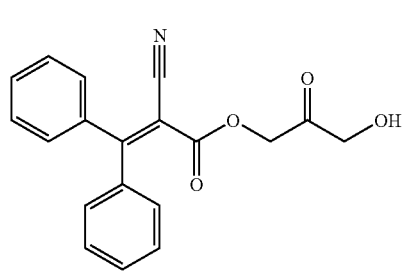 | 1 | 3 | | 2 | | 5 | | 5 | 2 | |
| 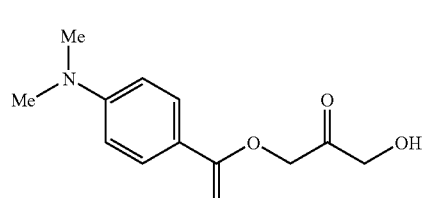 | 5 | 5 | 5 | 5 | 5 | 5 | 5 | 5 | 5 | 5 |
| 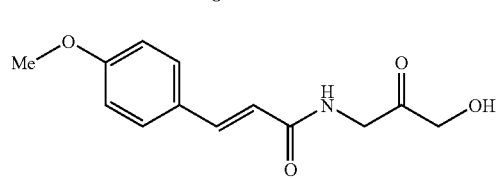 | | | 1 | 2 | 1 | | | 1 | 1 | 0.5 |

TABLE 2-continued

| | | | | | | | | | | |
|---|---|---|---|---|---|---|---|---|---|---|
| Zinc oxide | | | | | 5 | 2 | | | | 2 |
| UV-Pearl, OMC | 15 | 15 | 15 | 15 | 15 | 15 | 15 | 15 | 15 | 15 |
| Caprylic/Capric Triglyceride | 14 | 14 | 14 | 14 | 14 | 14 | 14 | 14 | 14 | 14 |
| Oleyl Oleate | | | | | | | | | | |
| Propylene Glycol | | | | | | | | | | |
| Glyceryl Stearate SE | 6 | 6 | 6 | 6 | 6 | 6 | 6 | 6 | 6 | 6 |
| Stearic Acid | 2 | 2 | 2 | 2 | 2 | 2 | 2 | 2 | 2 | 2 |
| Persea Gratissima | 8 | 8 | 8 | 8 | 8 | 8 | 8 | 8 | 8 | 8 |
| Propylparabene | 0.05 | 0.05 | 0.05 | 0.05 | 0.05 | 0.05 | 0.05 | 0.05 | 0.05 | 0.05 |
| Methylparabene | 0.15 | 0.15 | 0.15 | 0.15 | 0.15 | 0.15 | 0.15 | 0.15 | 0.15 | 0.15 |
| Glyceryl Stearate, Ceteareth-20, Ceteareth-10, Cetearyl Alcohol, Cetyl Palmitate | | | | | | | | | | |
| Ceteareth-30 | | | | | | | | | | |
| Dicaprylyl Ether | | | | | | | | | | |
| Hexyldecanol, Hexyldexyllaurate | | | | | | | | | | |
| Cocoglycerides | | | | | | | | | | |
| Tromethamine | | | | | | | | | | |
| Glycerin | 3 | 3 | 3 | 3 | 3 | 3 | 3 | 3 | 3 | 3 |
| Water | to 100 | to 100 | to 100 | to 100 | to 100 | to 100 | to 100 | to 100 | to 100 | to 100 |

TABLE 3

Gels, numbers in % by weight

| | 3-1 | 3-2 | 3-3 | 3-4 | 3-5 | 3-6 | 3-7 | 3-8 | 3-9 | 3-10 |
|---|---|---|---|---|---|---|---|---|---|---|
| a = aqueaous gel | | | | | | | | | | |
| Titanium dioxide | | 2 | 5 | | | | | | 3 | |
| 2-Methyl-5,7-dihydroxy-chromen-4-on | | | | 1 | 2 | | | | 1 | 1 |
| [structure: Me-O-C6H4-CH=CH-C(=O)-N(Me)-CH2-C(=O)-CH2-OH] | 1 | 3 | | 2 | | 5 | | 5 | 2 | |
| Benzylidene malonate polysiloxane | | | | 1 | 1 | 2 | | | 1 | 1 |
| Methylene Bis-Benztriazolyl Tetramethylbutylphenol | | 1 | | | | 1 | 2 | 1 | | |
| Zinc oxide | | | | | 2 | | | 5 | 2 | |
| UV-Pearl, Ethylhexyl Mehtoxycinnamat | 30 | 15 | 15 | 15 | 15 | 15 | 15 | 15 | 15 | 15 |
| [structure: camphor-benzylidene ether derivative] | | | | | | 2 | | | | |
| Butylmethoxydibenzoylmethane | | 1 | | | | | | | | |
| Phenylbenzimidazole Sulfonic Acid | | | 4 | | | | | | | |
| Prunus Dulcis | 5 | 5 | 5 | 5 | 5 | 5 | 5 | 5 | 5 | 5 |
| Tocopheryl Acetate | 0.5 | 0.5 | 0.5 | 0.5 | 0.5 | 0.5 | 0.5 | 0.5 | 0.5 | 0.5 |
| Caprylic/Capric Triglyceride | 3 | 3 | 3 | 3 | 3 | 3 | 3 | 3 | 3 | 3 |
| Octyldodecanol | 2 | 2 | 2 | 2 | 2 | 2 | 2 | 2 | 2 | 2 |
| Decyl Oleate | 2 | 2 | 2 | 2 | 2 | 2 | 2 | 2 | 2 | 2 |
| PEG-8 (and) Tocopherol (and) Ascorbyl Palmitate (and) Ascorbic Acid (and) Citric Acid | 0.05 | 0.05 | 0.05 | 0.05 | 0.05 | 0.05 | 0.05 | 0.05 | 0.05 | 0.05 |
| Sorbitol | 4 | 4 | 4 | 4 | 4 | 4 | 4 | 4 | 4 | 4 |
| Polyacrylamide (and) C13-14 Isoparaffin (and) Laureth-7 | 3 | 3 | 3 | 3 | 3 | 3 | 3 | 3 | 3 | 3 |
| Propylparabene | 0.05 | 0.05 | 0.05 | 0.05 | 0.05 | 0.05 | 0.05 | 0.05 | 0.05 | 0.05 |

TABLE 3-continued

| | \multicolumn{10}{c}{Gels, numbers in % by weight} |
| --- | --- | --- | --- | --- | --- | --- | --- | --- | --- | --- |
| | 3-1 | 3-2 | 3-3 | 3-4 | 3-5 | 3-6 | 3-7 | 3-8 | 3-9 | 3-10 |
| Methylparabene | 0.15 | 0.15 | 0.15 | 0.15 | 0.15 | 0.15 | 0.15 | 0.15 | 0.15 | 0.15 |
| Tromethamine | | | 1.8 | | | | | | | |
| Water | to 100 | to 100 | to 100 | to 100 | to 100 | to 100 | to 100 | to 100 | to 100 | to 100 |

INDEX OF FIGURES

FIG. 1: UV absorption spectra of 1-hydroxy-3-[(E)-3-(4-methoxyphenyl)-2-propenoyloxy]-2-oxopropane (Example 1a) and 1-hydroxy-3-(2-cyano-3,3-diphenylacryloyloxy)-2-oxopropane (Example 1b) (in each case measured in 2-propanol at a concentration of 1 mg/100 ml)

Figure 2:
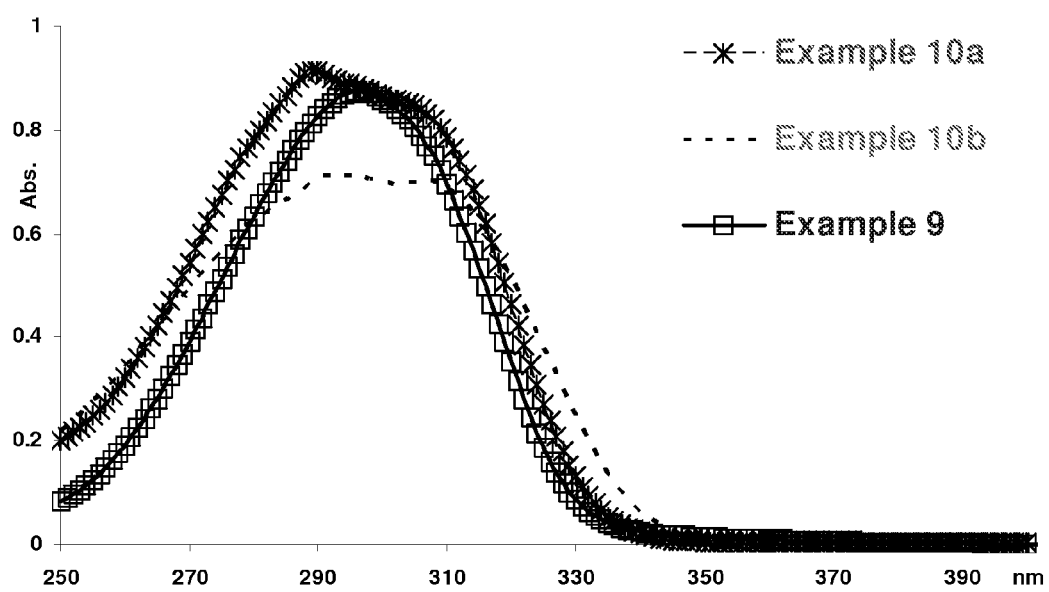

FIG. 2: UV absorption spectra of 3-[4-(3-hydroxy-2-oxopropoxymethyl)benzylidene]-4,7,7-trimethylbicyclo[2.2.1]heptan-2-one (Example 9), N-(2,3-dihydroxypropyl)-(E)-3-(4-methoxyphenyl)acrylamide (Example 10a) and N-(2,3-dihydroxypropyl)-N-methyl-(E)-3-(4-methoxyphenyl)acrylamide (Example 10b) (in each case measured in 2-propanol at a concentration of 1 mg/100 ml).

The invention claimed is:

1. A compound of formula I

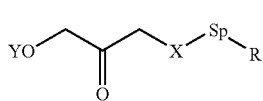

I in which
X stands for O, $S(O)_m$ or $NR^1$,
Y stands for $R^1$, $SiR^3R^4R^5$ or -Sp-R,
$R^1$ stands for H, $C_{1-30}$-alkyl or R,
$R^2$, $R^3$, $R^4$ and $R^5$ each, independently of one another, stand for $C_{1-30}$-alkyl,
Sp stands for —$(CH_2)_n$—, —$(CH_2)_n$—C(=O)—$(CH_2)_o$— or —$(CH_2)_n$—C(=O)—$(CH_2)_o$—X—$(CH_2)_p$—,
m stands for an integer 0, 1 or 2,
n, o, p, stand for an integer, independently of one another, in the range beginning with 0 and ending with 40 and
R stands for

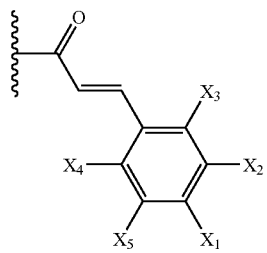

in which
$X_1$, $X_2$, $X_3$, $X_4$
and $X_5$ each, independently of one another, denote H, OH, $CH_3COO$, an alkyl radical having 1 to 8 C atoms, an alkoxy radical having 1 to 8 C atoms, or a monoglycoside radical, and
where R may in turn be substituted by one or more -Sp-X—$CH_2$—C(=O)—$CH_2$—OH groups,
where different R and X in formula I may stand for identical or different radicals.

2. A compound according to claim 1, wherein Y stands for H.

3. A compound according to claim 1, wherein
$X_1$, $X_2$, $X_3$, $X_4$
and $X_5$ each, independently of one another, denote H, OH, $CH_3COO$, an alkyl radical having 1 to 8 C atoms, —O—$C(CH_3)_3$, —O—$CH(CH_3)_2$, -ethylhexyloxy, or a monoglycoside radical.

4. A compound according to claim 1, which is

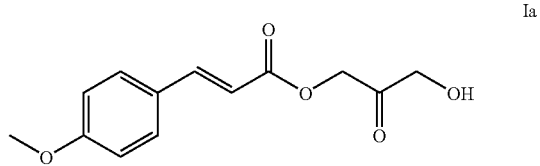

Ia

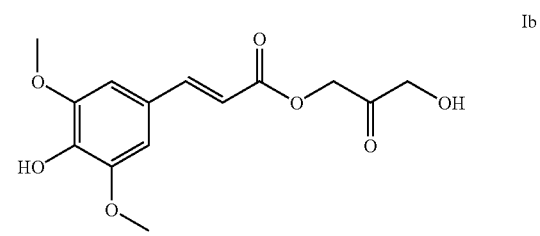

Ib

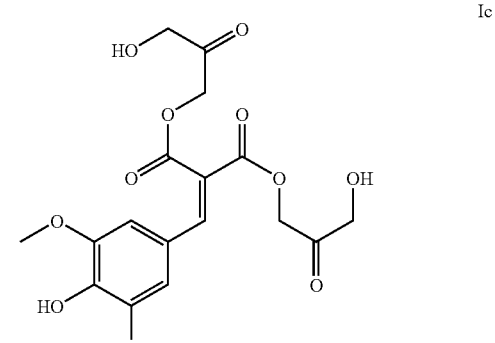

Ic

-continued
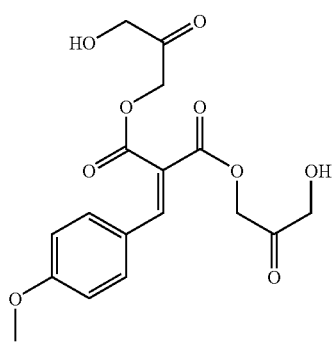
Id
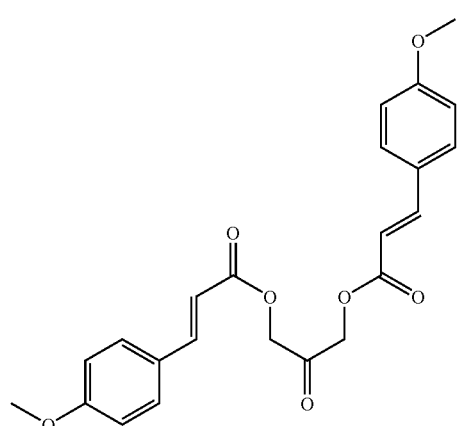
Ie
or
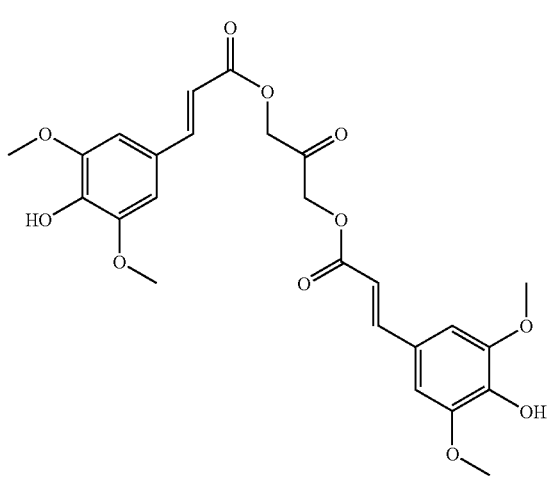
If
5. A compound according to claim 1, which is
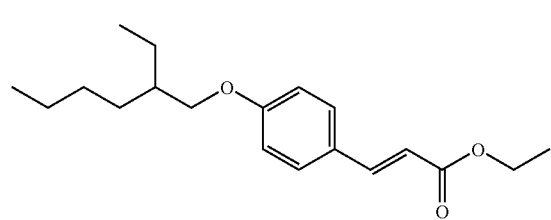
It
-continued
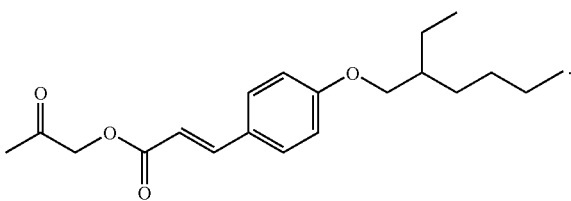
Id
6. A compound according to claim 1, which is
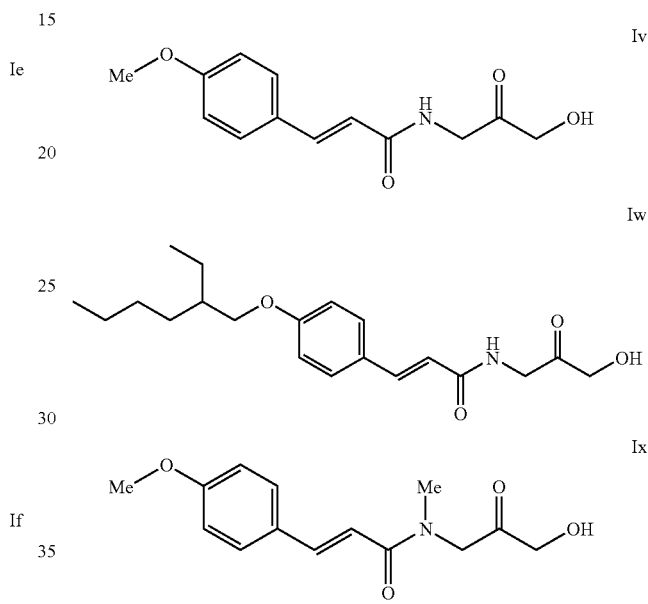
Iv
Iw
Ix
Iaa
Iab
or
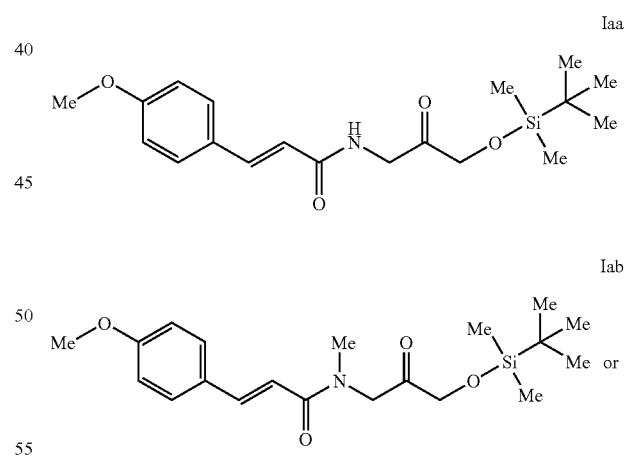
Iac

7. A compound of formula II

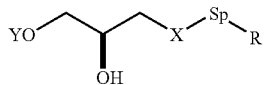

in which

X stands for O, $S(O)_m$ or $NR^1$,

Y stands for H, $R^1$, $SiR^3R^4R^5$ or -Sp-R, $R^1$ stands for H, $C_{1-30}$-alkyl or R, $R^2$, $R^3$, $R^4$ and $R^5$ each, independently of one another, stand for $C_{1-30}$-alkyl, Sp stands for $-(CH_2)_n-$, $-(CH_2)_n-C(=O)-(CH_2)_o-$ or $-(CH_2)_n-C(=O)-(CH_2)_o-X-(CH_2)_p-$, m stands for an integer 0, 1 or 2, n, o, p, stand for an integer, independently of one another, in the range beginning with 0 and ending with 40 and R stands for

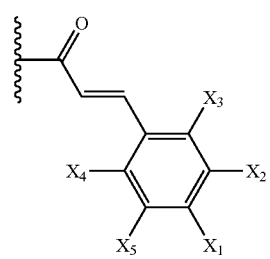

in which $X_1$, $X_2$, $X_3$, $X_4$ and $X_5$ each, independently of one another, denote H, OH, $CH_3COO$, an alkyl radical having 1 to 8 C atoms, an alkoxy radical having 1 to 8 C atoms, or a monoglycoside radical, and where R may in turn be substituted by one or more -Sp- X—$CH_2$—C(=O)—$CH_2$—OH groups, where different R and X in formula II may stand for identical or different radicals.

8. A compound according to claim 7, wherein $X_1$, $X_2$, $X_3$, $X_4$ and $X_5$ each, independently of one another, denote H, OH, $CH_3COO$, an alkyl radical having 1 to 8 C atoms, —O—$C(CH_3)_3$, —O—$CH(CH_3)_2$, -ethylhexyloxy, or a monoglycoside radical.

9. A compound according to claim 7, which is

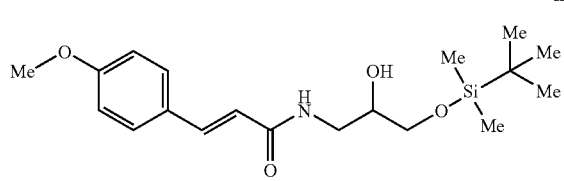

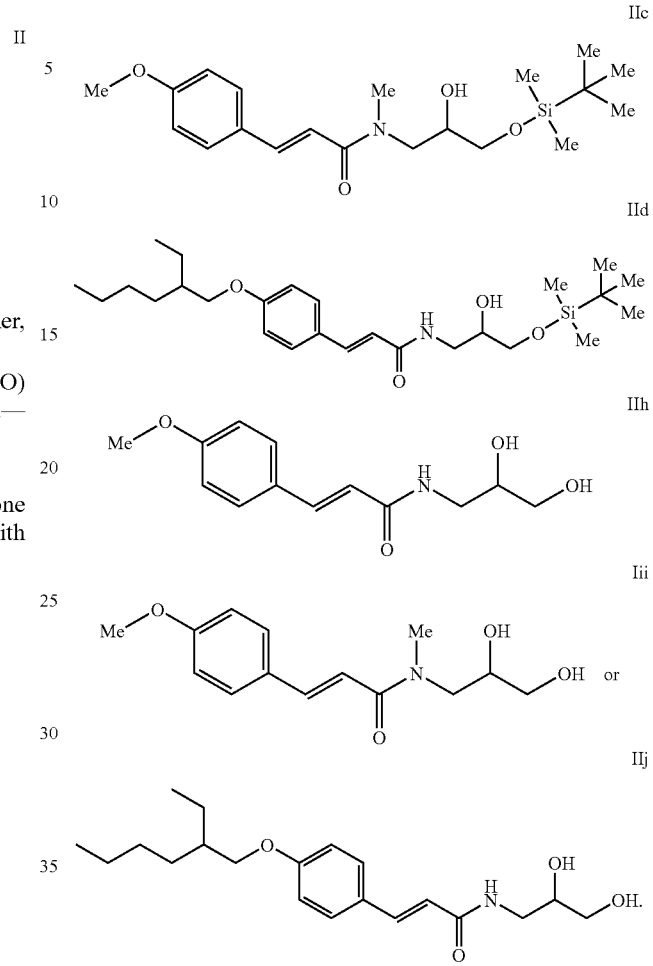

10. A process for preparing a compound of formula I according to claim 1 where X stands for O, comprising reacting dihydroxyacetone or a dihydroxyacetone derivative in which a hydroxyl group is provided with a protective function with an acid chloride R—$(CH_2)_m$—(C=O)Cl, wherein R and m are as defined for the compound of formula I.

11. A process for preparing a compound of formula II according to claim 7 where X stands for O, comprising reacting an acid chloride R—$(CH_2)_m$—(C=O)Cl, wherein R and m are as defined for the compound of formula II, with a compound

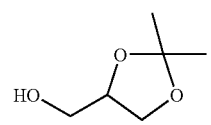

and subsequently cleaving the acetal.

12. A process for preparing a compound of formula I according to claim 1 where X stands for O, comprising reacting 2,2-dimethoxy-1,3-propanediol with a compound R-Sp-Hal, where Hal stands for Cl, Br or I, and R and Sp are as defined for the compound of formula I, and subsequently hydrolysing the dimethoxy function to the ketone.

13. A process for preparing a compound of formula II according to claim 7 where X stands for NR$^1$, comprising reacting an acid chloride R—(CH$_2$)$_n$—C(=O)Cl or a compound R-Sp-Hal, where Hal stands for Cl, Br or I, and R, Sp and n are as defined for the compound of formula I with a compound

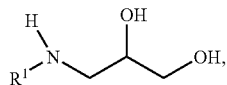

wherein R$^1$ is as defined for the compound of formula I.

14. A process for preparing a compound of formula I according to claim 1, comprising oxidizing the secondary hydroxyl group of a compound of formula II by an oxidant

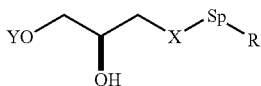 II in which
X stands for O, S(O)$_m$ or NR$^1$,
Y stands for H, R$^1$, SiR$^3$R$^4$R$^5$ or -Sp-R,
R$^1$ stands for H, C$_{1-30}$-alkyl or R,
R$^2$, R$^3$, R$^4$ and R$^5$ each, independently of one another, stand for C$_{1-30}$-alkyl,
Sp stands for —(CH$_2$)$_n$—, —(CH$_2$)$_n$—C(=O)—(CH$_2$)$_o$— or —(CH$_2$)$_n$—C(=O)—(CH$_2$)$_o$—X—(CH$_2$)$_p$—,
m stands for an integer 0, 1 or 2,
n, o, p, stand for an integer, independently of one another, in the range beginning with 0 and ending with 40 and
R stands for

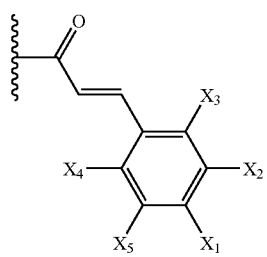

in which
X$_1$, X$_2$, X$_3$X$_4$
and X$_5$ each independently of one another denote H, OH, CH$_3$COO, an alkyl radical having 1 to 8 C atoms, an alkoxy radical having 1 to 8 C atoms, or a monoglycoside radical, and
where R may in turn be substituted by one or more -Sp-X—CH$_2$—C(=O)—CH$_2$—OH groups,
where different R and X in formula II may stand for identical or different radicals.

15. A composition comprising a vehicle, and
0.001 to 99% by weight of one or more compounds of the formula I

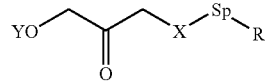 I in which
X stands for O, S(O)$_m$ or NR$^1$,
Y stands for R$^1$, SiR$^3$R$^4$R$^5$ or -Sp-R,
R$^1$ stands for H, C$_{1-30}$-alkyl or R,
R$^2$, R$^3$, R$^4$ and R$^5$ each, independently of one another, stand for C$_{1-30}$-alkyl,
Sp stands for —(CH$_2$)$_n$—, —(CH$_2$)$_n$—C(=O)—(CH$_2$)$_o$— or —(CH$_2$)$_n$—C(=O)—(CH$_2$)$_o$—X—(CH$_2$)$_p$—,
m stands for an integer 0, 1 or 2,
n, o, p, stand for an integer, independently of one another, in the range beginning with 0 and ending with 40 and
R stands for

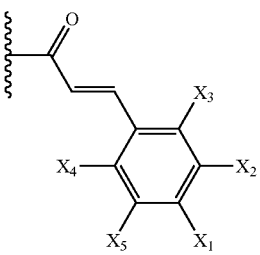

in which
X$_1$, X$_2$, X$_3$, X$_4$
and X$_5$ each, independently of one another, denote H, OH, CH$_3$COO, an alkyl radical having 1 to 8 C atoms, an alkoxy radical having 1 to 8 C atoms, or a monoglycoside radical, and
where R may in turn be substituted by one or more -Sp-X—CH$_2$—C(=O)—CH$_2$—OH groups,
where different R and X in formula I may stand for identical or different radicals, or 0.001 to 99% by weight of one or more compounds of the formula II

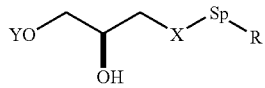 II in which
X stands for O, S(O)$_m$ or NR$^1$,
Y stands for H, R$^1$, SiR$^3$R$^4$R$^5$ or -Sp-R,
R$^1$ stands for H, C$_{1-30}$-alkyl or R,
R$^2$, R$^3$, R$^4$ and R$^5$ each, independently of one another, stand for C$_{1-30}$-alkyl,
Sp stands for —(CH$_2$)$_n$—, —(CH$_2$)$_n$—C(=O)—(CH$_2$)$_o$— or —(CH$_2$)$_n$—C(=O)—(CH$_2$)$_o$—X—(CH$^2$)$_p$—, m stands for an integer 0, 1 or 2, n, o, p, stand for an integer, independently of one another, in the range beginning with 0 and ending with 40 and R stands for

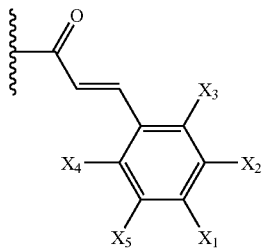

in which $X_1, X_2, X_3, X_4$ and $X_5$ each, independently of one another, denote H, OH, $CH_3COO$, an alkyl radical having 1 to 8 C atoms, an alkoxy radical having 1 to 8 C atoms, or a monoglycoside radical, and where R may in turn be substituted by one or more -Sp-X—$CH_2$—C(═O)—$CH_2$—OH groups, where different R and X in formula II may stand for identical or different radicals or a topically tolerated salt thereof.

16. A composition according to claim 15, wherein the one or more compounds of formula I or II are present in the composition in an amount of 0.01 to 20% by weight.

17. A composition according claim 15, further comprising one or more antioxidants and/or one or more further UV filters.

18. A method for absorbing UV radiation and thus protecting skin or hair against aging, dry skin, wrinkling or pigment defects and/or for reducing damaging effects of UV rays on the skin, comprising administering to the skin or hair a composition according to claim 15.

19. A method for reduction of skin unevenness, wrinkles, fine lines, rough skin or large-pored skin, comprising administering to the skin a composition according to claim 15.

20. A process for preparing a composition according to claim 15, comprising mixing at least one compound of the formula I or II with a vehicle which is suitable cosmetically or dermatologically or for foods.

21. A method for caring, preserving or improving the general condition of the skin or hair, comprising administering to the skin or hair a composition according to claim 15.

22. A compound according to claim 1, wherein X stands for O.

23. A compound according to claim 1, wherein

Y stands for Sp-R, and

X stands for O.

24. A compound according to claim 1, wherein X stands for $NR^1$.

25. A method for treating time- and/or light-induced ageing processes of the human skin or human hair, comprising administering to the skin or hair a composition according to claim 15.

* * * * *

UNITED STATES PATENT AND TRADEMARK OFFICE
CERTIFICATE OF CORRECTION

| | | |
|---|---|---|
| PATENT NO. | : 7,863,478 B2 | Page 1 of 1 |
| APPLICATION NO. | : 11/573657 | |
| DATED | : January 4, 2011 | |
| INVENTOR(S) | : Carola et al. | |

It is certified that error appears in the above-identified patent and that said Letters Patent is hereby corrected as shown below:

Column 95, line 54 reads "-O-C(CH$_{33}$, -O-CH(CH$_3$)$_2$, -ethylhexyloxy, or a"
should read -- -O-C(CH$_3$)$_3$, -O-CH(CH$_3$)$_2$, -ethylhexyloxy, or a --

Signed and Sealed this
Eighth Day of March, 2011

David J. Kappos
*Director of the United States Patent and Trademark Office*